(12) United States Patent
Zhu et al.

(10) Patent No.: US 6,911,428 B2
(45) Date of Patent: Jun. 28, 2005

(54) DIARYL PEPTIDES AS NS3-SERINE PROTEASE INHIBITORS OF HEPATITIS C VIRUS

(75) Inventors: Zhaoning Zhu, East Windsor, NJ (US); Zhong-Yue Sun, Parlin, NJ (US); Srikanth Venkatraman, Woodbridge, NJ (US); F. George Njoroge, Warren, NJ (US); Ashok Arasappan, Bridgewater, NJ (US); Bruce A. Malcolm, Westfield, NJ (US); Viyyoor M. Girijavallabhan, Parsippany, NJ (US); Raymond G. Lovey, West Caldwell, NJ (US); Kevin X. Chen, Iselin, NJ (US)

(73) Assignee: Schering Corporation, Kenilworth, NJ (US)

( * ) Notice: Subject to any disclaimer, the term of this patent is extended or adjusted under 35 U.S.C. 154(b) by 364 days.

(21) Appl. No.: 10/013,071

(22) Filed: Dec. 10, 2001

(65) Prior Publication Data

US 2002/0147139 A1 Oct. 10, 2002

Related U.S. Application Data

(60) Provisional application No. 60/254,869, filed on Dec. 12, 2000.

(51) Int. Cl.[7] .................. A61K 38/17; A61K 31/33; C07K 7/64
(52) U.S. Cl. .................. 514/9; 530/317; 540/455; 514/183
(58) Field of Search .................. 514/18, 9, 12, 514/183, 314; 530/330, 331, 350, 317; 540/455

(56) References Cited

U.S. PATENT DOCUMENTS 5,712,145 A 1/1998 Houghton et al.

FOREIGN PATENT DOCUMENTS

| EP | 381 216 | 8/1990 |
|---|---|---|
| WO | WO 89/04669 | 6/1989 |
| WO | WO 98/07734 | 2/1998 |
| WO | WO 98/17679 | 4/1998 |
| WO | WO 98/22496 | 5/1998 |
| WO | WO 00/09543 | 2/2000 |
| WO | WO 00/09558 | 2/2000 |

OTHER PUBLICATIONS

Llinas–Brunet et al.: "Studies on the C–Terminal of Hexapeptide Inhibitors of the Hepatitis C Virus Serine Protease" *Bioorganic & Medicinal Chemistry Letters,* Oxford, GB, 8(19):2719–2724 (1998).
Pizzi, (1994) *Proc. Natl. Acad. Sci. (USA)* 91:888–892.
Failla (1996) *folding & Design* 1:35–42.
Kollykhalov (1994) *J. Virol.* 68:7525–7533.
Komoda (1994) *J. Virol* 68:7351–7357.
Landro (1997) *Biochem* 36:9340–9348.
Ingallinella (1998) *Biochem* 37:8906–8914.
Llinas–Brunet (1998) *Bioorg. Med. Chem. Lett,* 8:1713–1718.
Martin (1998) *Biochem* 37:11459–11468.
Dimasi (1997) *J. Virol.* 71:7461–7469.
Martin (1997) *Protein Eng.* 10:607–614.
Elzouki (1997) *J. Hepat.* 27:42–48.
*Bio World Today* 9(217): 4 (Nov. 10, 1998).
Berenguer (1998) *Proc. Assoc. Am. Physicians* 110(2): 98–112.
Hoofnagle (1997) *New England Journal Med.* 336:347.
Zhang (199) *Analytical Biochemistry* 270:268–275.
Sali (1998) *Biochemistry* 3392–3401.
Barlos (1991) *Int. J. Pept. Protein Res* 513–520.
Holmberg (1979) *Acta Chem. Scand.* B33:410–412.
Agrawal(1999) *Hepatology* Supplement to vol. 30 "Development and Characterization of Hepatitis C Virus Serine Protease Cell–based Trans–Cleavage Assay".
Hughes (1992) *Org. Reactions* 42:335.
Heck (1989) *Org. Reactions* 27:345–390.
Han, (2000) *Bioorganic & Medicinal Chemistry Letters 10* "α–Ketoamides, α–Ketoesters and α–Kiketones as HCV NS3 Protease Inhibitors" pp. 711–713.
Marchetti(1999)*Synlett*, vol. S1, "Synthesis of Two Novel Cyclic Biphenyl Ether Analogs of an Inhibitor of HCV NS3 Protease", pp 1000–1002.

*Primary Examiner*—Robert A. Wax
*Assistant Examiner*—Robert B. Mondesi
(74) *Attorney, Agent, or Firm*—Palaiyur S. Kalyanaraman

(57) ABSTRACT

The present invention is directed to certain diaryl amide compounds as NS3-Serine protease inhibitors of hepatitis C virus. A particularly preferred compound is of the formula:

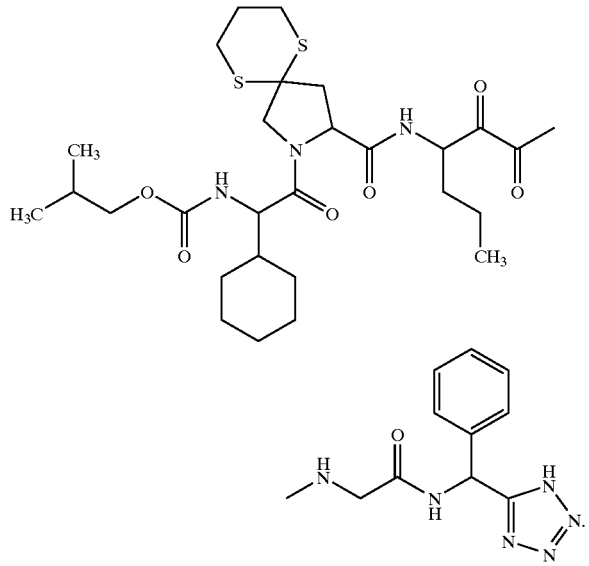

20 Claims, No Drawings

DIARYL PEPTIDES AS NS3-SERINE PROTEASE INHIBITORS OF HEPATITIS C VIRUS

This application claims priority from provisional application, Ser. No. 60/254,869 filed Dec. 12, 2000.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses diaryl peptide compounds as inhibitors of the HCV NS3/NS4a serine protease.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci. (USA)* 91:888–892, Failla et al. (1996) *Folding & Design* 1:35–42. The NS3/NS4a cleavage site is also more tolerant of mutagenesis than the other sites. See, e.g., Kollykhalov et al. (1994) *J. Virol.* 68:7525–7533. It has also been found that acidic residues in the region upstream of the cleavage site are required for efficient cleavage. See, e.g., Komoda et al. (1994) *J. Virol.* 68:7351–7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340–9348, Ingallinella et al. (1998) *Biochem.* 37:8906–8914, Llinàs-Brunet et al. (1998) *Bioorg. Med. Chem. Lett.* 8:1713–1718), inhibitors based on the 70-amino acid polypeptide eglin c (Martin et al. (1998) *Biochem.* 37:11459–11468, inhibitors affinity selected from human pancreatic secretory trypsin inhibitor (hPSTI-C3) and mini-body repertoires (MBip) (Dimasi et al. (1997) *J. Virol.* 71:7461–7469), $cV_HE2$ (a "camelized" variable domain antibody fragment) (Martin et al.(1997) *Protein Eng.* 10:607–614), and α1-antichymotrypsin (ACT) (Elzouki et al.) (1997) *J. Hepat.* 27:42–28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than 1%.

Reference is made to A. Marchetti et al, *Synlett*, S1, 1000–1002 (1999) describing the synthesis of bicylic analogs of an inhibitor of HCV NS3 protease. A compound disclosed therein has the formula:

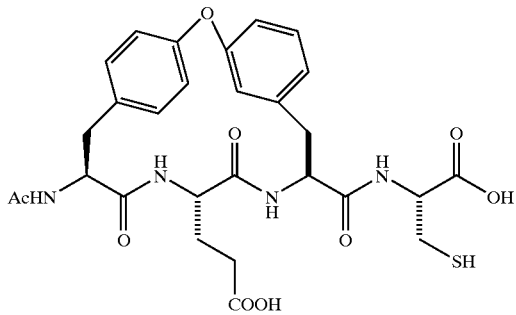

Reference is also made to WO 00/09558 (Assignee: Boehringer Ingelheim Limited; Published Feb. 24, 2000) which discloses peptide derivatives of the formula:

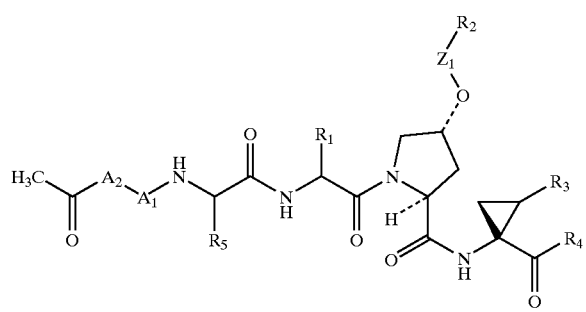

where the various elements are defined therein. An illustrative compound of that series is:

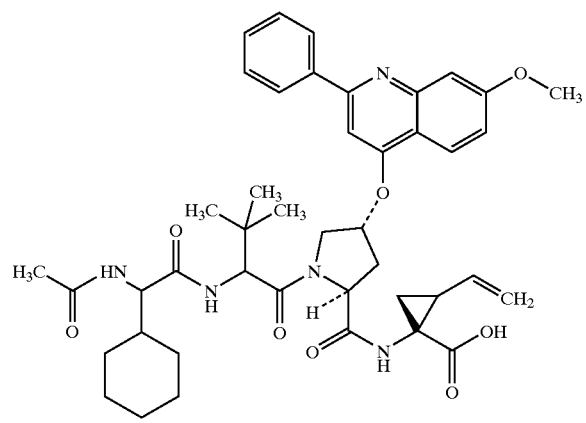

Reference is also made to WO 00/09543 (Assignee: Boehringer Ingelheim Limited; Published Feb. 24, 2000) which discloses peptide derivatives of the formula:

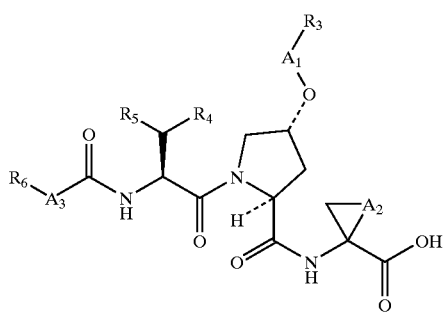

where the various elements are defined therein. An illustrative compound of that series is:

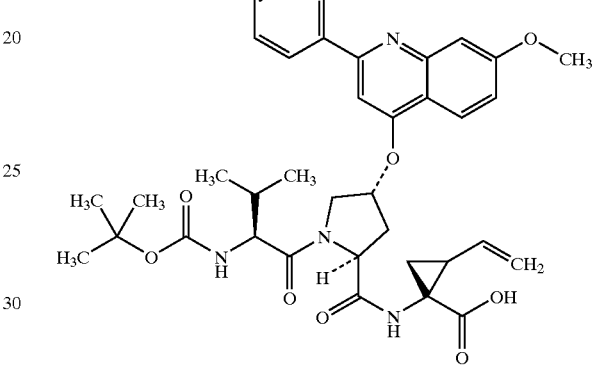

Current therapies for hepatitis C include interferon-α (INF$_\alpha$) and combination therapy with ribavirin and interferon. See, e.g. Beremguer et al. (1998) *Proc. Assoc. Am. Physicians* 110(2):98–112. These therapies suffer from a low sustained response rate and frequent side effects. See, e.g., Hoofnagle et al. (1997) *N. Engl. J. Med.* 336:347. Currently, no vaccine is available for HCV infection.

Pending patent applications, Ser. No. 60/194,607, filed Apr. 5, 2000, and Ser. No. 60/198,204, filed Apr. 19, 2000, both having common ownership with the present application, disclose certain macrocyclic NS-3 serine protease inhibitors of hepatitis C virus.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The presently disclosed compounds generally contain about four or more amino acid residues and less than about twelve amino acid residues. Specifically, the present application discloses peptide compounds, defined further below in Formulae I, II and III.

DETAILED DESCRIPTION OF PREFERRED EMBODIMENTS

In its first embodiment, the present invention provides a compound of Formula I:

Formula I

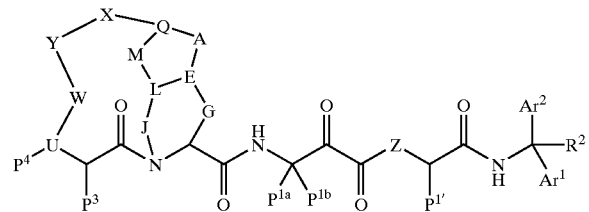

wherein:

X and Y are independently selected from the moieties: alkyl, alkyl-aryl, heteroalkyl, heteroaryl, aryl-heteroaryl, alkyl-heteroaryl, cycloalkyl, alkyl ether, alkyl-aryl ether, aryl ether, alkyl amino, aryl amino, alkyl-aryl amino, alkyl thio, alkyl-aryl thio, aryl thio, alkyl sulfone, alkyl-aryl sulfone, aryl sulfone, alkyl-alkyl sulfoxide, alkyl-aryl sulfoxide, alkyl amide, alkyl-aryl amide, aryl amide, alkyl sulfonamide, alkyl-aryl sulfonamide, aryl sulfonamide, alkyl urea, alkyl-aryl urea, aryl urea, alkyl carbamate, alkyl-aryl carbamate, aryl carbamate, alkyl-hydrazide, alkyl-aryl hydrazide, alkyl hydroxamide, alkyl-aryl hydroxamide, alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, heteroarylaminocarbonyl or a combination thereof, with the proviso that X and Y may optionally be additionally substituted with $X^{11}$ or $X^{12}$;

$X^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

W may be present or absent, and if W is present, W is selected form C=O, C=S, or $SO_2$;

Q may be present or absent, and when Q is present, Q is CH, N, P, $(CH_2)_p$, $(CHR)_p$, $(CRR')_p$, O, RNR, S, or $SO_2$; and when Q is absent, M is also absent, A is directly linked to X;

A is O, $CH_2$, $(CHR)_p$, $(CHR—CHR')_p$, $(CRR')_p$, NR, S, $SO_2$ or a bond;

U is selected form O, N, or CH;

E is CH, N or CR, or a double bond towards A, L or G;

G may be present or absent, and when G is present, G is $(CH_2)_p$, $(CHR)_p$, or $(CRR')_p$; and when G is absent, J is present and E is directly connected to the carbon atom where G was connected to;

J may be absent or present, and when J is present, J is $(CH_2)_p$, $(CHR)_p$, or $(CRR')_p$, $SO_2$, NH, NR or O; and when J is absent, G is present and L is directly linked to nitrogen;

L may be present or absent, and when L is present, L is CH, CR, O, S or NR; and when L is absent, then M may be absent or present, and if M is present with L being absent, then M is directly and independently linked to E, and J is directly and independently linked to E;

M may be present or absent, and when M is present, M is O, NR, S, $SO_2$, $(CH_2)_p$, $(CHR)_p$, $(CHR—CHR')_p$, or $(CRR')_p$;

p is a number from 0 to 6;

R and R' are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, cyano, nitro; (cycloalkyl)-alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl; with said alkyl, heteroalkyl, alkenyl, heteroalkenyl, aryl, heteroaryl, cycloalkyl and heterocycloalkyl moieties may be optionally substituted, with said term "substituted" referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, cyano, nitro, sulfonamido; and $P^{1a}$, $P^{1b}$, $P^{1'}$ and $P^3$ are independently selected from:

H, C1–C10 straight or branched chain alkyl, C2–C10 straight or branched chain alkenyl, and C3–C8 cycloalkyl, C3–C8 heterocyclic; (cycloalkyl)alkyl or (heterocyclyl)alkyl, wherein said cycloalkyl is made up of 3 to 8 carbon atoms, and zero to 6 oxygen, nitrogen, sulfur, or phosphorus atoms, and said alkyl is of 1 to 6 carbon atoms;

aryl, heteroaryl, arylalkyl, or heteroarylalkyl, wherein said alkyl is of 1 to 6 carbon atoms;

wherein said alkyl, alkenyl, cycloalkyl, heterocyclyl; (cycloalkyl)alkyl and (heterocyclyl)alkyl moieties may be optionally substituted with R", and further wherein said $P^{1a}$ and $P^{1b}$ may optionally be joined to each other to form a spirocyclic or spiroheterocyclic ring, with said spirocyclic or spiroheterocyclic ring containing zero to six oxygen, nitrogen, sulfur, or phosphorus atoms, and may be additionally optionally substituted with R";

R" is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from R";

Z is O, NH or NR''';

R''' is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that R''' may be additionally optionally substituted with R'';

$Ar^1$ and $Ar^2$ are independently selected from phenyl; 2-pyridyl, 3-pyridyl, 4-pyridyl or their corresponding N-oxides; 2-thiophenyl; 3-thiophenyl; 2-furanyl; 3-furanyl; 2-pyrrolyl; 3-pyrrolyl; 2-imidazolyl; 3(4)-imidazolyl; 3-(1,2,4-triazolyl); 5-tetrazolyl; 2-thiazolyl; 4-thiazolyl; 2-oxazolyl; or 4-oxazolyl; either or both of which may be optionally substituted with $R^1$;

$R^1$ is H, halogen, cyano, nitro, $CF_3$, $Si(alkyl)_3$, straight-chain or branched lower alkyl, alkenyl, alkynyl, cycloalkyl, cycloalkyl-alkyl, aryl, alkylaryl, arylalkyl, heteroaryl, hydroxy, alkoxy, aryloxy, alkoxycarbonyloxy, (alkylamino)carbonyloxy, mercapto, alkylthio, arylthio, alkylsulfinyl, heterocyclylsulfinyl, arylsulfinyl, heteroarylsulfinyl, alkylsulfonyl, heterocyclylsulfonyl, arylsulfonyl, heteroarylsulfonyl, alkylcarbonyl, arylcarbonyl, carboxy, alkoxycarbonyl, aryloxycarbonyl, heteroaryloxycarbonyl, alkyaminocarbonyl, arylaminocarbonyl, amino, alkylamino, arylamino, alkylsulfonamide, arylsulfonamide, alkoxycarbonbylamino, alkylureido, or arylureido;

$P^4$ is H, linear or branched alkyl, arylalkyl or aryl; and $R^2$ is H, cyano, $CF_3$, straight-chain or branched lower alkyl, alkenyl, alkynyl, cycloalkyl, cycloalkyl-alkyl, aryl, alkylaryl, arylalkyl, heteroaryl, alkylsulfonyl, arylsulfonyl, carboxy, alkoxycarbonyl, aryloxycarbonyl, alkyaminocarbonyl, (allylamino)carbonyl), or arylaminocarbonyl.

Suitably, $R^{2'}$ is selected from the group consisting of H, alkyl, alkenyl, alkoxycarbonyl, or (allylamino) carbonyl and preferably wherein $R^{2'}$ is H, U is N and $P^4$ is H.

Advantageously, $Ar^1$ and $Ar^2$ are independently selected from the group consisting of phenyl, 2-thiophenyl, 2-furanyl, 3-furanyl, 3(4)-imidazolyl, 3-(1,2,4-triazolyl), 5-tetrazolyl, or 2-thiazolyl, preferably $Ar^2$ is phenyl and $Ar^1$ is selected from the group consisting of 3-(1,2,4-triazolyl), 5-tetrazolyl, or 2-thiazolyl and U is N and $P^4$ is H.

Suitably, $R^1$ is H, $CF_3$, $CH_3$, alkyl or alkenyl.

Usually, $P^{1'}$ is either H or $CH_3$.

Suitably, when $P^{1'}$ is H then $P^{1'}$ and the adjacent nitrogen and carbonyl moieties correspond to the residuum of a glycine unit.

Preferably, $P^{1a}$ and $P^{1b}$ are independently selected from the group consisting of the following moieties:

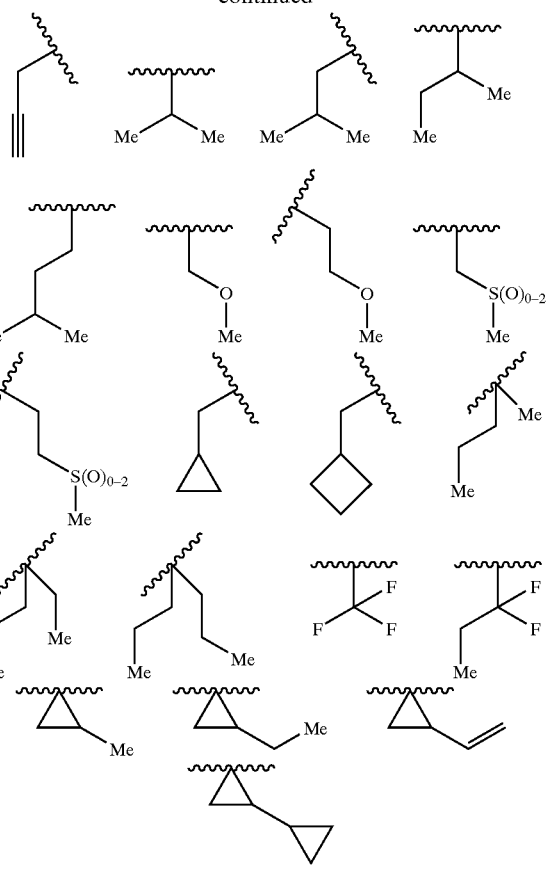

Advantageously, U is N and $P^4$ is H and Z is NH.

Suitably, $P^3$ is selected from the group consisting of:

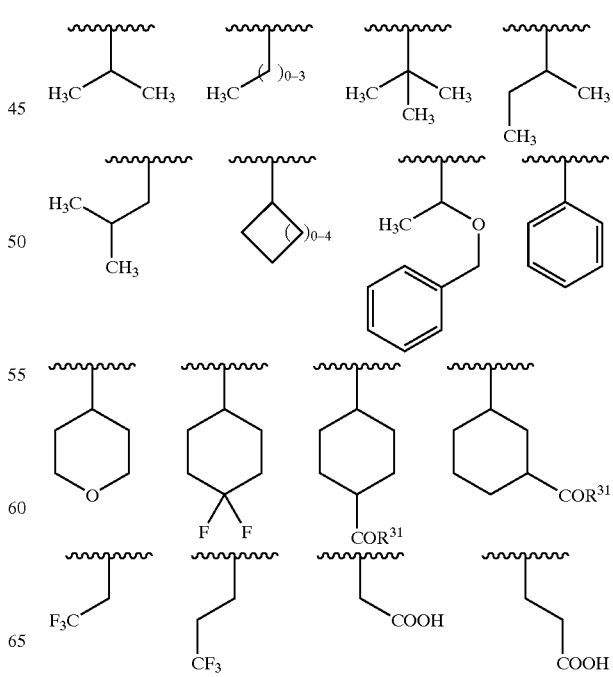

-continued

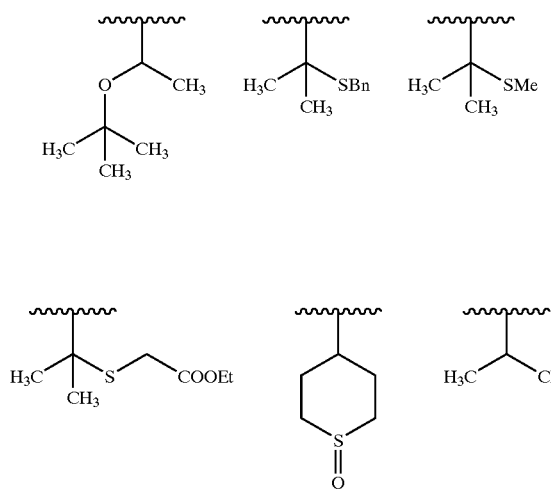

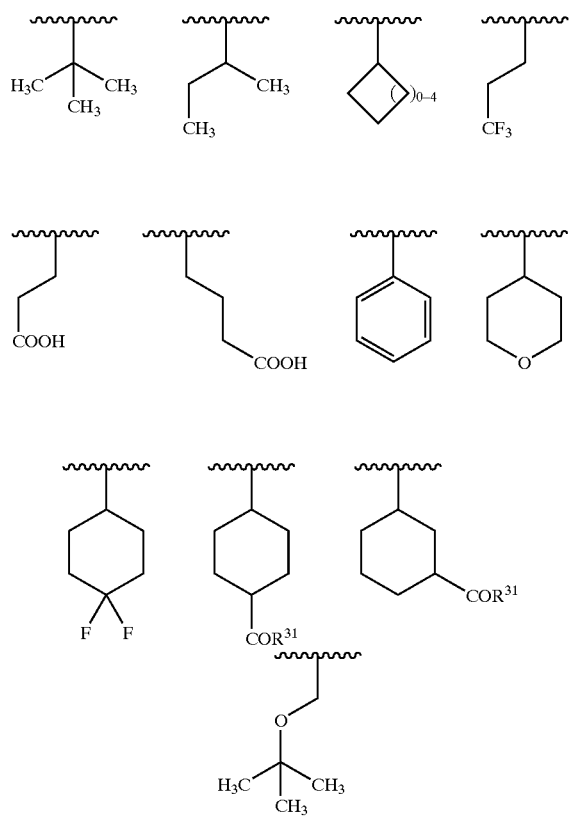

wherein $R^{31}$=OH or O-alkyl.

Suitably, $P^4$ is selected from the group consisting of H, tertiary butyl, isobutyl and phenyl substituents.

Suitably, Z is NH and U is N and $P^3$ is as set forth above.

In another suitable expression of Formula I, the moiety:

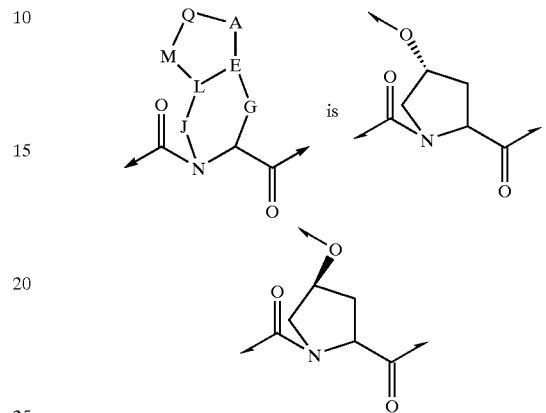

Suitably, Z is NH and U is N.

The compound of Formula I, wherein said compound is selected from the group consisting of compounds having the structural formulae:

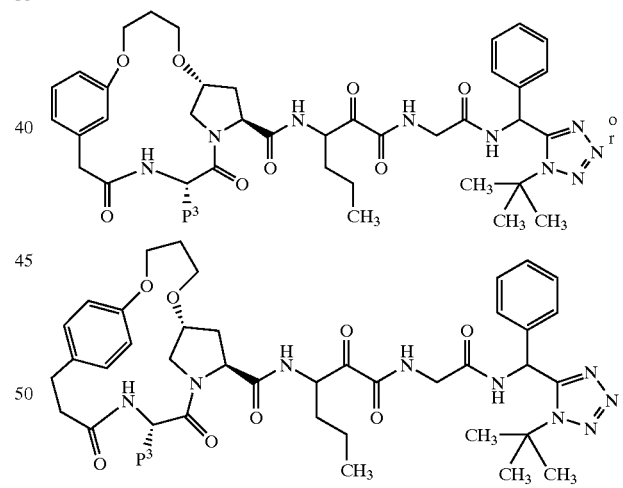

wherein $P^3$ is an isopropyl, tertiary butyl, cyclopentyl, or cyclohexyl moiety.

A preferred compound of Formula I exhibiting HCV protease inhibitory activity, including enantiomers, stereoisomers and tautomers of said compound, and pharmaceutically acceptable salts or solvates of said compound, said compound being selected from the compounds of structures listed below:

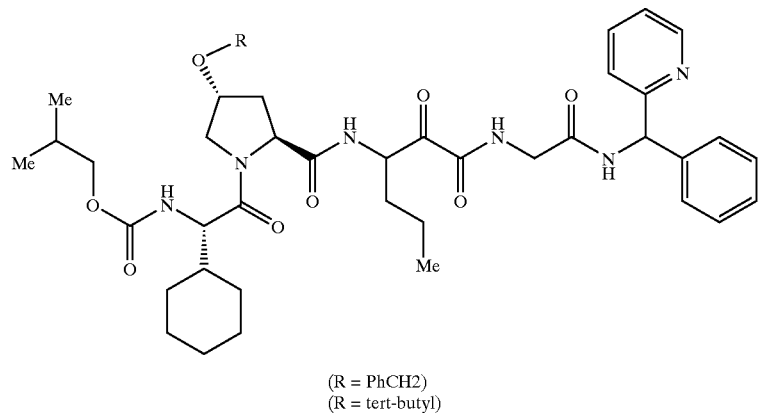
(R = PhCH2)
(R = tert-butyl)
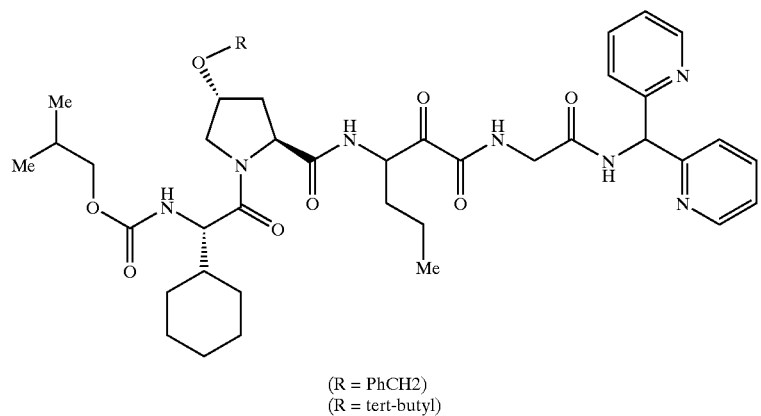
(R = PhCH2)
(R = tert-butyl)
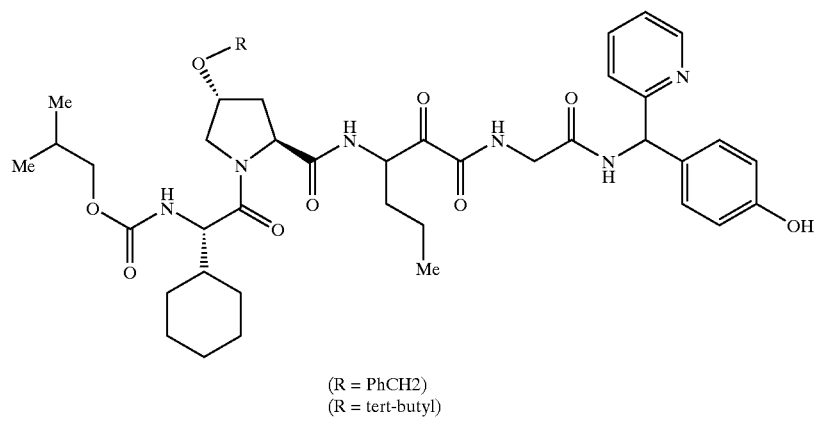
(R = PhCH2)
(R = tert-butyl)
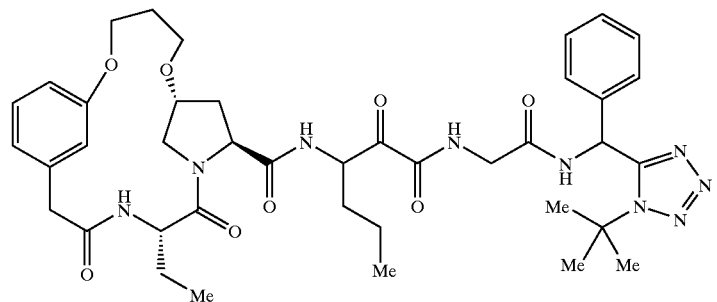

-continued

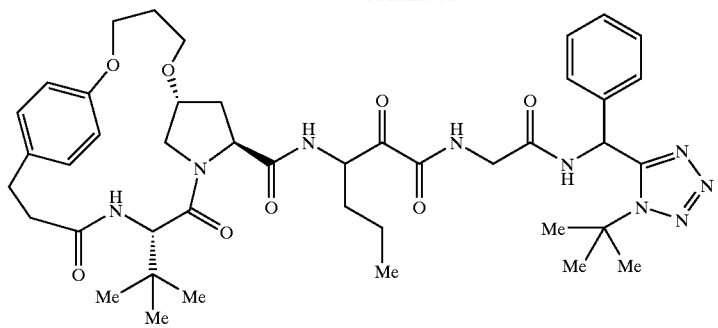

In one embodiment, the present invention discloses compounds of Formula I as inhibitors of HCV protease, especially the HCV NS3/NS4a serine protease, or a pharmaceutically acceptable derivative thereof, where the various definitions are given above.

In another embodiment, the present invention discloses compounds including enantiomers, stereoisomers, rotomers and tautomers of said compound, and pharmaceutically acceptable salts, solvates or derivatives thereof, with said compound having the general structure shown in Formula II:

Formula II

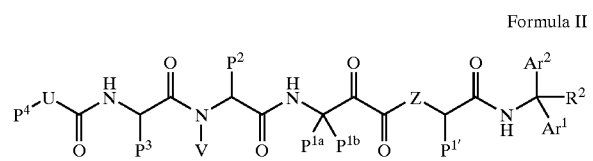

wherein:
$P^{1a}$, $P^{1b}$, $P^{1'}$, $P^2$, and $P^3$ are independently:
H, C1–C10 straight or branched chain alkyl, C2–C10 straight or branched chain alkenyl, and C3–C8 cycloalkyl, C3–C8 heterocyclic; (cycloalkyl)alkyl or (heterocyclyl)alkyl, wherein said cycloalkyl is made up of 3 to 8 carbon atoms, and zero to 6 oxygen, nitrogen, sulfur, or phosphorus atoms, and said alkyl is of 1 to 6 carbon atoms;
aryl, heteroaryl, arylalkyl, or heteroarylalkyl, wherein said alkyl is of 1 to 6 carbon atoms;
wherein said alkyl, alkenyl, cycloalkyl, heterocyclyl; (cycloalkyl)alkyl and (heterocyclyl)alkyl moieties may be optionally substituted with R", and further wherein said $P^{1a}$ and $P^{1b}$ may optionally be joined to each other to form a spirocyclic or spiroheterocyclic ring, with said spirocyclic or spiroheterocyclic ring containing zero to six oxygen, nitrogen, sulfur, or phosphorus atoms, and may be additionally optionally substituted with R";
R" is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from R'";
Z is O, NH or NR'";
R'" is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that R'" may be additionally optionally substituted with R";
$Ar^1$ and $Ar^2$ are independently selected from phenyl; 2-pyridyl, 3-pyridyl, 4-pyridyl or their corresponding N-oxides; 2-thiophenyl; 3-thiophenyl; 2-furanyl; 3-furanyl; 2-pyrrolyl; 3-pyrrolyl; 2-imidazolyl; 3(4)-imidazolyl; 3-(1, 2,4-triazolyl); 5-tetrazolyl; 2-thiazolyl; 4-thiazolyl; 2-oxazolyl; or 4-oxazolyl; either or both of which may be optionally substituted with $R^1$;

$R^1$ is H, halogen, cyano, nitro, $CF_3$, $Si(alkyl)_3$, straight-chain or branched lower alkyl, alkenyl, alkynyl, cycloalkyl, cycloalkyl-alkyl, aryl, alkylaryl, arylalkyl, heteroaryl, hydroxy, alkoxy, aryloxy, alkoxycarbonyloxy, (alkylamino) carbonyloxy, mercapto, alkylthio, arylthio, alkylsulfinyl, heterocyclylsulfinyl, arylsulfinyl, heteroarylsulfinyl, alkylsulfonyl, heterocyclylsulfonyl, arylsulfonyl, heteroarylsulfonyl, alkylcarbonyl, arylcarbonyl, carboxy, alkoxycarbonyl, aryloxycarbonyl, heteroaryloxycarbonyl, alkyaminocarbonyl, arylaminocarbonyl, amino, alkylamino, arylamino, alkylsulfonamide, arylsulfonamide, alkoxycarbonbylamino, alkylureido, or arylureido;

$P^4$ is H, linear or branched alkyl, arylalkyl or aryl;

$R^{2'}$ is H, cyano, $CF_3$, straight-chain or branched lower alkyl, alkenyl, alkynyl, cycloalkyl, cycloalkyl-alkyl, aryl, alkylaryl, arylalkyl, heteroaryl, alkylsulfonyl, arylsulfonyl, carboxy, alkoxycarbonyl, aryloxycarbonyl, alkyaminocarbonyl, or arylaminocarbonyl;

U is O, NH, $CH_2$ or CHR"; and

V is H, methyl, or lower alkyl.

In a suitable formulation in Formula II, $R^{2'}$ is selected from the group consisting of H, alkyl, alkenyl, alkoxycarbonyl, or (allylamino) carbonyl.

Advantageously in Formula II, $Ar^1$ and $Ar^2$ are independently selected from the group consisting of phenyl, 2-thiophenyl, 2-furanyl, 3-furanyl, 3(4)-imidazolyl, 3-(1,2, 4-triazolyl), 5-tetrazolyl, or 2-thiazolyl.

Preferably, $Ar^2$ is phenyl and $Ar^1$ is selected from the group consisting of 3-(1,2,4-triazolyl),5-tetrazolyl, or 2-thiazolyl.

Suitably in Formula II, $R^1$ is H, $CF_3$, $CH_3$, alkyl or alkenyl and $P^{1'}$ is either H or $CH_3$.

Advantageously, $P^{1'}$ is H such that $P^{1'}$ and the adjacent nitrogen and carbonyl moieties correspond to the residuum of glycine unit.

Suitably in Formula II, $P^{1a}$ and $P^{1b}$ is selected from the group consisting of the following moieties:

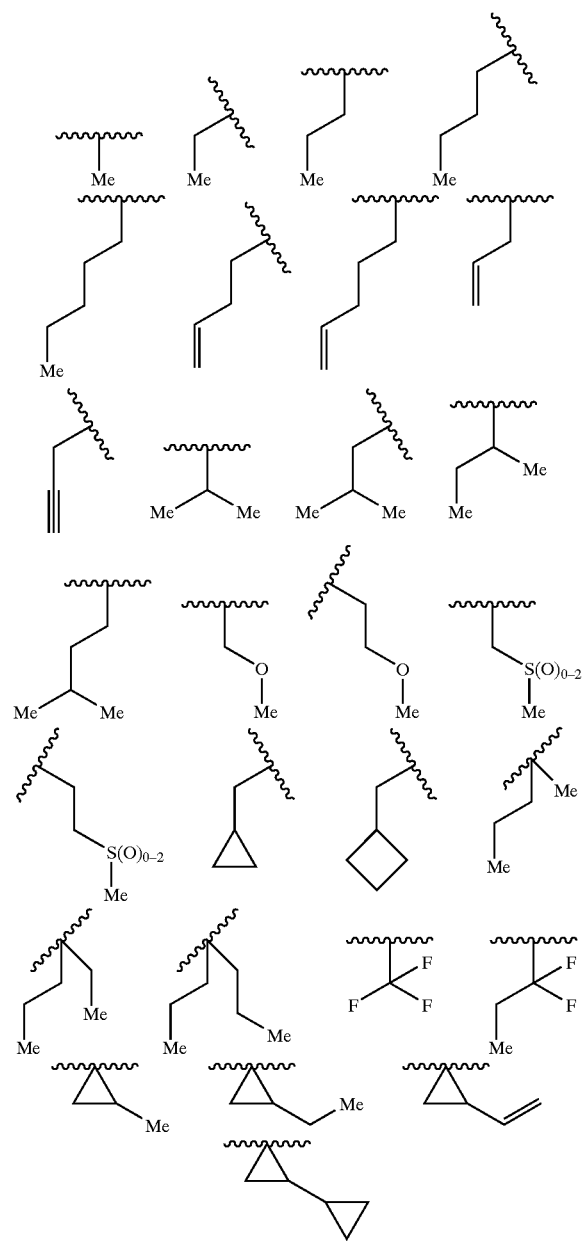
Advantageously in Formula II, $P^3$ is selected from the group consisting of:
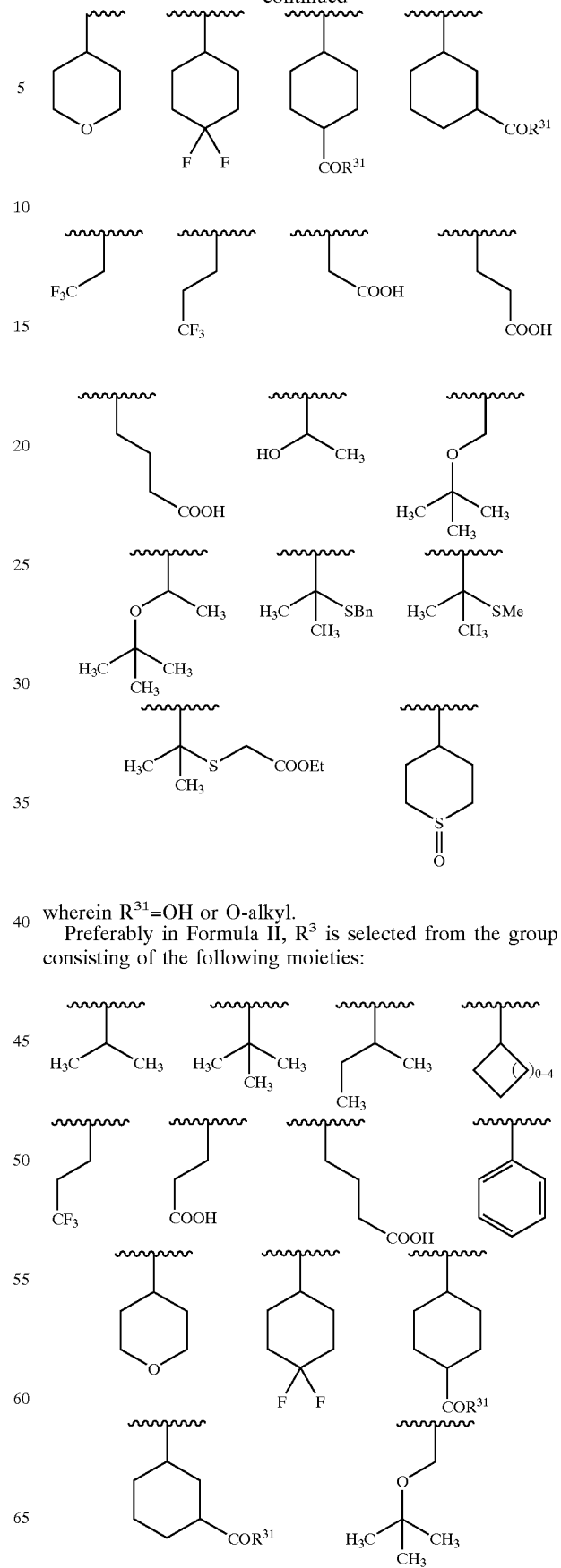
wherein $R^{31}$=OH or O-alkyl.
Preferably in Formula II, $R^3$ is selected from the group consisting of the following moieties:
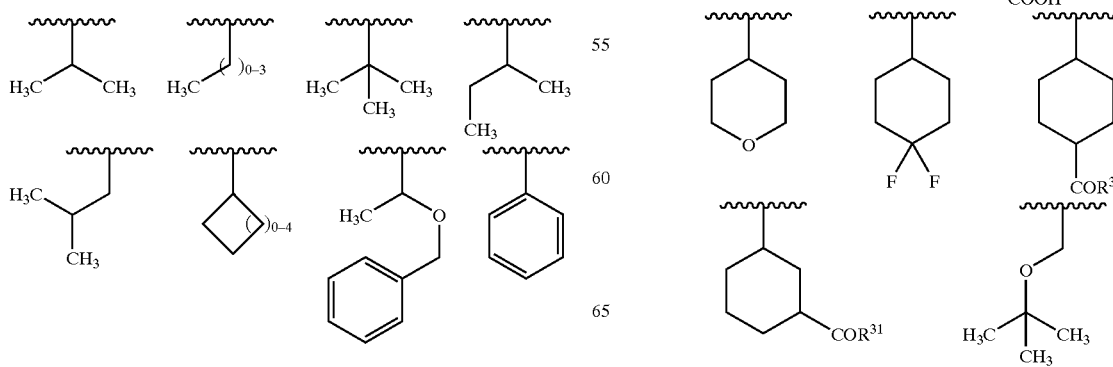

Suitably in Formula II, U is N and $P^4$ is alkyl or arylalkyl.
Preferably U is O or $CH_2$.
$P^4$ is selected from the following moieties:
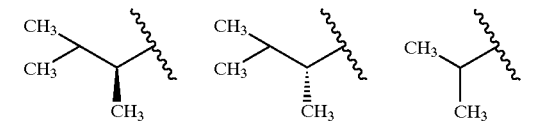
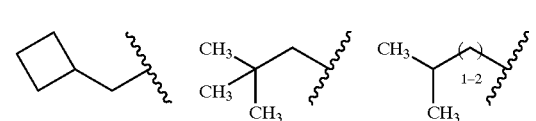
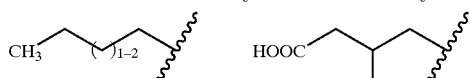
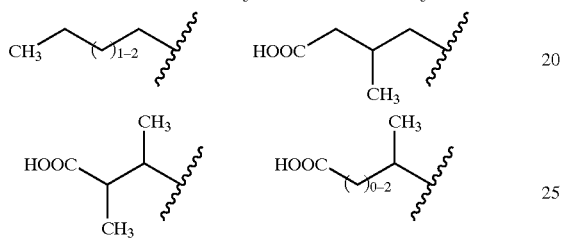
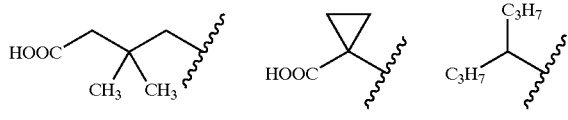
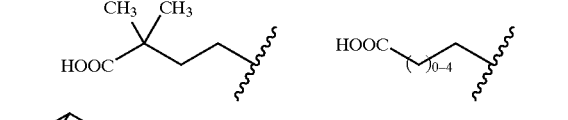
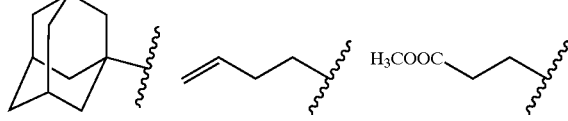
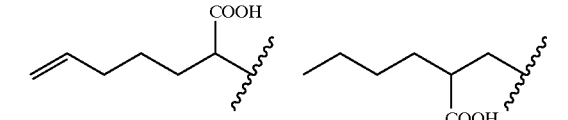
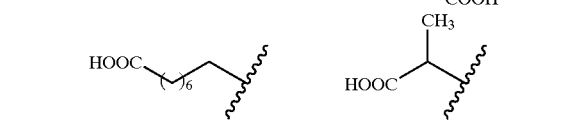
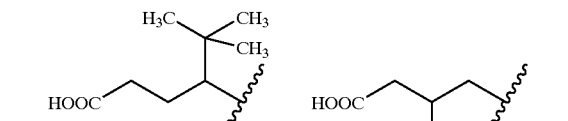
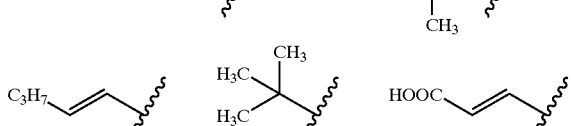
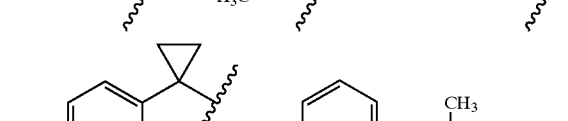
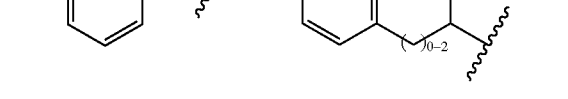
-continued
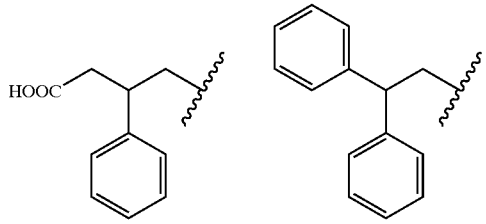
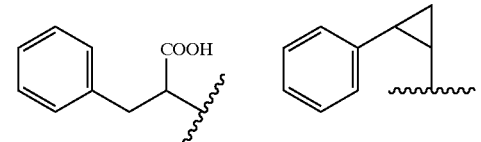
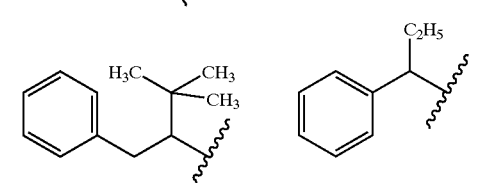
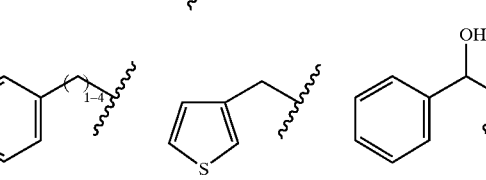
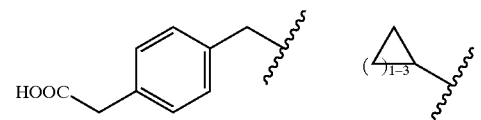
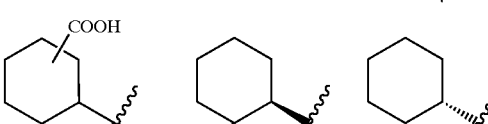
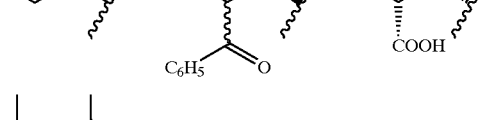
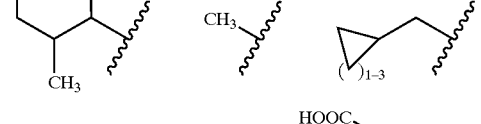
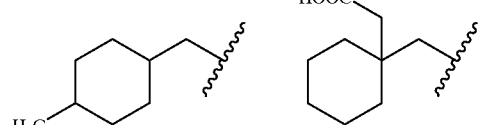
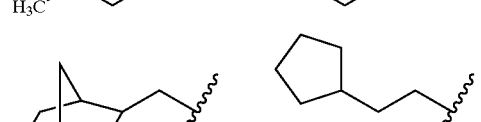
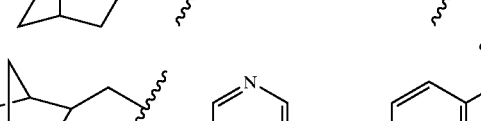
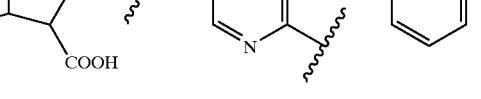

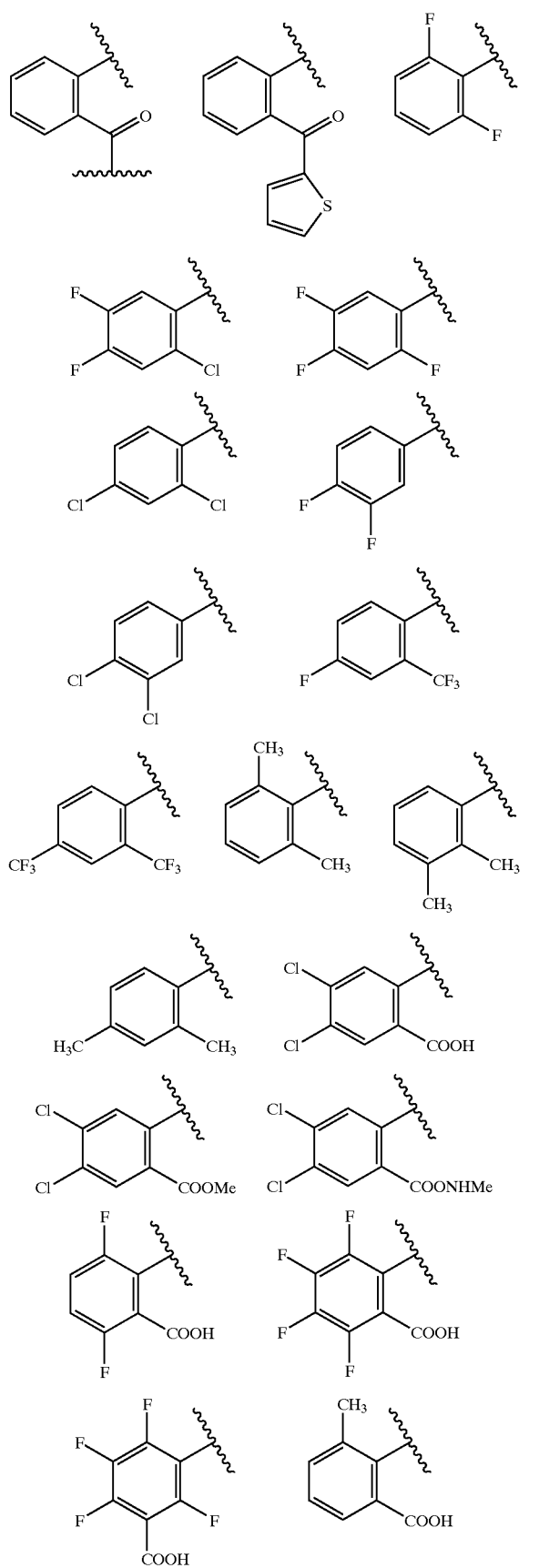

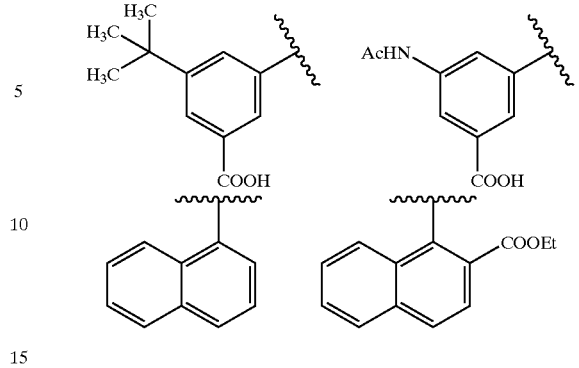

Suitably in Formula II, U is CH$_2$ and P$^4$ is phenyl or U is O and P$^4$ is selected from the group consisting of methyl, tertiary butyl, isobutyl, and 2,3-dimethylpropyl.

In Formula II, P$^2$ and P$^3$ are independently selected from the group consisting of: H, linear alkyl, branched alkyl, or arylalkyl, such that P$^2$ or P$^3$ and the adjacent nitrogen and carbonyl moieties thereto correspond to the residuum of an alpha amino acid.

Preferably, P$^3$ is selected from the following moieties:

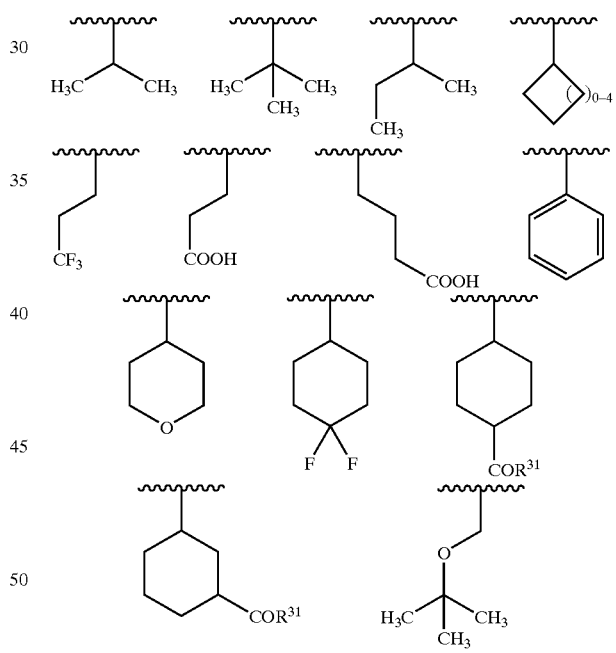

Suitably, P$^3$ is selected from the group consisting of isopropyl tertiary butyl, isobutyl and cyclohexyl substituents.

Advantageously, in Formula II, V is H.

A preferred compound of Formula II exhibiting HCV protease inhibitory activity, including enantiomers, stereoisomers and tautomers of said compound, and pharmaceutically acceptable salts or solvates of said compound, said compound being selected from the compounds of structures listed below:

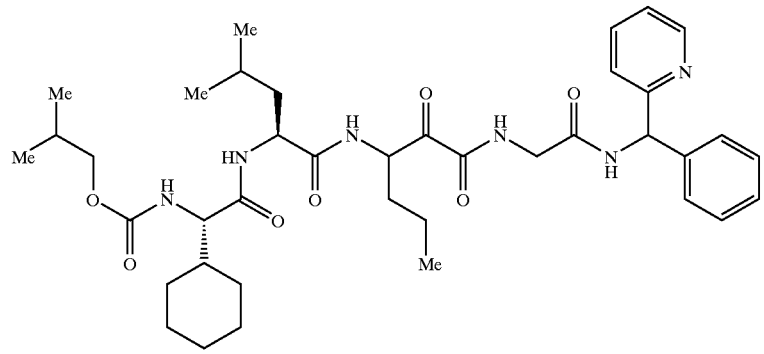
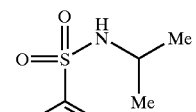
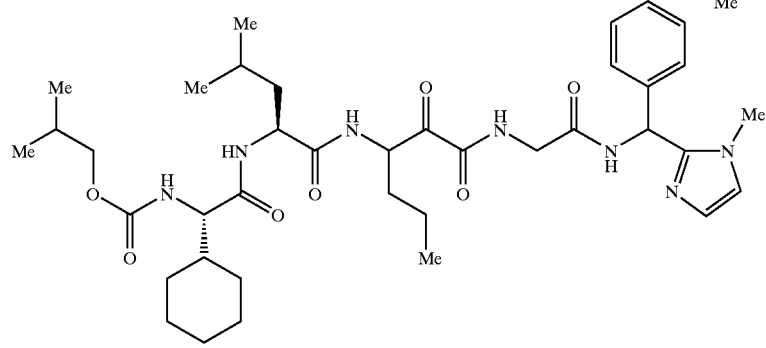
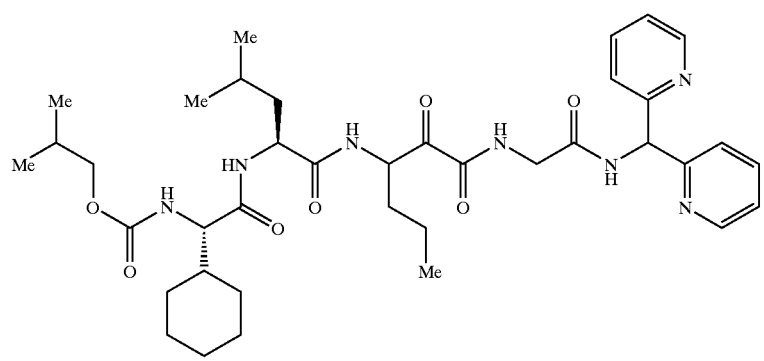
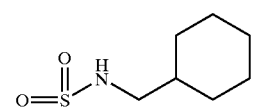
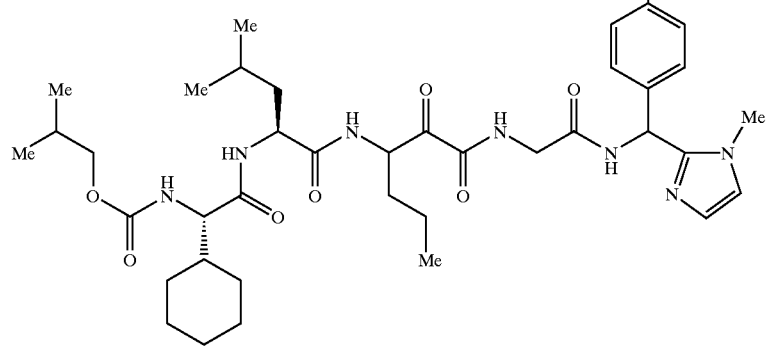

-continued

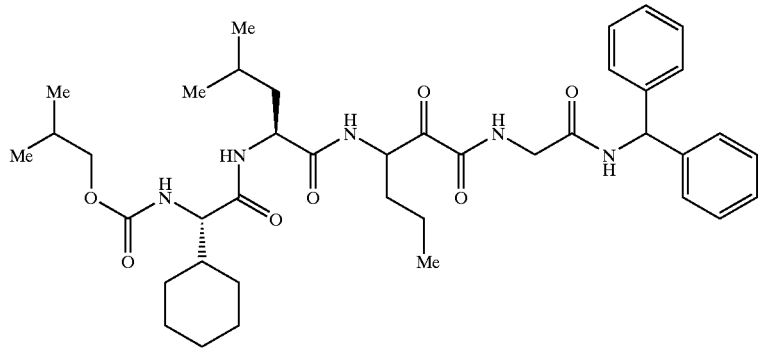

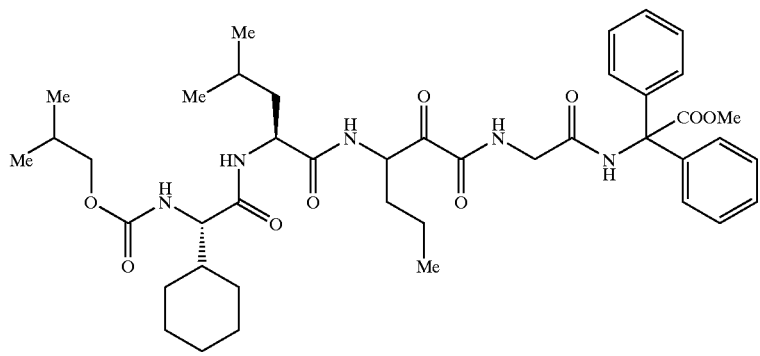

In another embodiment, the present invention discloses compounds of Formula III as inhibitors of HCV protease, especially the HCV NS3/NS4a serine protease, or a pharmaceutically acceptable derivative thereof. The compound of Formula III has the following structure:

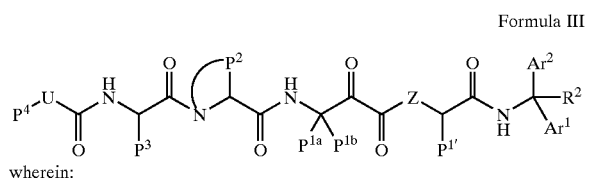

Formula III wherein:

wherein:
$P^{1a}$, $P^{1b}$, $P^{1'}$, $P^2$, and $P^3$ are independently selected from:
H, C1–C10 straight or branched chain alkyl, C2–C10 straight or branched chain alkenyl; and C3–C8 cycloalkyl, C3–C8 heterocyclic; (cycloalkyl)alkyl or (heterocyclyl)alkyl, wherein said cycloalkyl is made up of 3 to 8 carbon atoms, and zero to 6 oxygen, nitrogen, sulfur, or phosphorus atoms, and said alkyl is of 1 to 6 carbon atoms;
aryl, heteroaryl, arylalkyl, or heteroarylalkyl, wherein said alkyl is of 1 to 6 carbon atoms;
wherein said alkyl, alkenyl, cycloalkyl, heterocyclyl; (cycloalkyl)alkyl and (heterocyclyl)alkyl moieties may be optionally substituted with R", and further wherein said $P^{1a}$ and $P^{1b}$ may optionally be joined to each other to form a spirocyclic or spiroheterocyclic ring, with said spirocyclic or spiroheterocyclic ring containing zero to six oxygen, nitrogen, sulfur, or phosphorus atoms, and may be additionally optionally substituted with R";
R" is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from R";

Z is O, NH or NR'";

R'" is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that R'" may be additionally optionally substituted with R";

$Ar^1$ and $Ar^2$ are independently selected from phenyl; 2-pyridyl, 3-pyridyl, 4-pyridyl or their corresponding N-oxides; 2-thiophenyl; 3-thiophenyl; 2-furanyl; 3-furanyl; 2-pyrrolyl; 3-pyrrolyl; 2-imidazolyl; 3(4)-imidazolyl; 3-(1, 2,4-triazolyl); 5-tetrazolyl; 2-thiazolyl; 4-thiazolyl; 2-oxazolyl; or 4-oxazolyl; either or both of which may be optionally substituted with $R^1$;

$R^1$ is H, halogen, cyano, nitro, $CF_3$, Si(alkyl)$_3$, straight-chain or branched lower alkyl, alkenyl, alkynyl, cycloalkyl, cycloalkyl-alkyl, aryl, alkylaryl, arylalkyl, heteroaryl, hydroxy, alkoxy, aryloxy, alkoxycarbonyloxy, (alkylamino)carbonyloxy, mercapto, alkylthio, arylthio, alkylsulfinyl, heterocyclylsulfinyl, arylsulfinyl, heteroarylsulfinyl, alkylsulfonyl, heterocyclylsulfonyl, arylsulfonyl, heteroarylsulfonyl, alkylcarbonyl, arylcarbonyl, carboxy, alkoxycarbonyl, aryloxycarbonyl, heteroaryloxycarbonyl, alkyaminocarbonyl, arylaminocarbonyl, amino, alkylamino, arylamino, alkylsulfonamido, arylsulfonamido, alkoxycarbonbylamino, alkylureido, or arylureido;

$P^4$ is H, linear or branched alkyl, arylalkyl or aryl;

$R^{2'}$ is H, cyano, $CF_3$, straight-chain or branched lower alkyl, alkenyl, alkynyl, cycloalkyl, cycloalkyl-alkyl, aryl, alkylaryl, arylalkyl, heteroaryl, alkylsulfonyl, arylsulfonyl, carboxy, alkoxycarbonyl, aryloxycarbonyl, alkyaminocarbonyl, or arylaminocarbonyl;

U is O, NH, CH$_2$ or CHR";

and

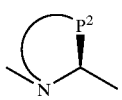   IV where moiety IV indicates a cyclic ring structure, with the proviso that said cyclic ring structure does not contain a carbonyl group as part of the cyclic ring.

Preferably moiety IV is a five- or six-membered ring.

Advantageously, the moiety IV forms a structural unit selected from the group consisting of:

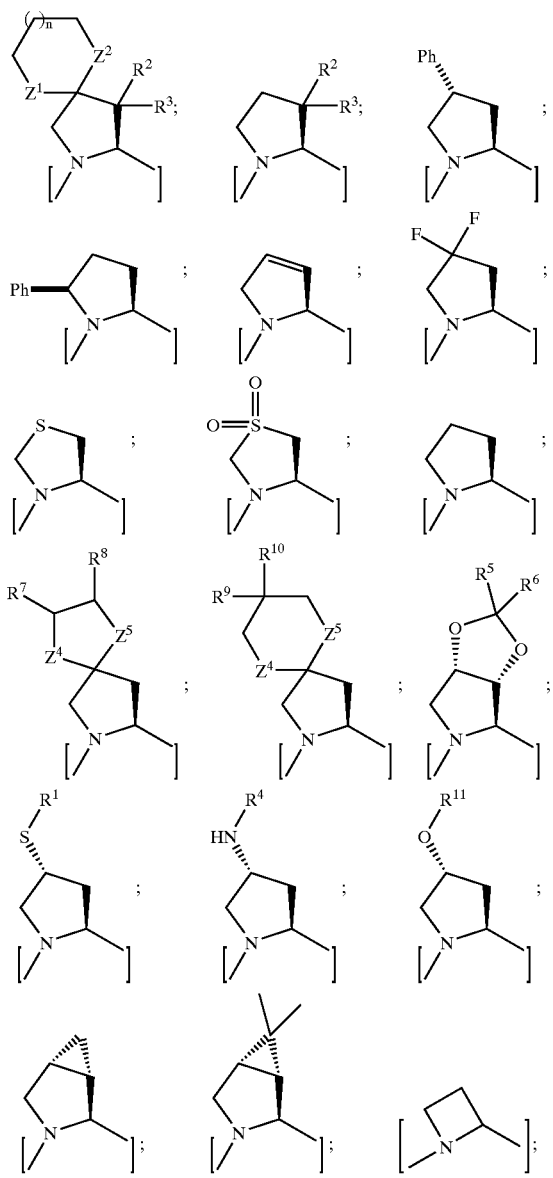

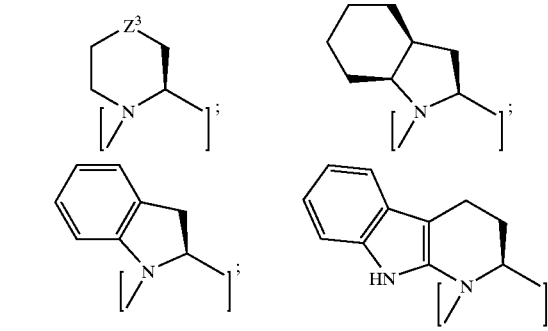

wherein n=0, 1, 2, or 3; and

R$^2$=R$^3$=H; R$^2$=C$_1$ to C$_6$ straight chainalkyl or cycloalkyl; R$^3$=H

R$^4$=COAlkyl (straight chain or cyclic, C$_1$ to C$_6$); COAryl; COOAlkyl; COOAryl R$^5$=H; R$^6$=Alkyl (C$_1$ to C$_3$); R$^6$=H; R$^5$=Alkyl (C$_1$ to C$_3$)

R$^7$=H; R$^8$=Alkyl (C$_1$ to C$_3$), CH$_2$OH; R$^8$=H; R$^7$=Alkyl (C$_1$ to C$_3$), CH$_2$OH;

R$^9$=R$^{10}$=Alkyl (C$_1$ to C$_3$); R$^9$=H, R$^{10}$=Alkyl (C$_1$ to C$_3$), COOMe, COOH, CH$_2$OH;

R$^{10}$=H, R$^9$=Alkyl (C$_1$ to C$_3$), COOMe, COOH, CH$_2$OH;

R$^{11}$=Alkyl (C$_1$ to C$_6$ straight chain, branched or cyclic), CH$_2$Aryl (may be substituted)

X$^1$=H, Alkyl (C$_1$ to C$_4$, branched or straight chain); CH$_2$Aryl (substituted or unsubstituted)

Z$^1$=Z$^2$=S, O; Z$^1$=S, Z$^2$=O; Z$^1$=O, Z$^2$=S; Z$^1$=CH$_2$, Z$^2$=O; Z$^1$-O, Z$^2$=CH$_2$;

Z$^1$=S, Z$^2$=CH$_2$; Z$^1$=CH$_2$, Z$^2$=S

Z$^3$=CH$_2$, S, SO$_2$, NH, NR$^4$

Z$^4$=Z$^5$=S, O

Advantageously, the cyclic ring moiety is

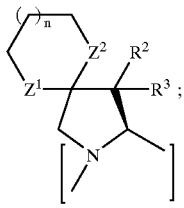

wherein Z$^1$ and Z$^2$ are S, R$^2$ and R$^3$ are H and n=1 or 2.

Suitably for the compound of Formula III, R$^{2'}$ is selected from the group consisting of H, alkyl, alkenyl, alkoxycarbonyl, or (allylamino) carbonyl and Ar$^1$ and Ar$^2$ are independently selected from the group consisting of phenyl, 2-thiophenyl, 2-furanyl, 3-furanyl, 3(4)-imidazolyl, 3-(1,2,4-triazolyl), 5-tetrazolyl, or 2-thiazolyl.

Advantageously, Ar$^2$ is phenyl and Ar$^1$ is selected from the group consisting of 3-(1,2,4-triazolyl),5-tetrazolyl, or 2-thiazolyl.

The compound of Formula III wherein in moiety IV, R$^1$ is H, CF$_3$, CH$_3$, alkyl or alkenyl and P$^{1'}$ is selected from the group consisting of H, F or CH$_3$. In another embodiment, P$^{1'}$ is H such that P$^{1'}$ and the adjacent nitrogen and carbonyl moieties correspond to the residuum of glycine unit.

The compound of Formula III, wherein P$^{1a}$ and P$^{1b}$ is selected from the group consisting of the following moieties:

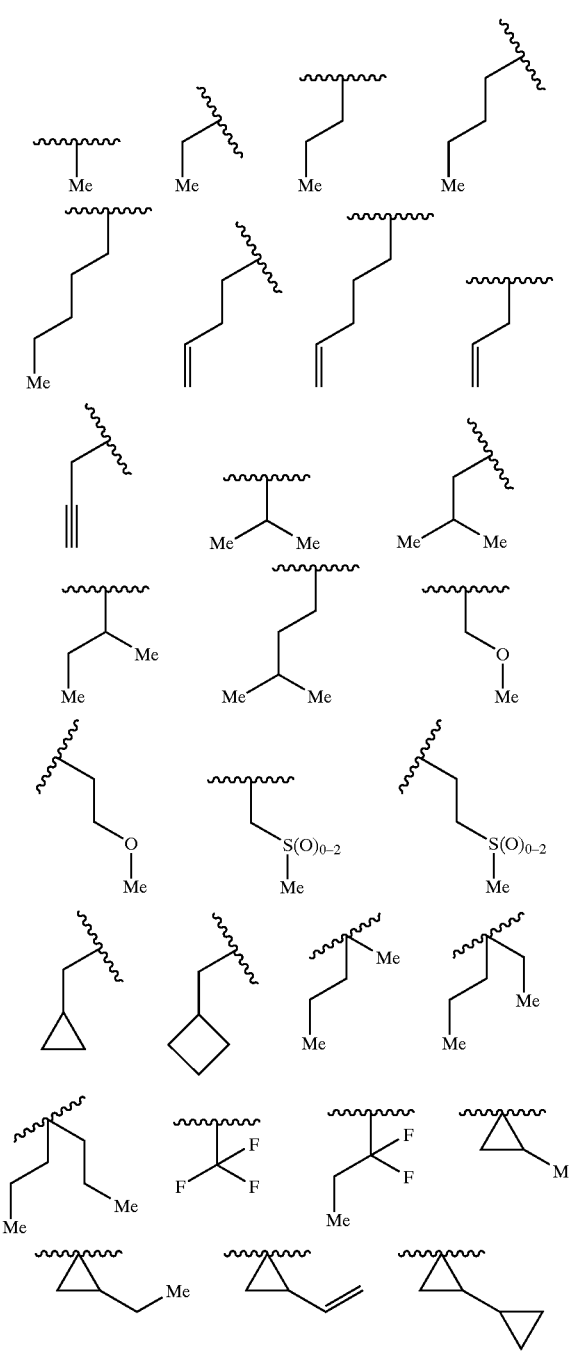
and P³ is selected from the group consisting of:
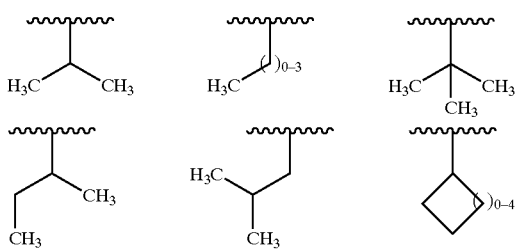
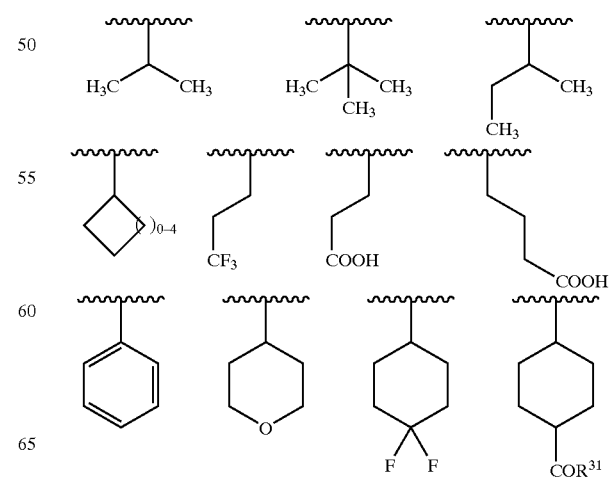
wherein R³¹=OH or O-alkyl.
The compound of Formula III wherein moiety IV, R³ is selected from the group consisting of the following moieties:

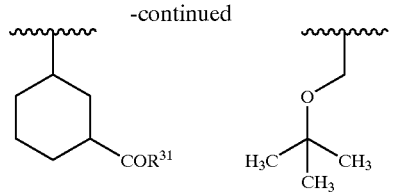
The compound of Formula III wherein moiety U is O or CH$_2$.
The compound of Formula III wherein in moiety IV, U is NH or O, and P$^4$ is alkyl or arylalkyl.
Advantageously moiety IV of Formula III comprises P$^4$ selected from the following moieties:
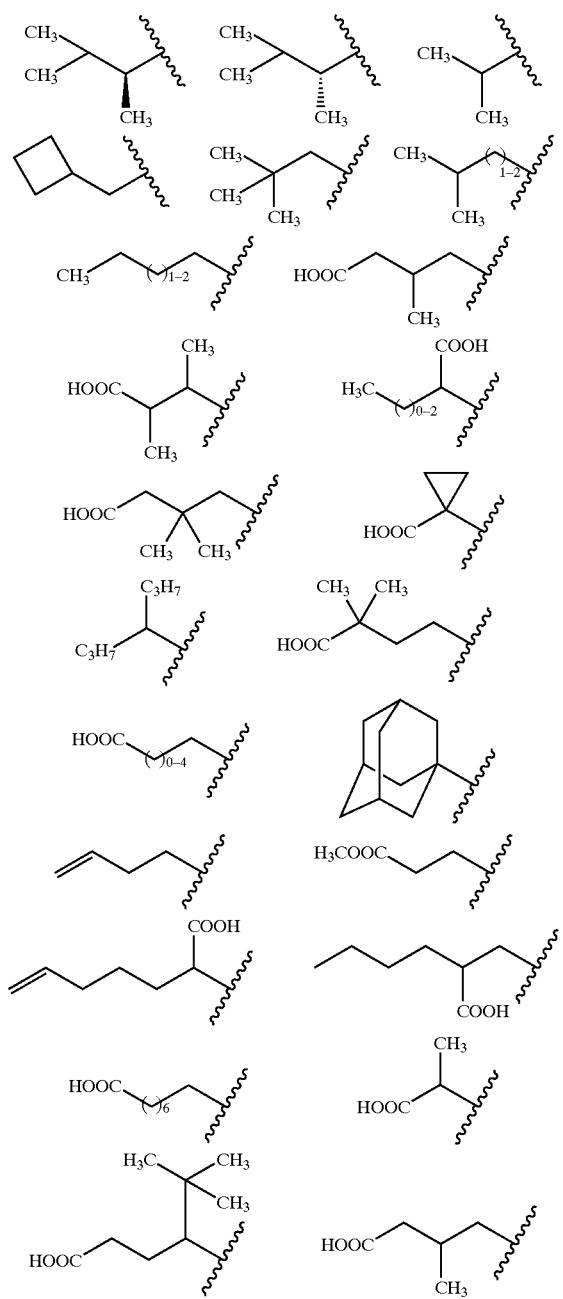
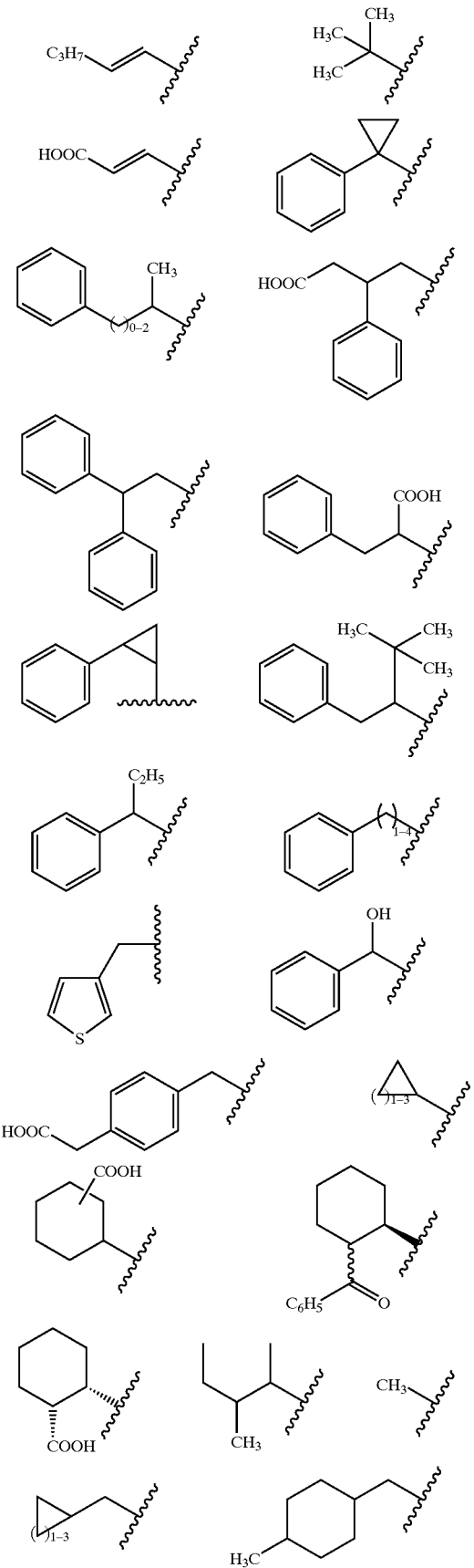

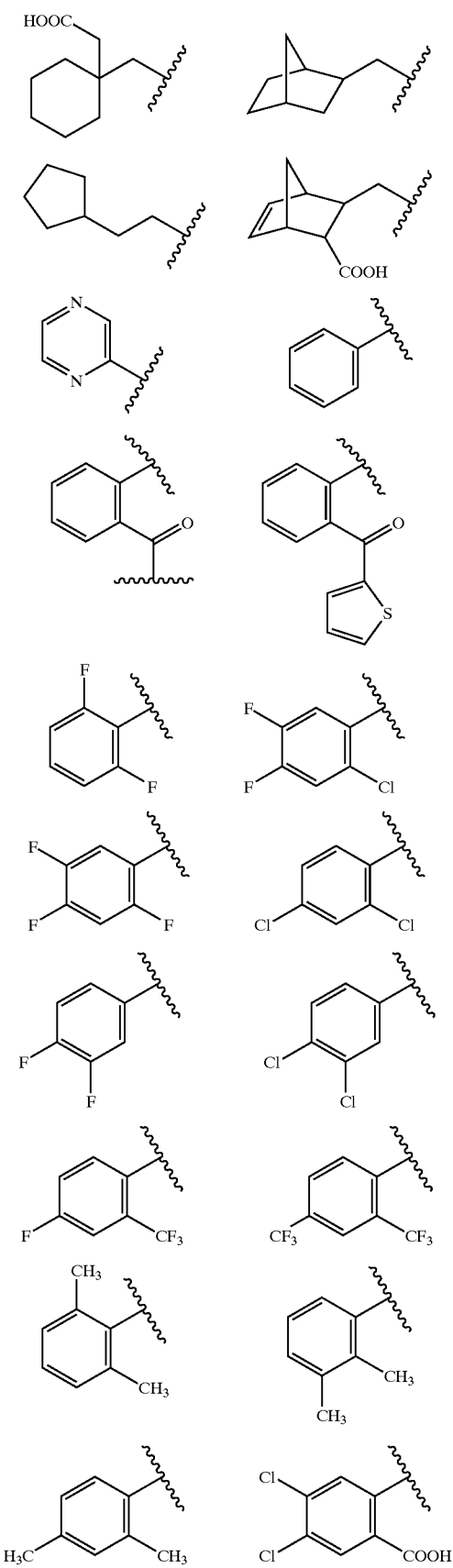
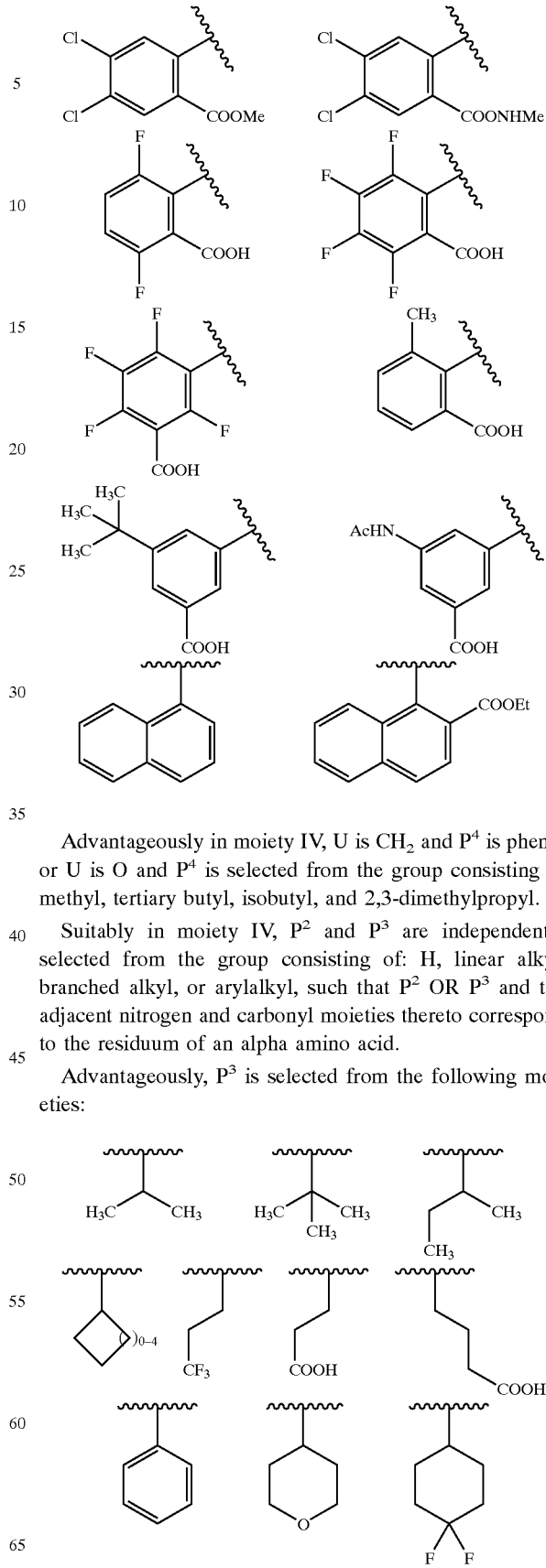

Advantageously in moiety IV, U is $CH_2$ and $P^4$ is phenyl or U is O and $P^4$ is selected from the group consisting of methyl, tertiary butyl, isobutyl, and 2,3-dimethylpropyl.

Suitably in moiety IV, $P^2$ and $P^3$ are independently selected from the group consisting of: H, linear alkyl, branched alkyl, or arylalkyl, such that $P^2$ OR $P^3$ and the adjacent nitrogen and carbonyl moieties thereto correspond to the residuum of an alpha amino acid.

Advantageously, $P^3$ is selected from the following moieties:

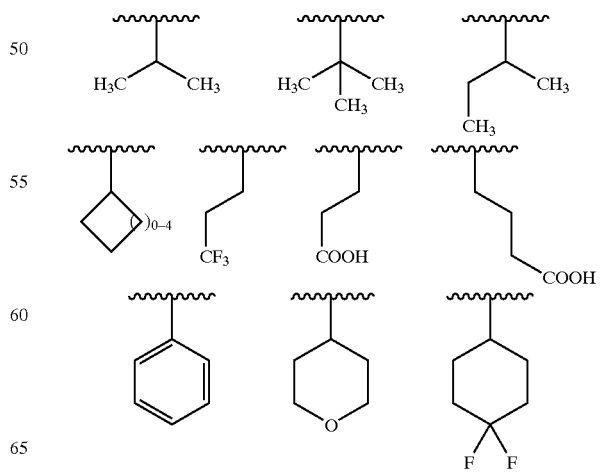

33
-continued
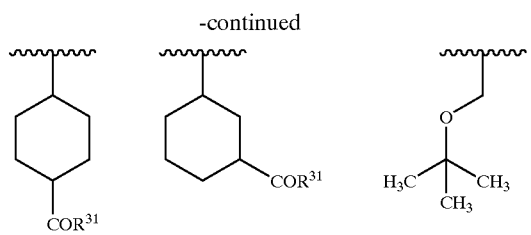
34
Preferably, P³ is selected from the group consisting of isopropyl, tertiary butyl, isobutyl and cyclohexyl substituents.
The compound according to Formula III, wherein said compound is selected from the group consisting of:
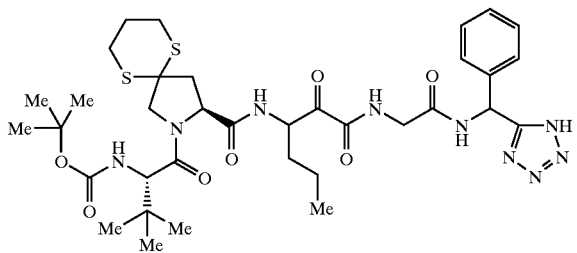
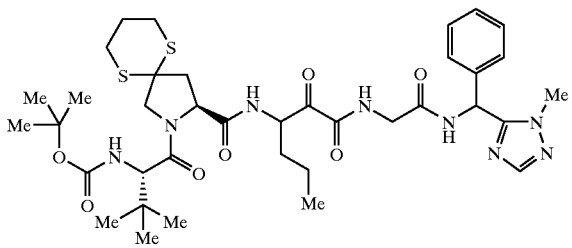
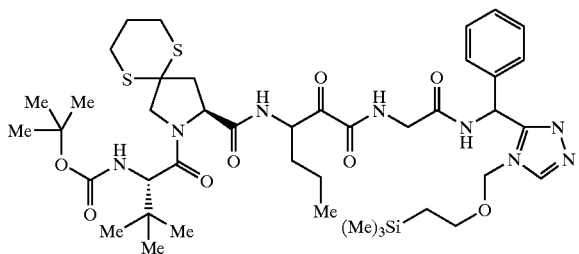
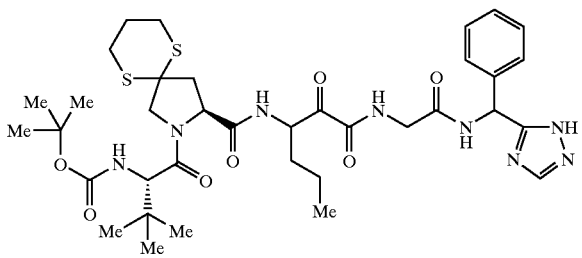
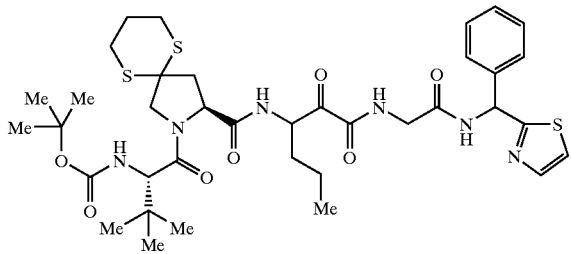
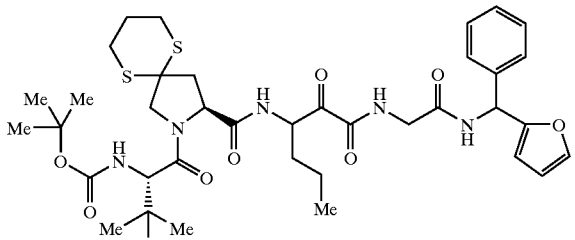
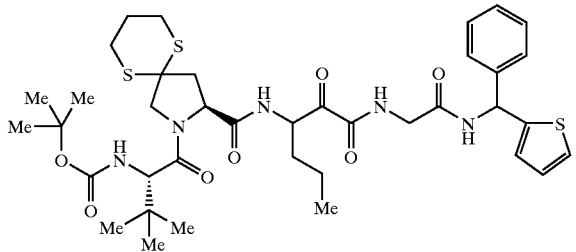
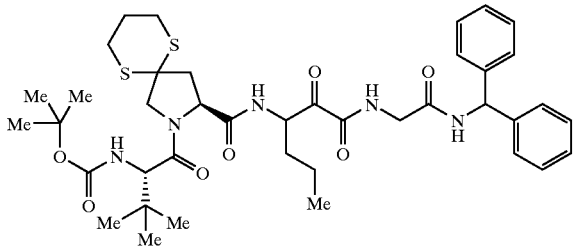
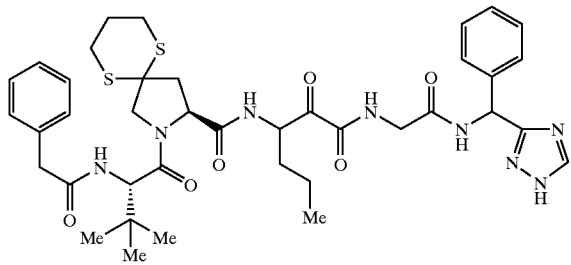
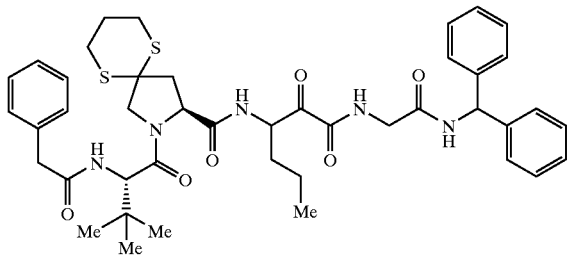

35
36
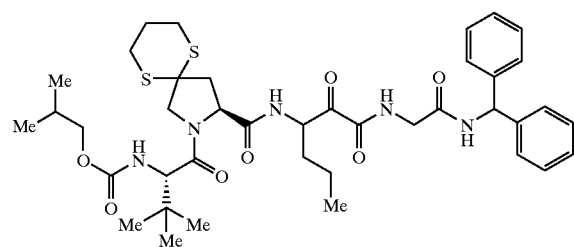
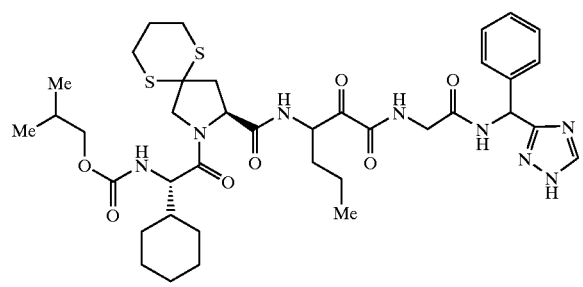
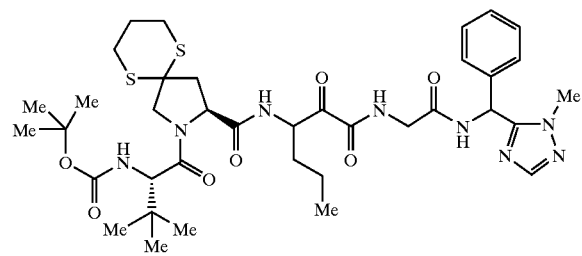
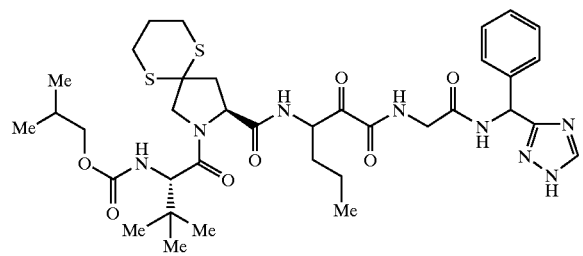
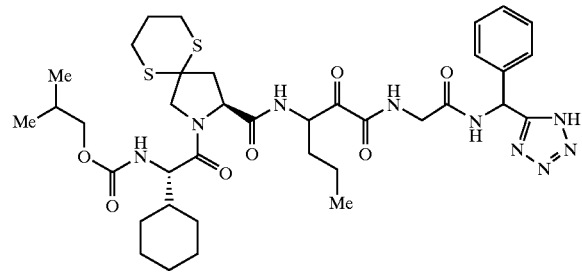
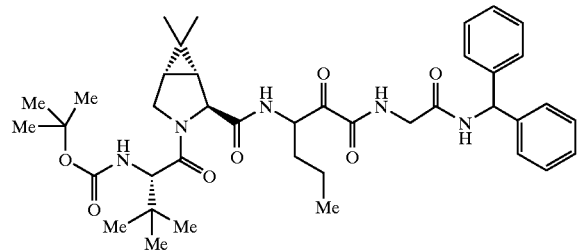
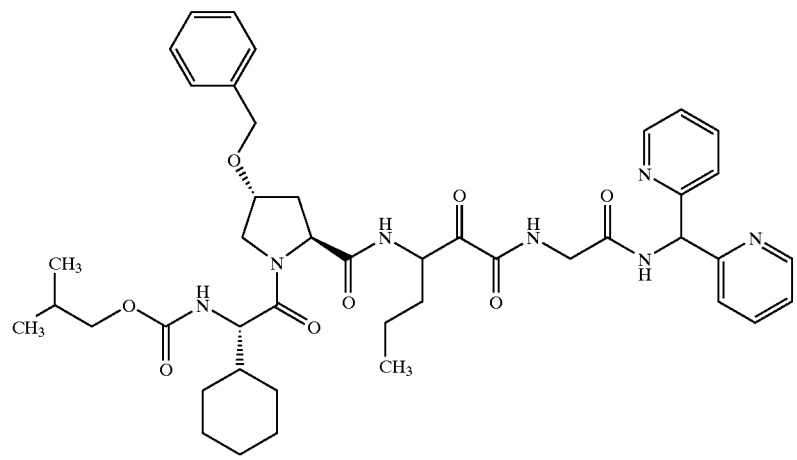
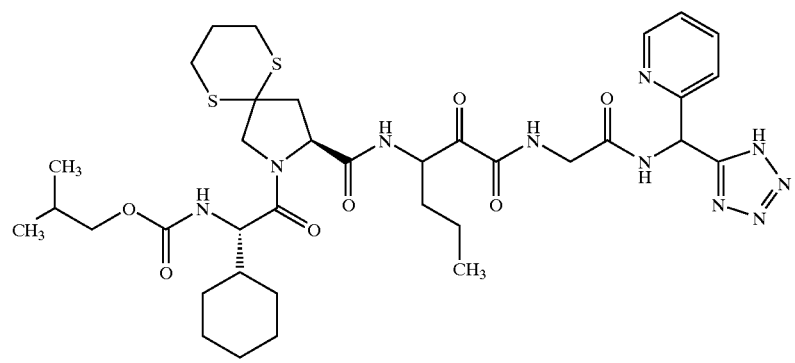

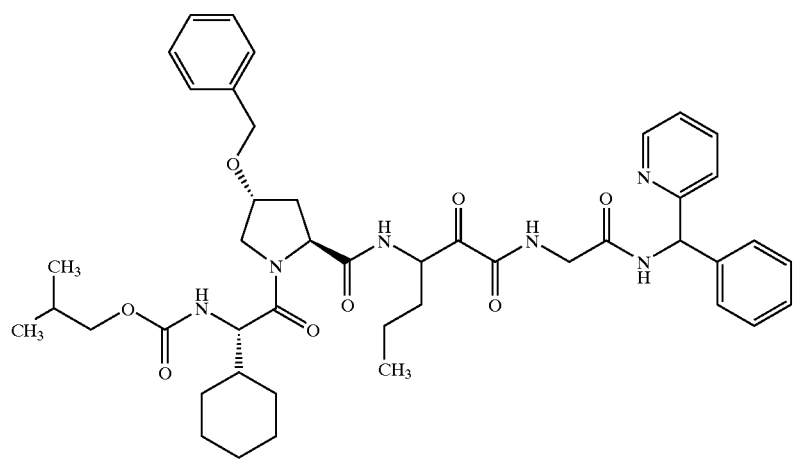
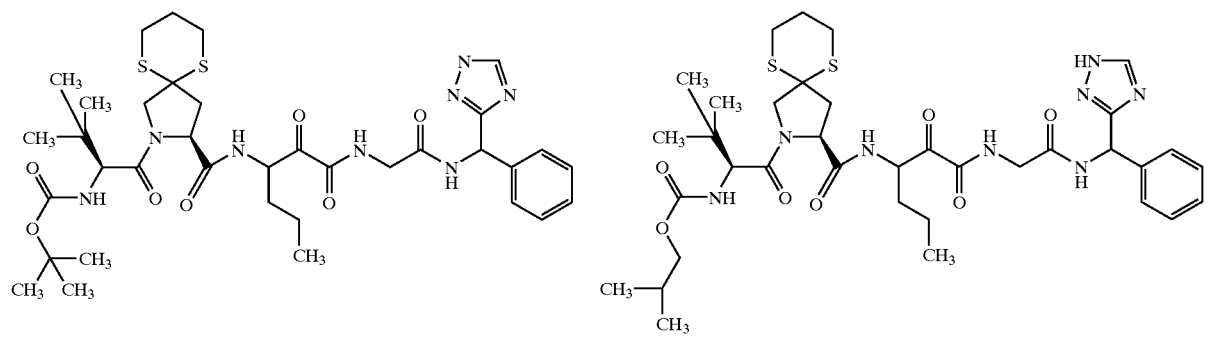
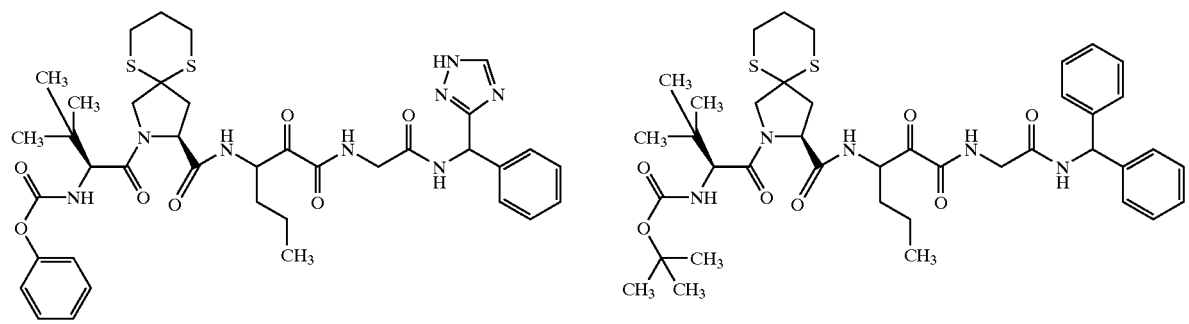
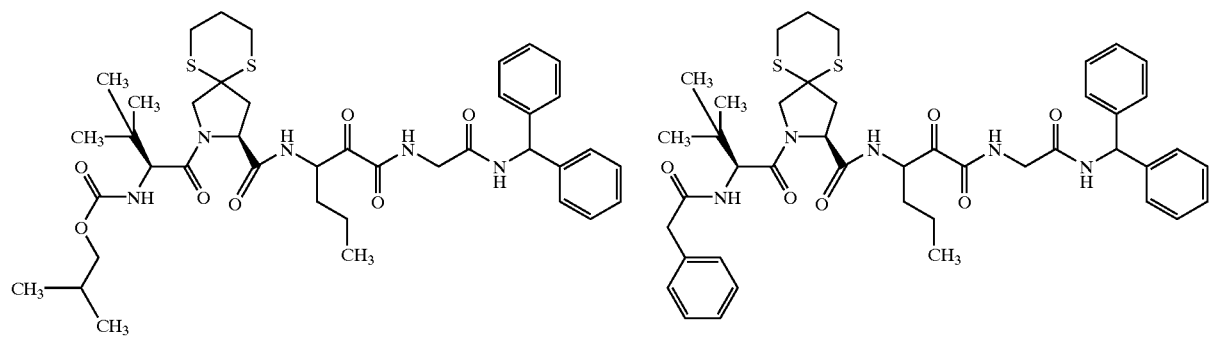

-continued
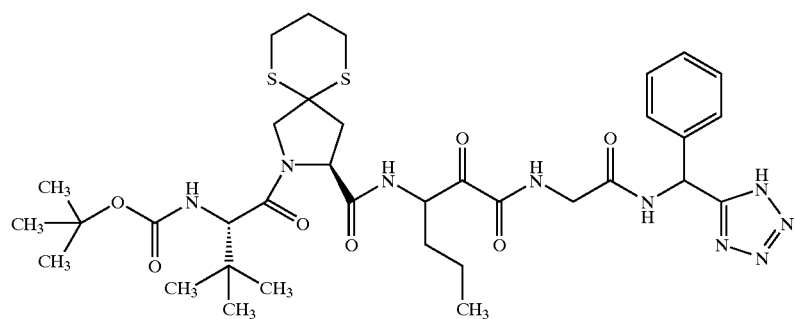
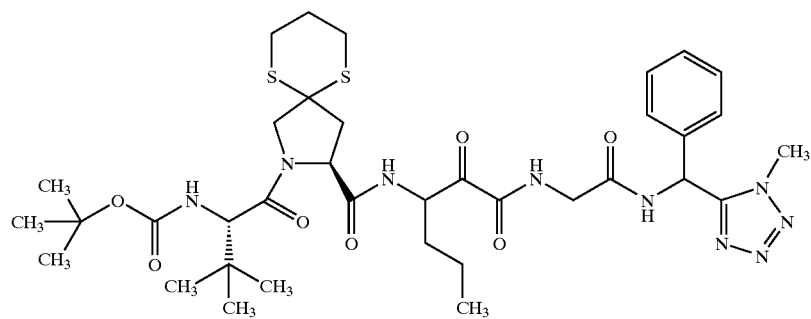
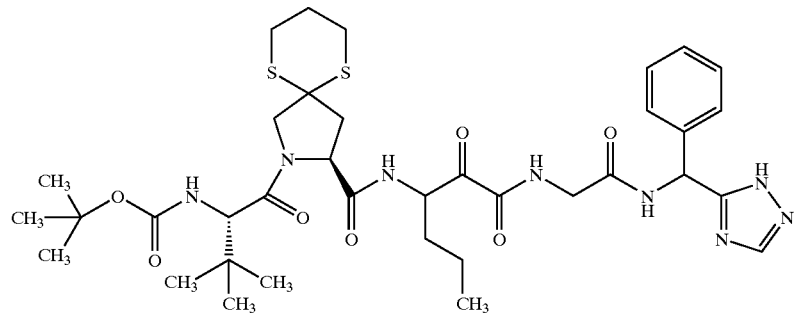
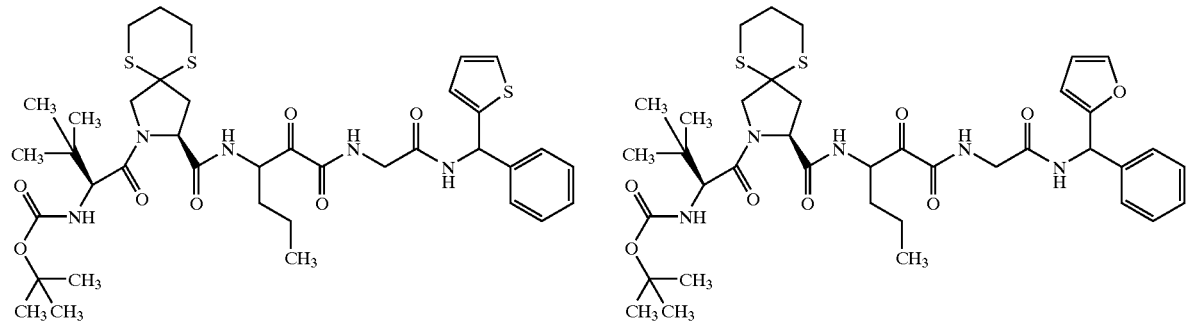
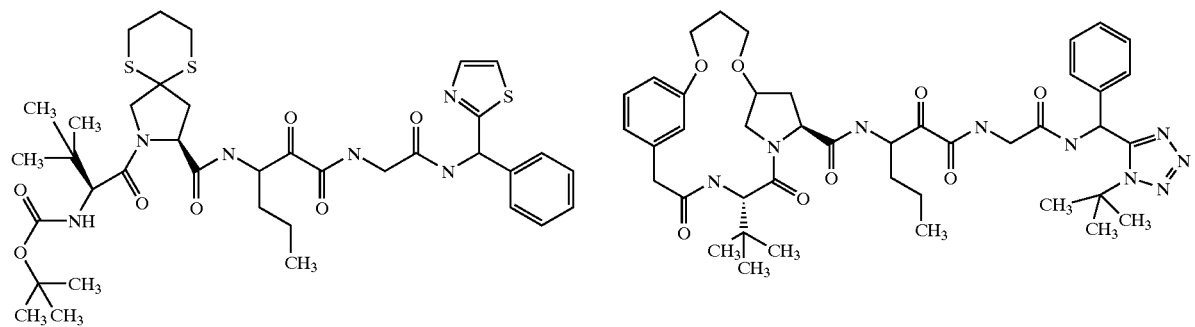

The following description of suitable moieties is applicable for compounds of Formulas I, II and III:
The following moieties are suitable P¹ moieties:
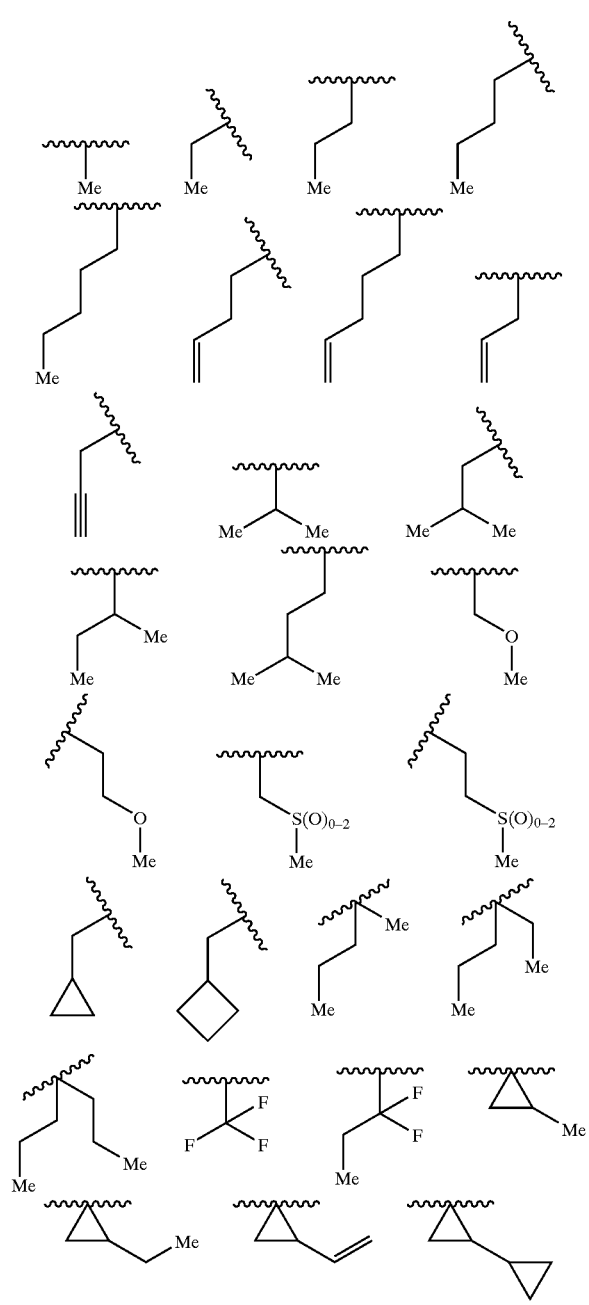
Also, the following moieties are suitable P³ moieties:
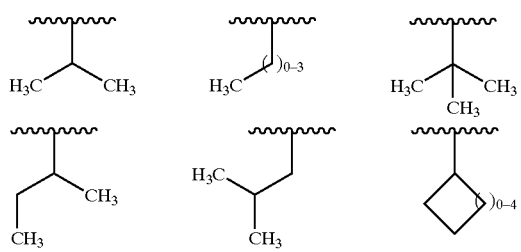
-continued
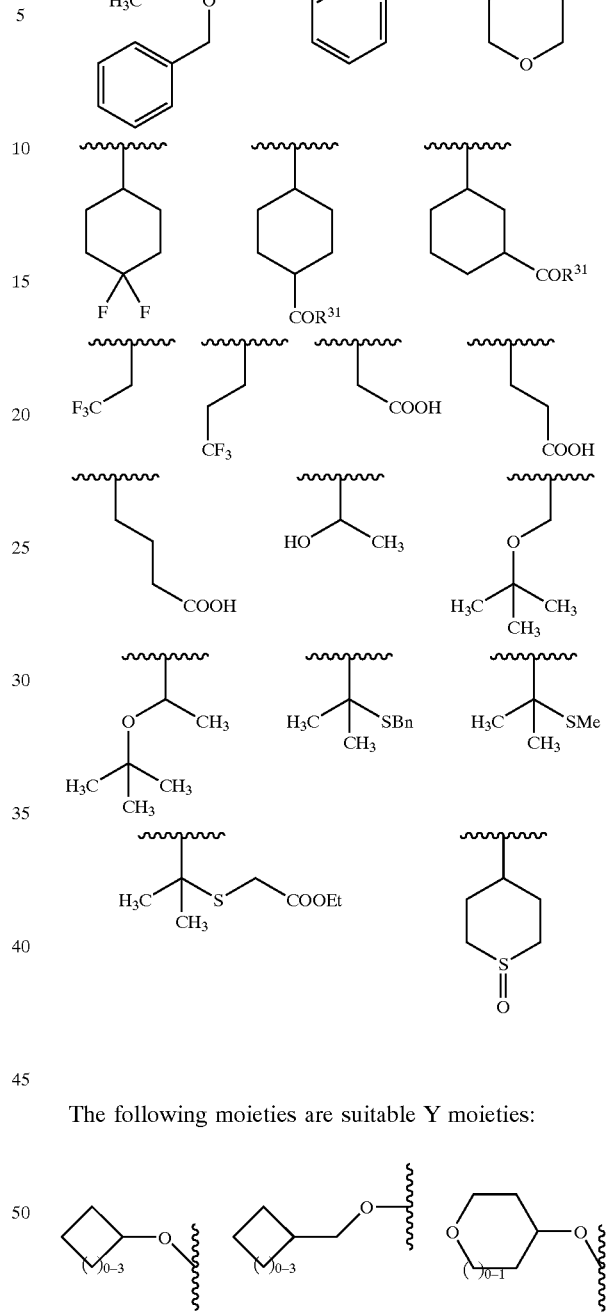
The following moieties are suitable Y moieties:
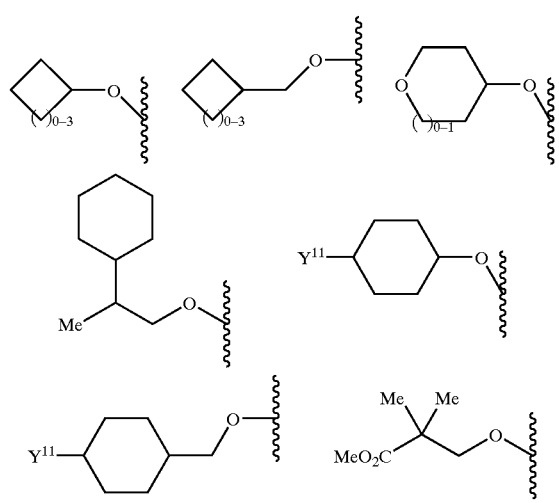

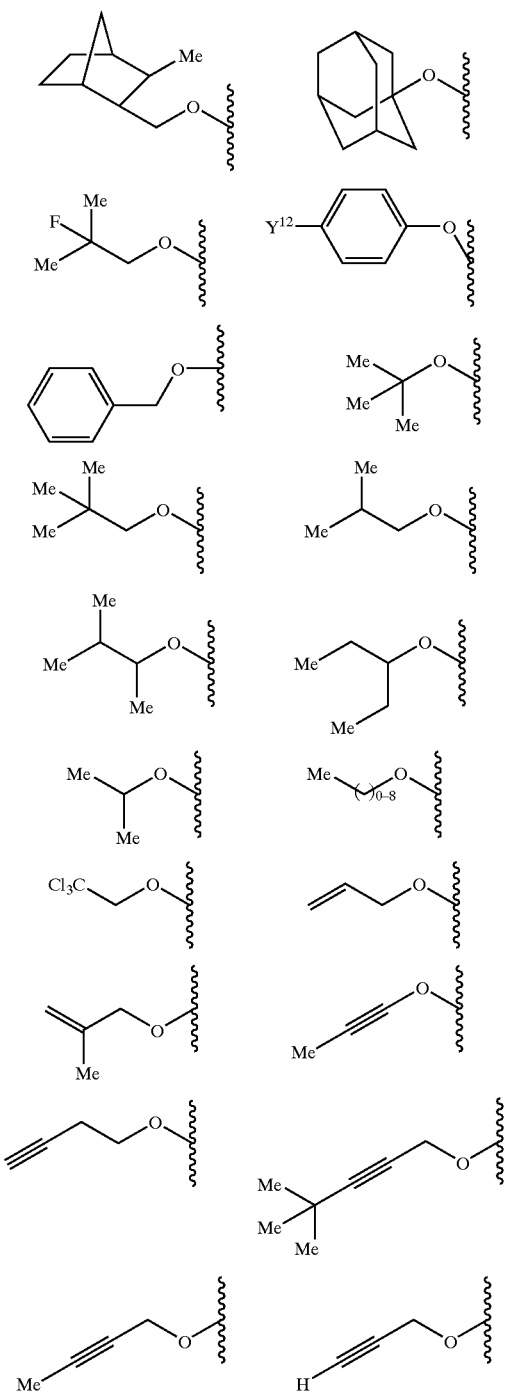

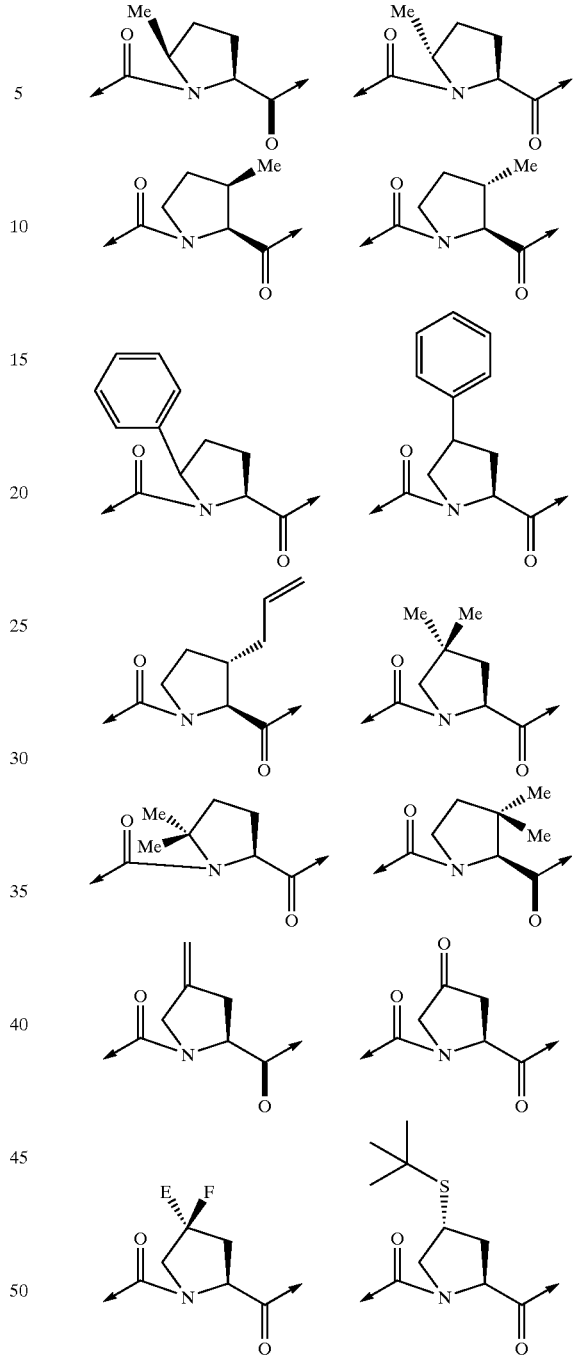

The following moieties are suitable V-P² moieties:

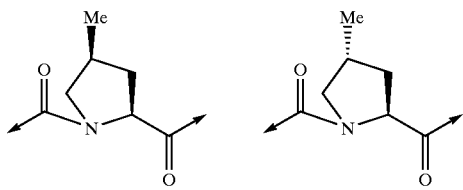

Depending upon their structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, $NH_4OH$, tetraalkylammonium hydroxide, and the like.

In another embodiment, this invention provides pharmaceutical compositions comprising the inventive peptides as an active ingredient. The pharmaceutical compositions generally additionally comprise a pharmaceutically acceptable carrier diluent, excipient or carrier (described below and collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose.

The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

As stated earlier, the invention includes tautomers, rotamers, enantiomers and other stereoisomers of the compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Representative illustrative procedures are outlined in the following reaction schemes. It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

Abbreviations which are used in the descriptions of the schemes, preparations and the examples that follow are:

THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarboxyl)dipiperidine
DEAD: Diethylazodicarboxylate
MeOH: Methanol
EtOH: Ethanol
Et$_2$O: Diethyl ether
PyBrOP: Bromo-tris-pyrrolidinophosphonium hexafluorophosphate
Bn: Bzl:Benzyl
Boc: tert-Butyloxycarbonyl
Cbz: Benzyloxycarbonyl
Ts: p-toluenesulfonyl
Me: Methyl
Bs: p-bromobenzenesulfonyl DCC: dicyclohexylcarbodiimide
DMSO: dimethylsulfoxide
SEM: (trimethylsilyl)ethoxymethyl
TEMPO: 2,2,6,6-tetramethyl-1-piperidinyloxy free radical
HATU: O-(7-azabenzotriazol-1-yl)-N,N,N',N'-tetramethyluronium General Preparative Schemes The following schemes describe generally methods of synthesis of the intermediates and the inventive diaryl peptides of the present invention.

SCHEME 1

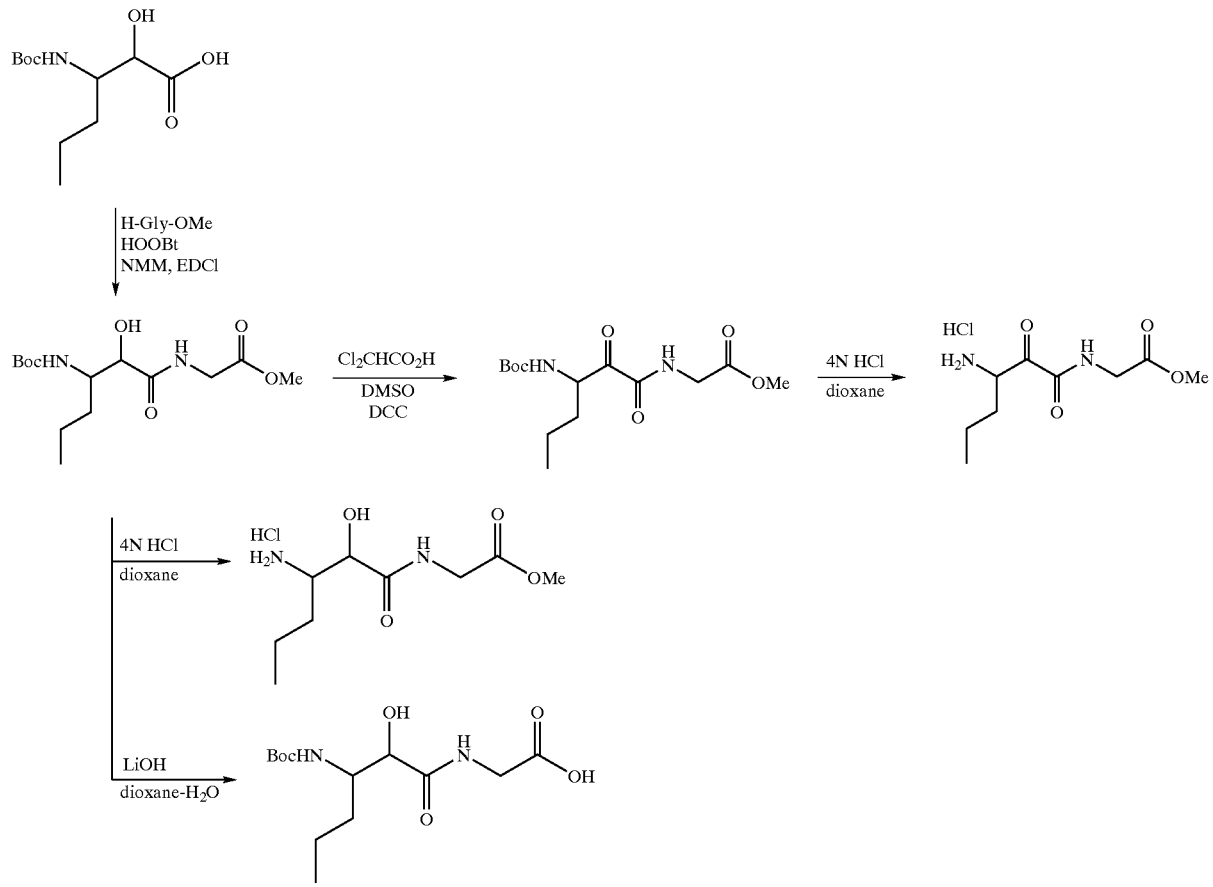

SCHEME 2

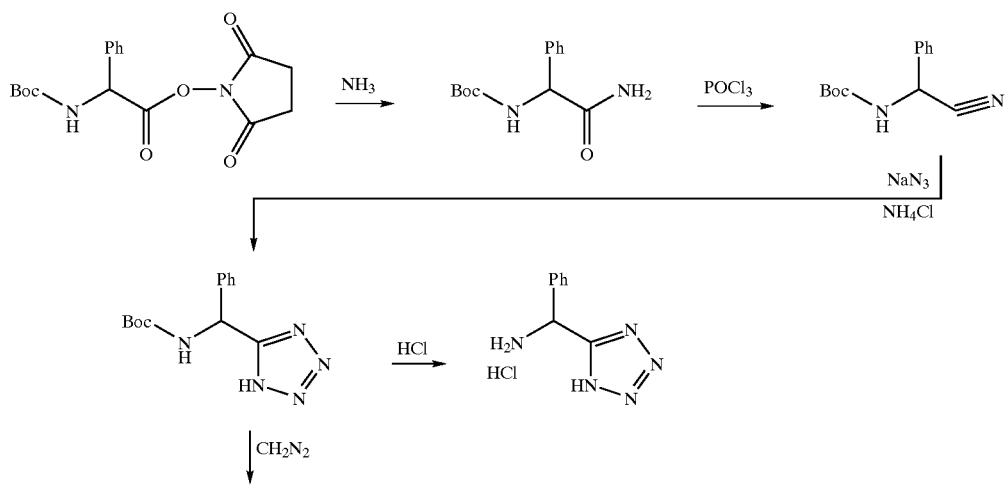

51
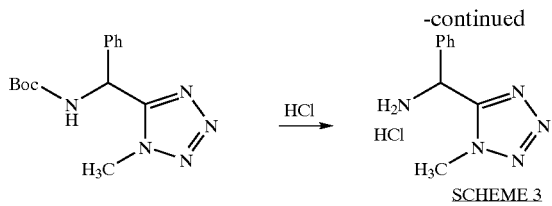
SCHEME 3
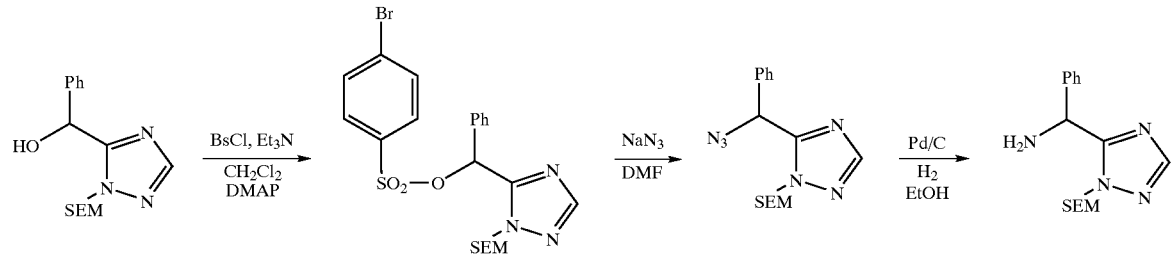
SCHEME 4
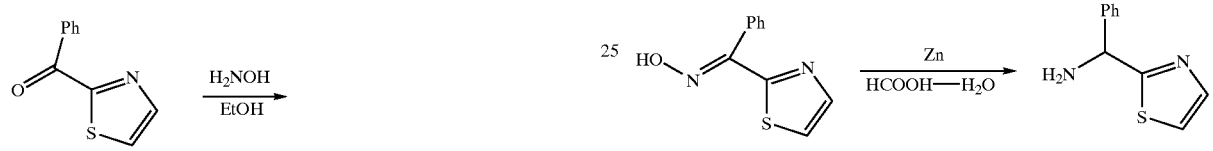
SCHEME 5
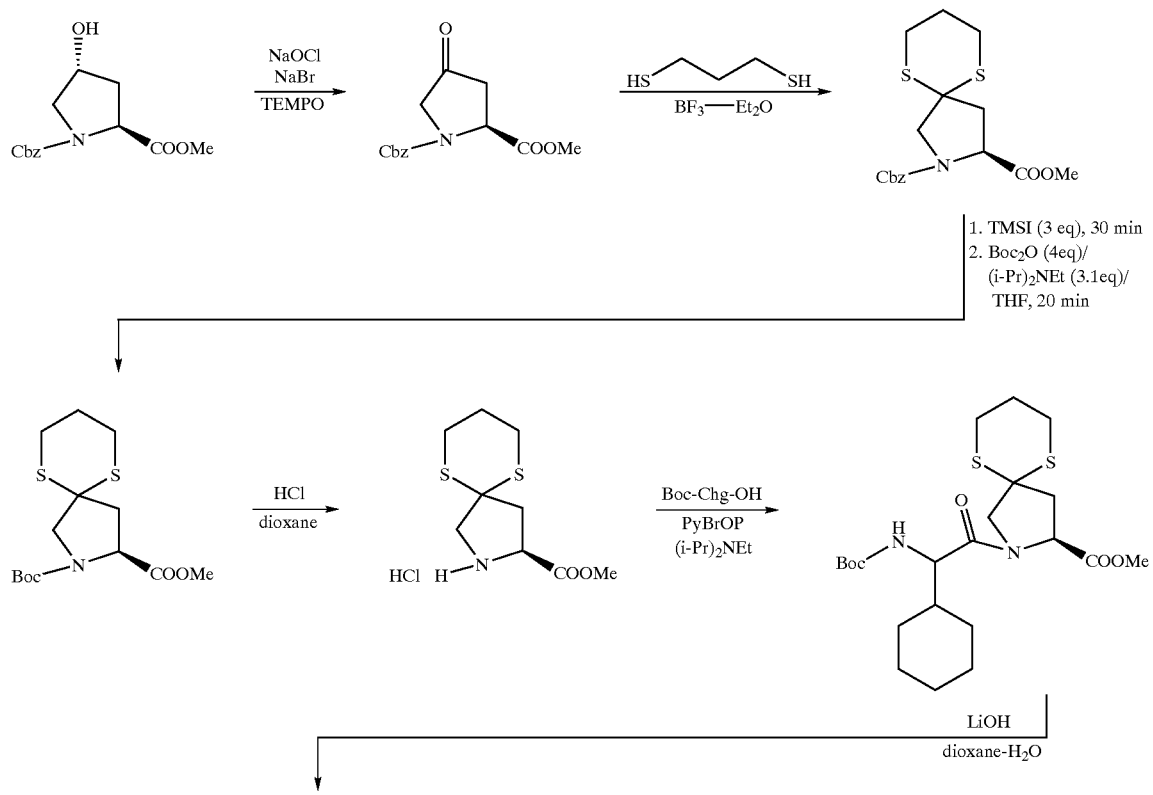

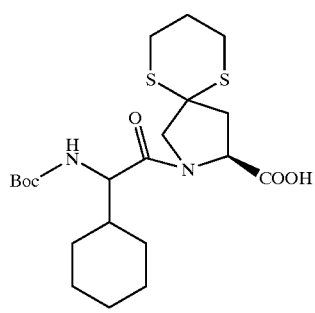
SCHEME 6
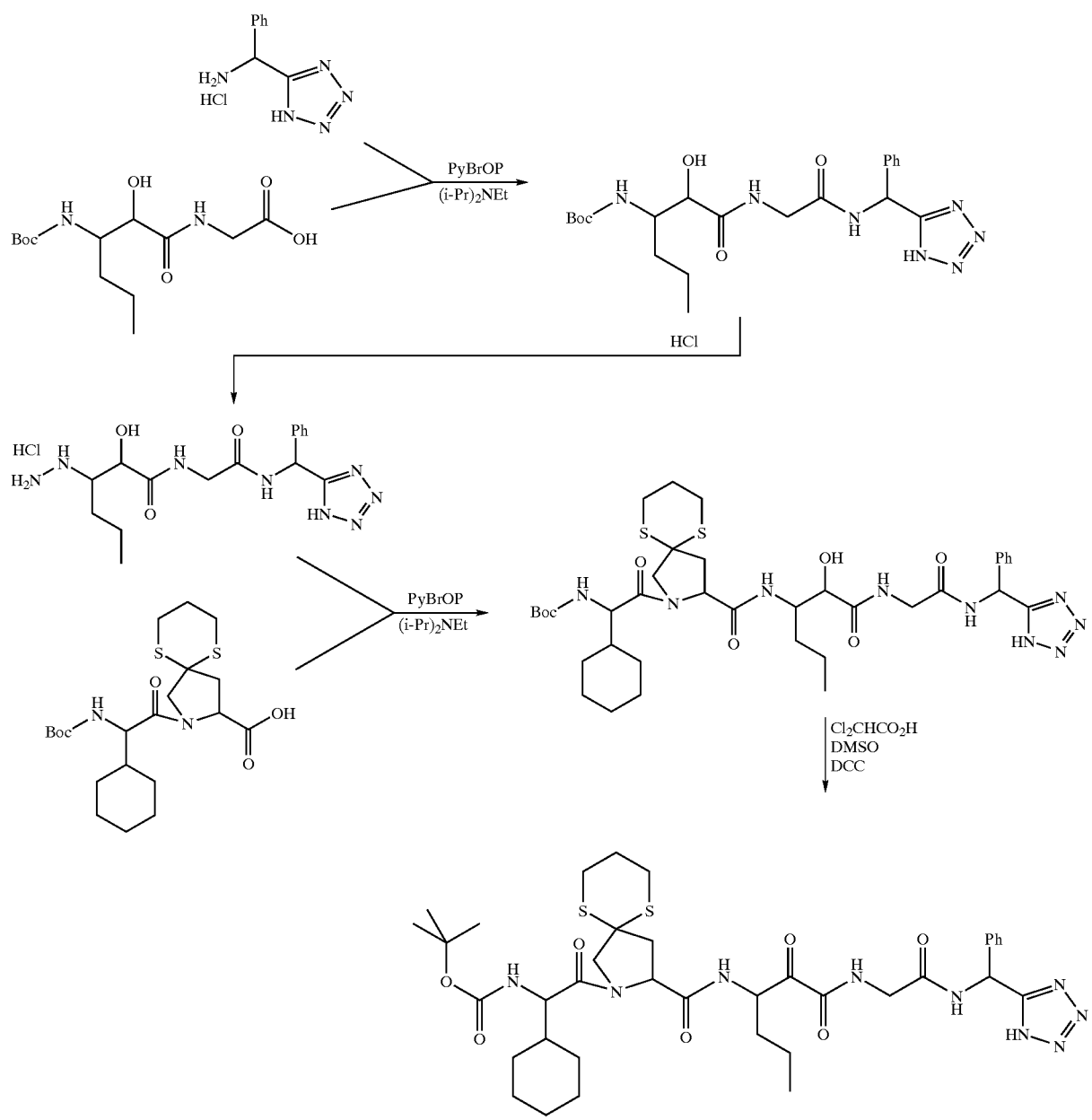

SCHEME 7
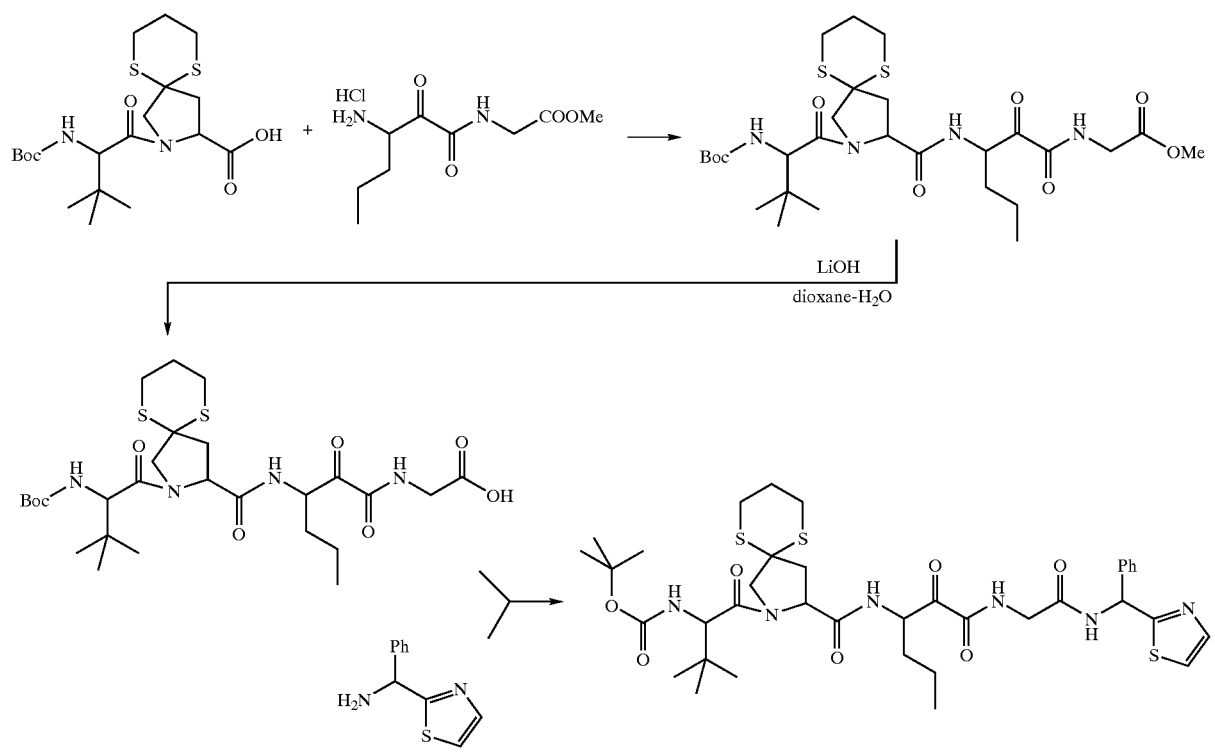
SCHEME 8
Step A
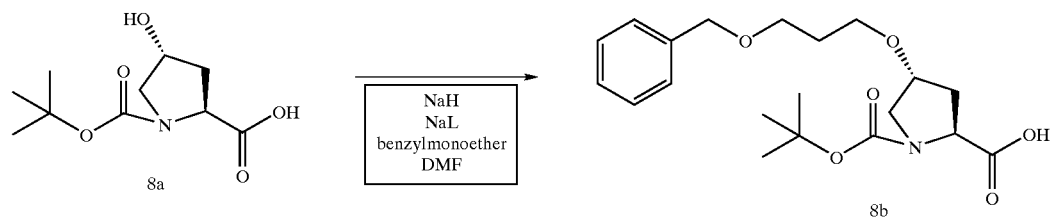
Step B
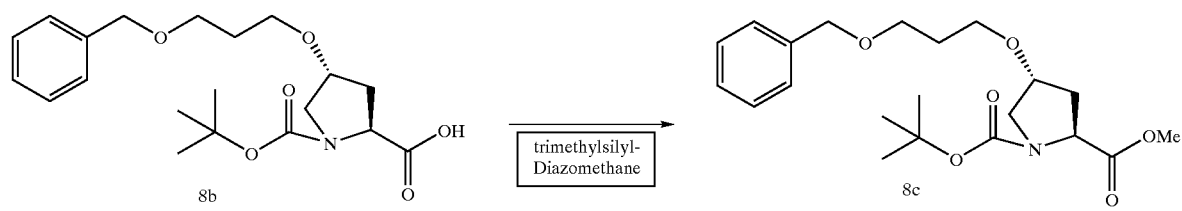
Step C
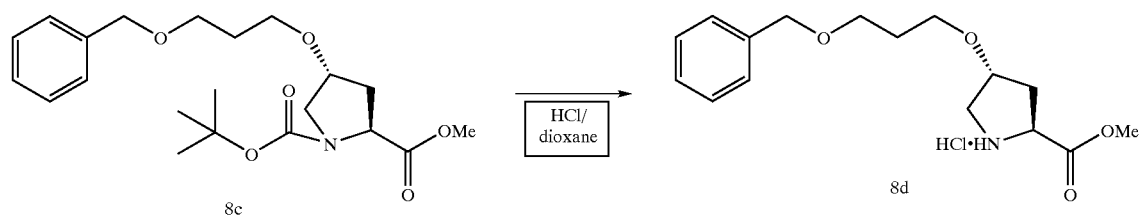
Step D

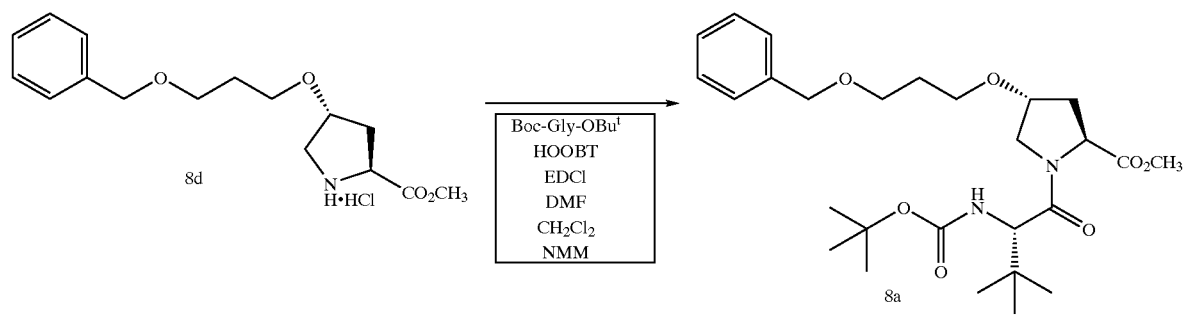
Step E
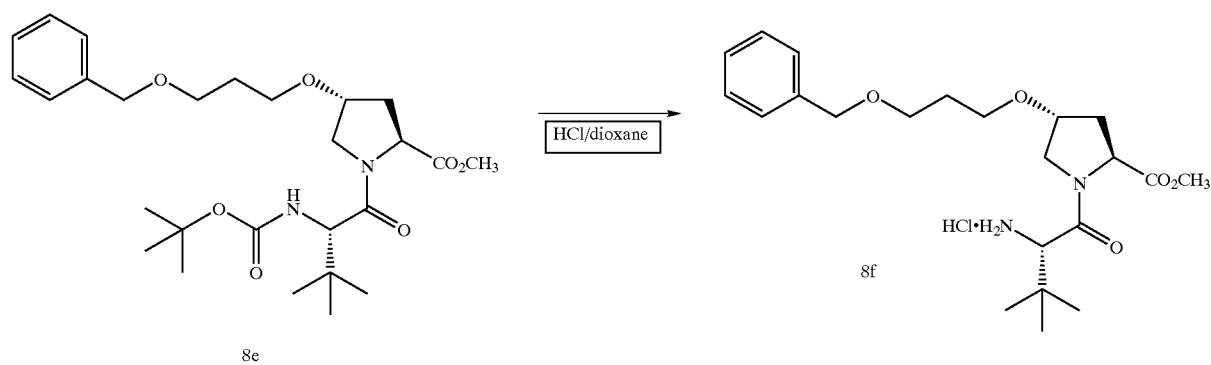
Step F
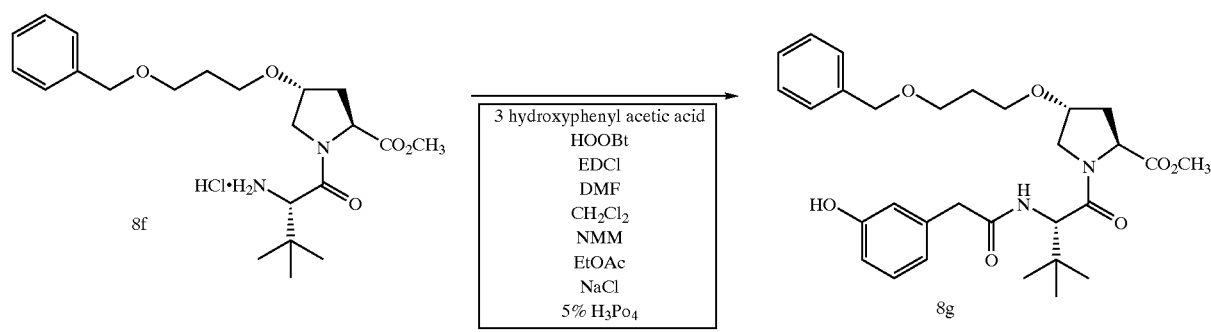

Step G
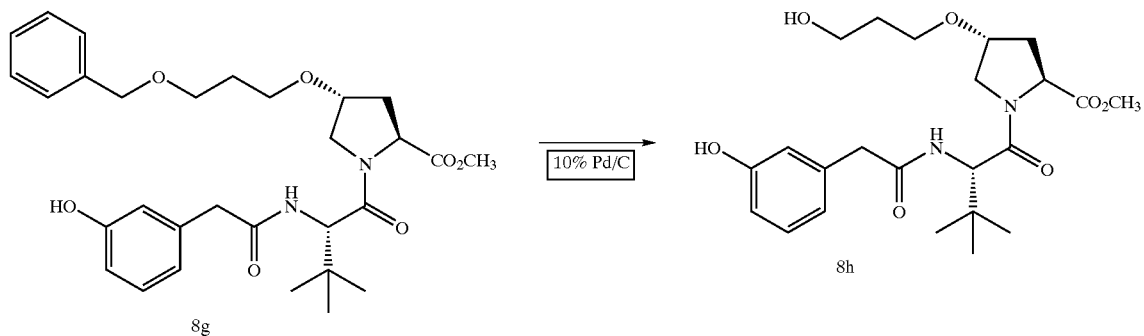
Step H
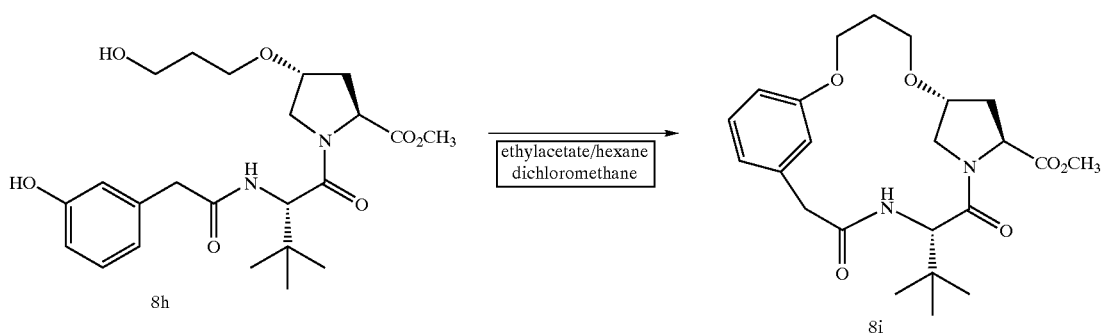
Step I
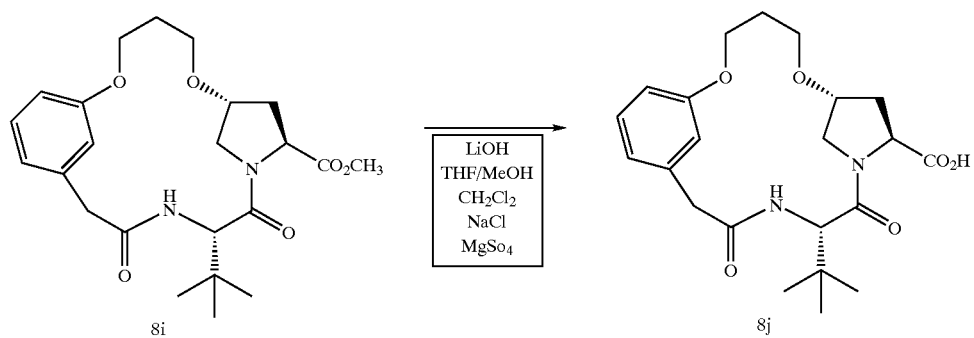

SCHEME 9
Compound 9a was prepared analogous to Scheme 8 Steps A to F.
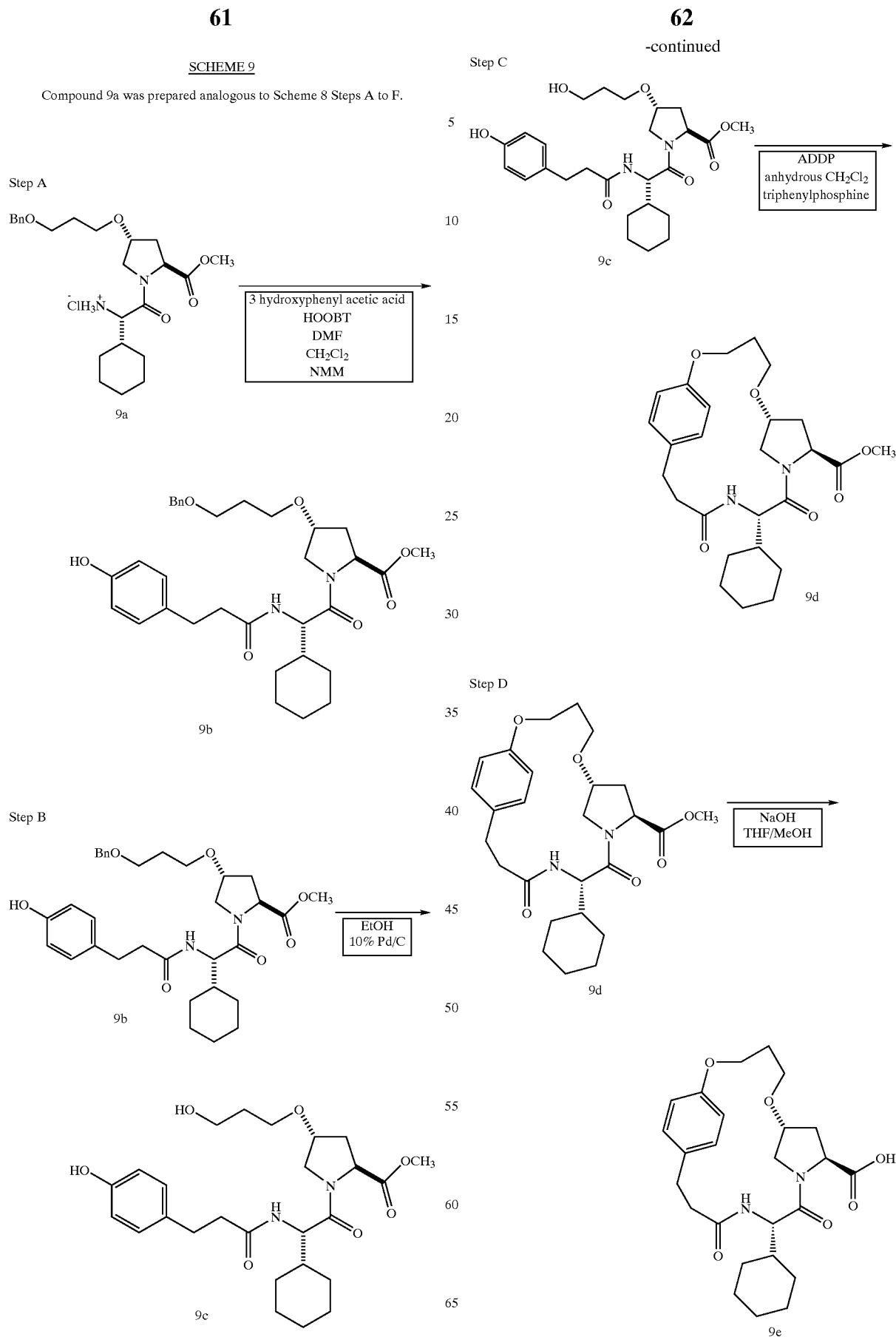

SCHEME 10

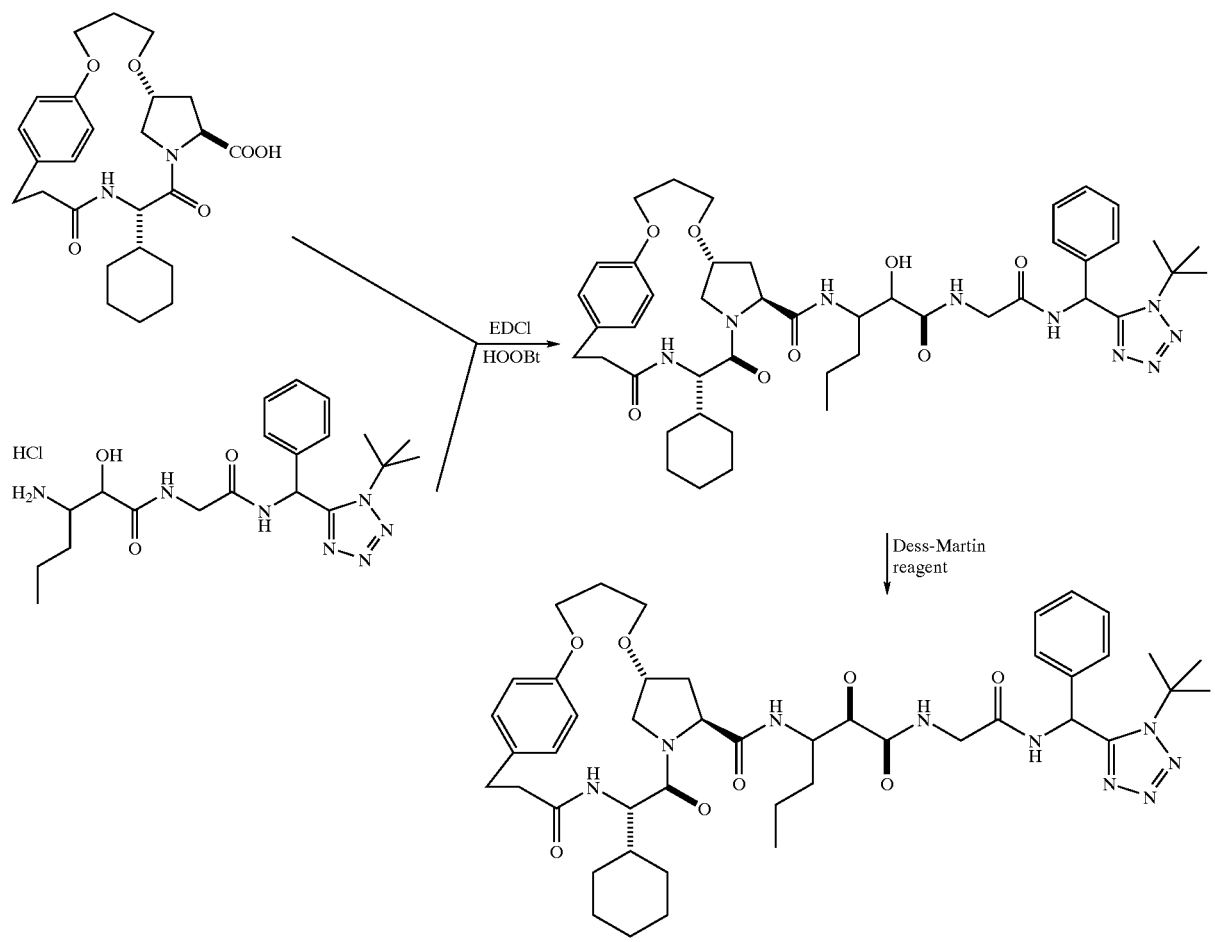

Preparation of Intermediates:

The procedures to modify an amino acid with N-Boc, N-Cbz, COOBzl, COOBu$^t$, OBzl, OBu$^t$, COOMe, both putting them on or taking them off in the presence of each other in various combinations, are generally well known to those skilled in the art. Any modifications from the known procedures are noted herein.

Commercially Available Intermediates:

The following amino acids, used as amino acid units in the preparation of the various inventive compounds, are commercially available, and were converted to their N-Boc derivatives with di-tert-butyldicarbonate, using known procedures.

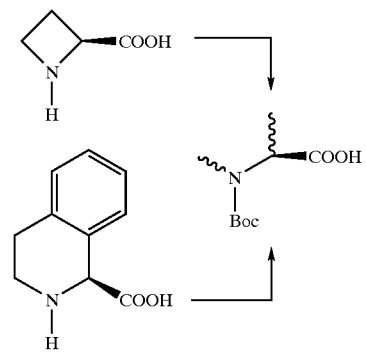

The following N-Boc-amino acids, used as P2 units, are commercially available.

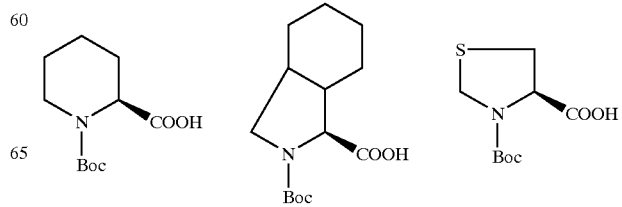

-continued

Neosystems, Princeton, New Jersey

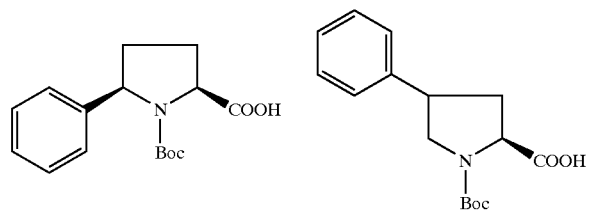

The following N-Boc-amino acid, used as P2 unit, is commercially available. After coupling the carboxylic acid, the Fmoc is removed by known treatment with piperidine before subsequent coupling.

RSP Amino Acid Analogues, Inc.
Worchester, Massachusetts

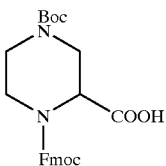

EXAMPLE A

Certain intermediates which were not commercially available were synthesized, as needed, by following the procedures given below: I.

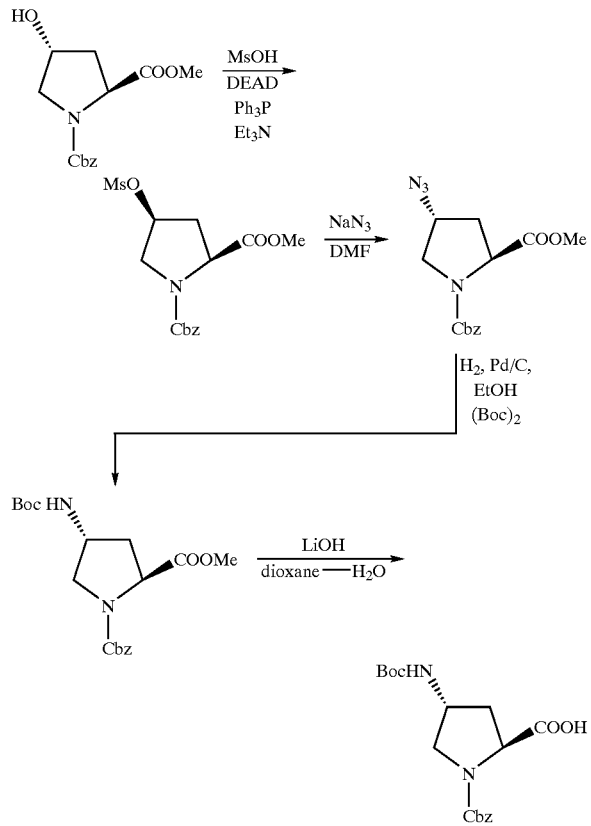

II. Mesylate:

A mixture of triphenylphosphine (8.7 g), toluene (200 mL), and methanesulfonic acid (2.07 mL) was stirred at 15° C. while slowly adding diethylazidodicarboxylate (7.18 g) to maintain the temperature below 35° C. The mixture was cooled to 20° C., and the N-Boc amino acid (7.4 g, Bachem Biosciences, Inc.), and $Et_3N$ (1.45 mL) were added, and then the mixture was stirred at 70° C. for 5 hr. The mixture was cooled to 5° C., the organic supernatant decanted, and solvent was removed from it in vacuo. The residue was stirred with $Et_2O$ (200 mL) until a precipitate deposits, the mixture was filtered, and the ethereal solution was chromatographed on silica gel (5:95 to 20:80 $EtOAc$-$Et_2O$) to obtain the product (9.3 g), which was carried into the next step.

III. Azide

Sodium azide (1.98 g) was added to a solution of the product of the step above (9.3 g) in DMF (100 mL), and the mixture stirred at 70° C. for 8 hr. The mixture was cooled, and poured into 5% aqueous $NaHCO_3$, and extracted with EtOAc. The organic layer was washed with brine, then dried over anhydrous $MgSO_4$. The mixture was filtered, and the filtrate evaporated in vacuo, to obtain the product (6.2 g), which was carried into the next step.

IV. N-Cbz(4-N-Boc)-OMe

A solution of the product of the step above (0.6 g) in dioxane (40 mL) was treated with di-tert-butyidicarbonate (0.8 g), 10% Pd—C (0.03 g), and hydrogen at one atmosphere for 18 hr. The mixture was filtered, the filtrate evaporated in vacuo, and the residue chromatographed on silica gel (1:1 to 2:1 $Et_2O$-hexane) to obtain the product.

V. N-Cbz(4-N-Boc)-OH was prepared using known ester hydrolysis using LiOH.

VI. Sulfones by Oxidation:

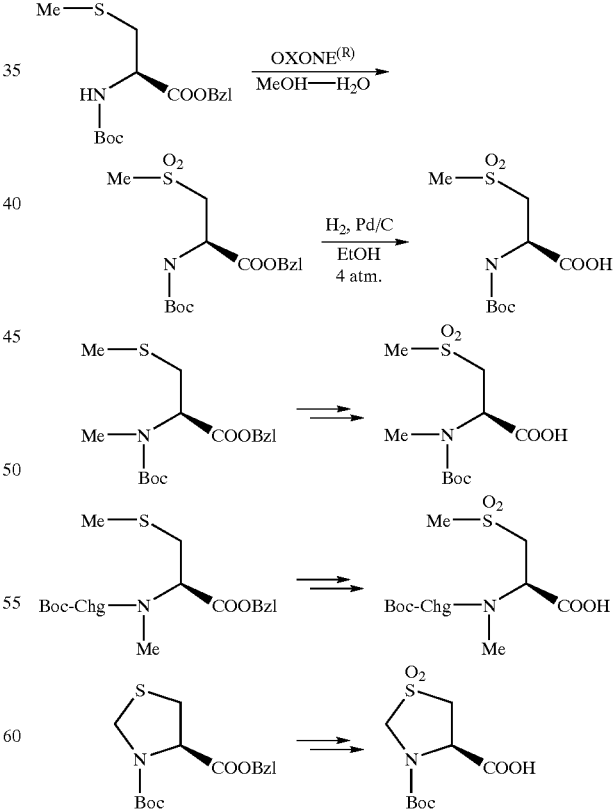

These were prepared by following the procedure of U. Larsson, et al., *Acta Chem. Scan.,* (1994), 48(6), 517–525. A solution of oxone® (20.2 g, from Aldrich Chemical Co.) in water (110 mL) was added slowly to a 0° C. solution of the sulfide (7.2 g, from Bachem Biosciences, Inc.) in MeOH (100 mL). The cold bath was removed and the mixture stirred for 4 hr. The mixture was concentrated to ½ volume on a rotary evaporator, cold water (100 mL) added, extracted with EtOAc, the extract washed with brine, and then it was dried over anhydrous MgSO$_4$. The mixture was filtered, and the filtrate evaporated in vacuo, to obtain the product as a white solid (7.7 g). A portion was crystallized from (i-Pr)$_2$O to obtain an analytical sample, [α]$_D$+8.6 (c 0.8, CHCl$_3$). Using the same procedure, the other sulfides shown were oxidized to sulfones to lead to the subject targets.

EXAMPLE 1

Step A

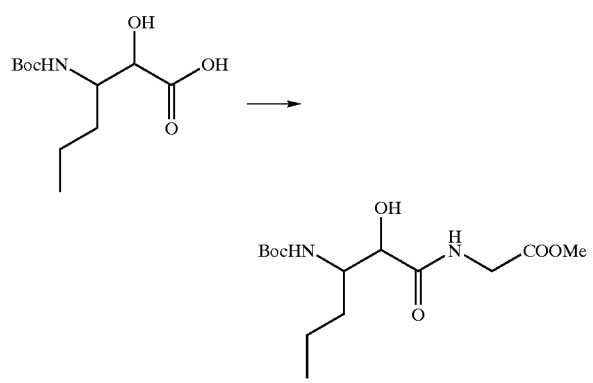

1A

To a stirred solution of compound (4.01) (12 g) prepared according to S. L. Harbeson et al., *J. Med. Chem.* 37 (18), 2918–2929 (1994), in CH$_2$Cl$_2$ (150 mL) at −20° C. was added HOOBt (7.5 g), N-methyl morpholine (6.0 mL) and EDCl (10 g). The reaction mixture was stirred for 10 minutes, followed by the addition of HCl.H$_2$N-Gly-OMe (6.8 g). The resulting solution was stirred at −20° C. for 2 hrs, then kept at 8° C. overnight. The solution was concentrated to dryness, then diluted with EtOAc (150 mL). The EtOAc solution was then washed twice with saturated NaHCO$_3$, H$_2$O, 5% H$_3$PO$_4$, and brine, dried over Na$_2$SO$_4$, filtered and concentrated to dryness to give the product, C$_{14}$H$_{26}$N$_2$O$_6$ (318.37) LRMS m/z MH$^+$=319.3.

EXAMPLE 1

Step B

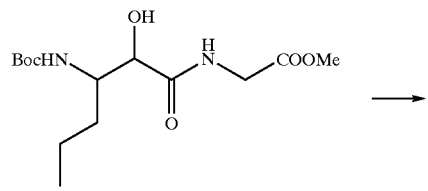

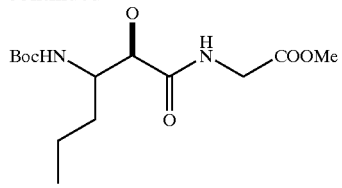

1B

A mixture of the product from Step A above (5.7 g), dichloromethane (200 mL), methyl sulfoxide (12 mL), and 2,2-dichloroacetic acid (3.2 mL) was stirred at 5° C. To this was added a solution of 1 M dicyclohexylcarbodiimide in CH$_2$Cl$_2$ (23 mL), and the resulting mixture was stirred cold for 5 min., at room temperature for 3 h. A solution of oxalic acid (0.6 g) in methanol (6 mL) was added to destroy excess oxidant, stirred for 15 min., and then filtered to remove the precipitated urea. The filtrate was concentrated in vacuo, the remainder diluted with excess ethyl acetate, and washed with cold 0.1 N NaOH, then cold 0.2 N H$_3$PO$_4$, then brine. The organic solution was dried over anhydrous MgSO$_4$, filtered, and evaporated in vacuo. The residue was chromatographed on silica gel, eluting with a gradient of EtOAc-CH$_2$Cl$_2$ (5:95 to 1:1) to obtain the title compound as an oil which solidifies to a wax slowly on standing (5 g, 88% yield) C$_{14}$H$_{24}$N$_2$O$_6$ (316.35),

EXAMPLE 1

Step C

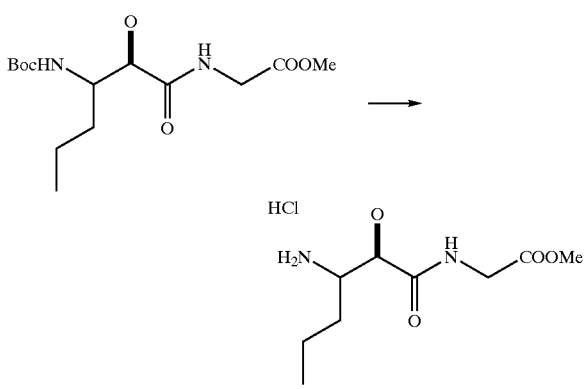

1C

Treat the product of the previous step with a 4N solution of HCl in dioxane (Aldrich Chemical Co.) for 0.5 hr. concentrate the filtrate in vacuo in a 30° C. water bath, and triturate the residue with Et$_2$O. Filter the mixture to leave the product compound as a white powder, C$_9$H$_{16}$N$_2$O$_4$.HCl (252.70), which was used subsequently without further purification.

EXAMPLE 1

Step D

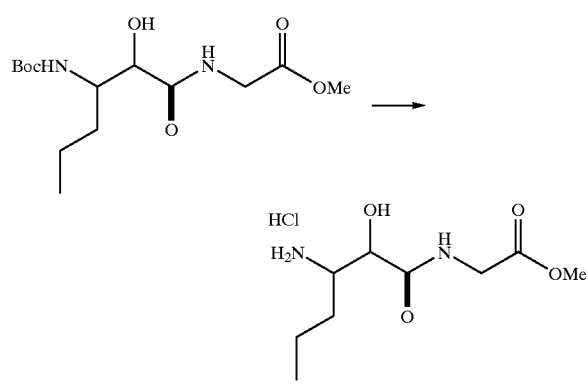

Use the procedure of step C. above to treat the product of step A. above to obtain the product as a white powder, $C_9H_{18}N_2O_4 \cdot HCl$ (254.71).

EXAMPLE 1

Step E

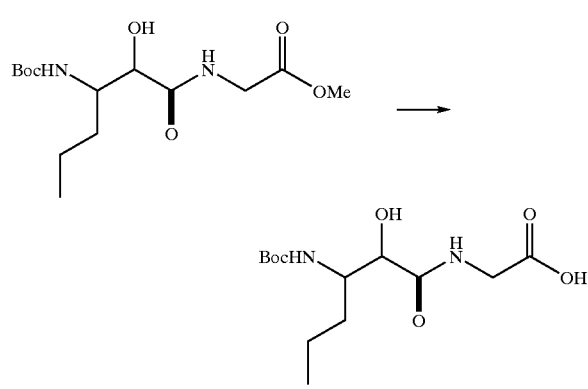

1E

Treat a solution of the product from Step A. above (8.3 g) in dioxane (150 mL) at 20° C. with 1 N aqueous LiOH (26 mL) and stir for 2 h. Pour the mixture into a solution of 10% aqueous $KH_2PO_4$ (500 mL), $H_3PO_4$ (2 mL), and saturated brine (300 mL); and then extract with EtOAc. Wash the extract with brine, dry it anhydrous $MgSO_4$, filter the mixture, and evaporate the filtrate in vacuo to leave the product as a white powder, $C_{13}H_{24}N_2O_6$ (304.34), LRMS (FAB) M+1=305.3.

EXAMPLE 2

Step A

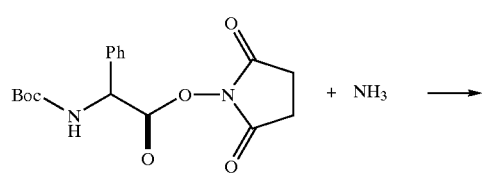

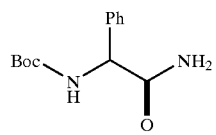

Treat a solution of N-Boc-phenylglycine N-hydoxysuccinimide ester (1.66 g; Bachem Biosciences, Inc.) in dichloromethane ($CH_2Cl_2$, 20 mL) with a solution of 0.5 M $NH_3$/dioxane (Aldrich Chemical Co.) (18.5 mL) at 5° C., then allow to warm and stir at room temperature for 4 hr. Suction-filter the mixture, add the filtrate to aq. 5% $KH_2PO_4$ (150 mL), then extract with ethyl acetate (EtOAc, 200 mL). Wash the extract twice with aq. 5% $KH_2PO_4$, then with saturated brine. Dry the extract over anhydrous $MgSO_4$, filter the mixture, and concentrate the filtrate in vacuo to leave the crude title compound (1.15 g), which was used immediately in the next step.

EXAMPLE 2

Step B

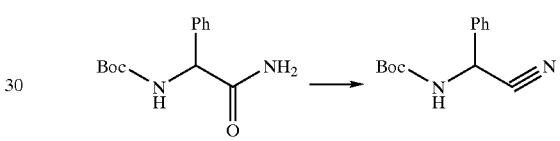

Treat a solution of the product of the previous step (1.15 g) in pyridine (10 mL) at 5° C. with $POCl_3$ (0.6 mL), then allow to warm and stir at room temperature for 3 hr. Pour the mixture onto ice (100 g), then extract with ethyl acetate (2×100 mL). Wash the extract with ice-cold 0.1 N $H_3PO_4$, then with saturated brine. Dry the extract over anhydrous $MgSO_4$, filter the mixture, and concentrate the filtrate in vacuo. Crystallize the residue from hexane to obtain the title compound (0.66 g, 60% yield overall).

EXAMPLE 3

Step A

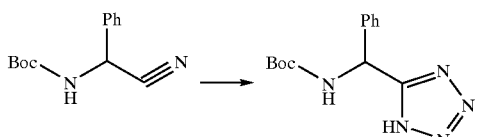

Treat a solution of the product of the previous step (0.18 g) in DMF (2 mL) with $NaN_3$ (0.055 g) and $NH_4Cl$ (0.045 g), then stir at 90° C. for 6 hr. Cool the reaction mixture, quench it with 10% aqueous $KH_2PO_4$, then extract with ethyl acetate (2×35 mL). Wash the extract with 10% aqueous $KH_2PO_4$, then with saturated brine. Dry the extract over anhydrous $MgSO_4$, filter the mixture, and concentrate the filtrate in vacuo to leave the crude title compound, which was used in the next step without further purification; $C_{13}H_{17}N_5O_2$ (275.31); LRMS (FAB) M+1=276.2.

EXAMPLE 3

Step B

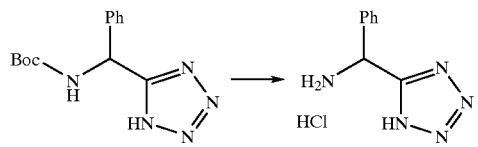

Use the procedure of Example 1 Step C. above to treat the product of the previous step to obtain the product as a white powder, which is used subsequently without further purification.

EXAMPLE 4

Step A

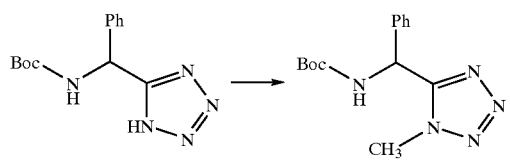

4A

Treat a solution of the product of Example 2a. (0.055 g) and THF (1.5 mL) at 5° C. with excess of a solution of diazomethane in Et$_2$O. Allow the solution to warm to room temperature over 2 hr., quench with hexane, and concentrate the filtrate in vacuo to leave the crude title compound (0.056 g), which was used without further purification; $C_{14}H_{19}N_5O_2$ (Mol. Wt.: 289.33), LRMS (FAB) M+1=290.0.

EXAMPLE 4

Step B

Use the procedure if Example 1 Step C. above to treat the product of the preceding step (0.055 g) to obtain the product as a white powder (0.027 g), as a 3:1 mixture of regioisomers, $C_9H_{11}N_5 \cdot HCl$ (225.68) H1NMR (DMSO-d6) d 9.3 (br s, 3 H), 7.45 (m, 5 H), 6.22 (s, 0.3 H) and 6.03 (s, 0.7 H), 4.39 (s, 2.1 H) and 3.94 (s, 0.9 H).

EXAMPLE 5

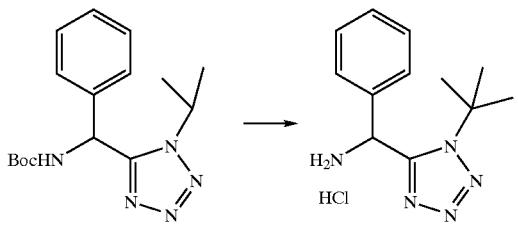

Following the procedure of Example 1, Step C above, the product of the previous Step was converted to the corresponding product, which is used subsequently without further purification.

EXAMPLE 6

Step A

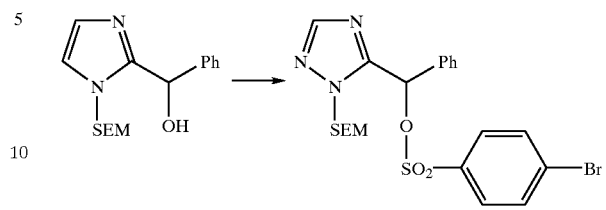

4-bromobenzenesulfonyl chloride (7.1 g) was added to a solution of the ethyl alcohol (N. Fugina, et al., *Heterocycles,.* 1992, 34(2), 303–314) at 0° C., followed by Et$_3$N (3.9 mL) and DMAP (3.4 g), and stir the mixture for 18 hr. at ambient temperature. Wash the reaction mixture with 10% aqueous KH$_2$PO$_4$, then brine, and dry the solution over anhydrous MgSO$_4$. Filter the mixture, evaporate solvent in vacuo, and chromatograph the residue on silica gel (15:85 EtOAc-CH$_2$Cl$_2$) to obtain the product (3.6 g) $C_{21}H_{26}BrN_3O_4SSi$ (524.51) LRMS (FAB) M+H=524.2.

EXAMPLE 6

Step B

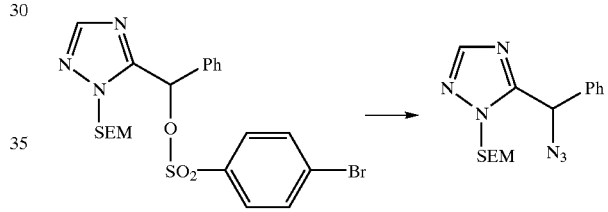

Stir a mixture of the product from the step above (3.6 g), sodium azide (0.56 g), and DMF (50 mL) at 100° C. for 4 hr. Pour the cooled reaction mixture into cold water, extract with EtOAc, wash the extract with brine, and dry it over anhydrous MgSO$_4$. Filter the mixture, evaporate solvent in vacuo, and chromatograph the residue on silica gel (3:97 EtOAc-CH$_2$Cl$_2$) to obtain the product (2.8 g) $C_{15}H_{22}N_6OSi$ (330.47) LRMS (FAB) M+H=331.2.

EXAMPLE 6

Step C

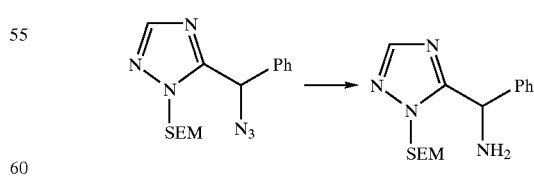

Treat a solution of the product from the step above (1.3 g) in EtOH (50 mL) with 10% Pd—C (0.15 g) and hydrogen at 1 atm. for 18 hr. Filter the mixture and evaporate solvent in vacuo to leave the product (1.2 g) $C_{15}H_{24}N_4OSi$ (304.47) LRMS (FAB) M+H=305.3.

EXAMPLE 7

Step A

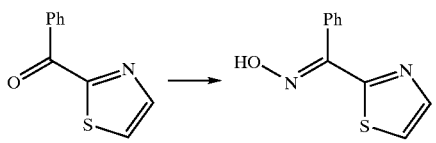

A stirred solution of 2-benzoylthiazole (1.9 g, G. Jones, et al., *Tetrahedron,* 1991, 47(16), 2851–2860.) in EtOH:H$_2$O (50:5 mL) was treated with hydroxylamine hydrochloride (1.4 g), and heated at reflux for 24 hr. The cooled mixture was poured into EtOAc and washed successively with 10% aqueous KH$_2$PO$_4$, then brine. The extract was dried over anhydrous MgSO$_4$, the mixture was filtered, and the solvent was evaporated in vacuo to leave the product as a mixture of geometric isomers, C$_{10}$H$_8$N$_2$OS (204.25) LRMS (FAB) M+1=205.2.

EXAMPLE 7

Step B

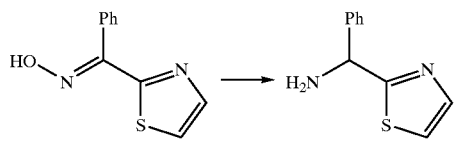

The product of the preceding step was mixed with MeOH (30 mL), formic acid (15 mL), and water (15 mL), and cooled to 0° C. Zinc dust was added in small portions to the stirred mixture over 0.5 hr., and the mixture was stirred an additional 18 hr. at 0° C. The mixture was then suction-filtered through a celite pad, and the filtrate was evaporated in vacuo. The gum residue was taken up with EtOAc (0.5 L) and 1 N NaOH (0.1 L), the mixture again suction-filtered, and the aqueous layer of the filtrate discarded. The organic extract was washed with brine and dried over anhydrous MgSO$_4$. The mixture was filtered, the solvent was evaporated in vacuo, and the residue was chromatographed (silica gel, 1:1 EtOAc:CH$_2$Cl$_2$) to give the product, C$_{10}$H$_{10}$N$_2$S (190.27) LRMS (FAB) M+1=191.1.

EXAMPLE 8

Step A

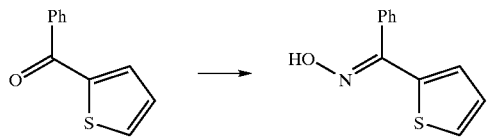

Following the procedure of Example 6 step A. above, 2-benzoylthiophene (C. Malanga, et al., *Tetrahedron Lett.,* 1995, 36 (50), 9185–9188) was converted to the corresponding product, C$_{11}$H$_9$NOS (203.26), LRMS (FAB) M+1=204.2.

EXAMPLE 8

Step B

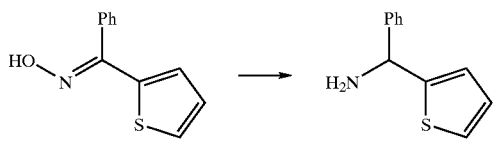

Following the procedure of Example 6 step B. above, the product of the preceding step was converted to the corresponding product, C$_{11}$H$_{11}$NS (189.28), LRMS (FAB) M+1=190.2.

EXAMPLE 9

Step A

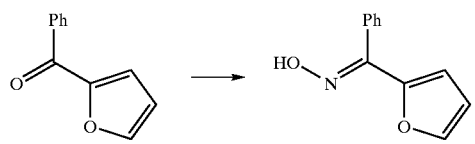

Following the procedure of Example 6 step A. above, 2-benzoylfuran (M. J. Aurell, et al., *J.Org.Chem.,* 1995, 60 (1), 8–9) was converted to the corresponding product, C$_{11}$H$_9$NO$_2$ (187.19), 188.1.

EXAMPLE 9

Step B

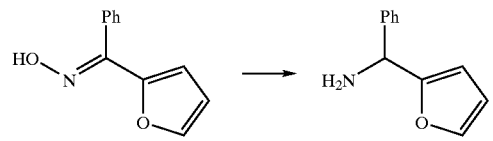

Following the procedure of Example 6 step B. above, the product of the preceding step was converted to the corresponding product, C$_{11}$H$_{11}$NO (173.21), LRMS (FAB) M+1=174.2.

EXAMPLE 10

Step A

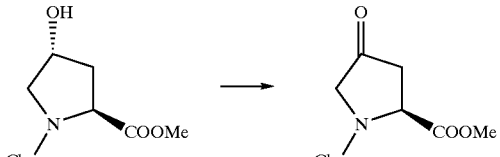

Combine N-Cbz-hydroxyproline methyl ester (available from Bachem Biosciences, Incorporated, King of Prussia, Pa.), compound (2.1) (3.0 g), toluene (30 mL), and ethyl acetate (30 mL). The mixture was stirred vigorously, and then a solution of NaBr/water (1.28 g/5 mL) was added. To this was added 2,2,6,6-tetramethyl-1-piperidinyloxy free radical (TEMPO, 17 mg, from Aldrich Chemicals, Milwaukee, Wis.). The stirred mixture was cooled to 5° C.

and then was added a prepared solution of oxidant [commercially available bleach, Clorox® (18 mL), NaHCO₃ (2.75 g) and water to make up 40 mL] dropwise over 0.5 hr. To this was added 2-propanol (0.2 mL). The organic layer was separated, and the aqueous layer extracted with ethyl acetate. The organic extracts were combined, washed with 2% sodium thiosulfate, then saturated brine. The organic solution was dried over anhydrous MgSO₄, filtered, and evaporated the filtrate under vacuum to leave a pale yellow gum suitable for subsequent reactions (2.9 g, 97% yield), $C_{14}H_{15}NO_5$ (277.28), mass spec. (FAB) M+1=278.1.

EXAMPLE 10

Step B

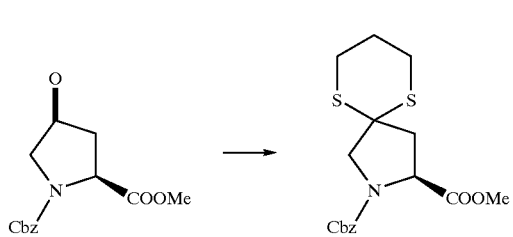

Compound (2.2) from Step A above (7.8 g) was dissolved in dichloromethane (100 mL), and cooled to 15° C. To this mixture was first added 1,3-propanedithiol (3.1 mL), followed by freshly distilled boron trifluoride etherate (3.7 mL). The mixture was stirred at room temperature for 18 h. While stirring vigorously, a solution of K₂CO₃/water (2 g/30 mL)was carefully added, followed by saturated NaHCO₃ (10 mL). The organic layer was separated from the aqueous layer (pH ~7.4), washed with water (10 mL), then brine. The organic solution was dried over anhydrous MgSO₄, filtered, and evaporated under vacuum. The residue was chromatographed on silica gel, eluting with toluene, then a with a gradient of hexane-Et₂O (2:3 to 0:1) to afford a brown oil (7.0 g, 68% yield), $C_{17}H_{21}NO_4S_2$ (367.48), mass spec. (FAB) M+1=368.1.

EXAMPLE 10

Step C

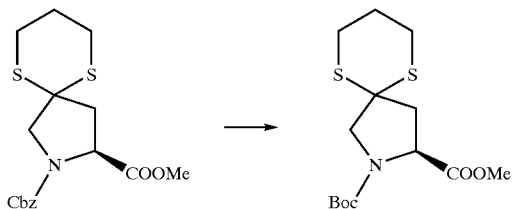

A solution of compound (2.3) from Step B above (45 g) in acetonitrile (800 mL) at 20° C. was treated with freshly distilled iodotrimethylsilane (53 mL) at once. The reaction was stirred for 30 min., then poured into a freshly prepared solution of di-t-butyidicarbonate (107 g), ethyl ether (150 mL), and diisopropylethylamine (66.5 mL). The mixture stirred for 30 min. more then was washed with hexane (2×500 mL). Ethyl acetate (1000 mL) was added to the lower acetonitrile layer, and then the layer was washed with 10% aqueous KH₂PO₄ (2×700 mL), and brine. The filtrate was evaporated under vacuum in a 25° C. water bath, taken up in fresh ethyl acetate (1000 mL), and washed successively with 0.1 N HCl, 0.1 N NaOH, 10% aqueous KH₂PO₄, and brine. The organic solution was dried over anhydrous MgSO₄, filtered, and evaporated under vacuum. The residue (66 g) was chromatographed on silica gel (2 kg), eluting with hexane (2 L), then Et₂O/hexane (55:45, 2 L), then Et₂O (2 L) to afford an orange gum which slowly crystallized on standing (28 g, 69% yield), $C_{14}H_{23}NO_4S_2$ (333.46), mass spec. (FAB) M+1=334.1.

EXAMPLE 10

Step D

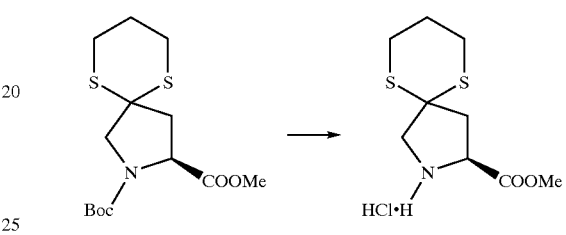

To a solution of compound (2.4) from Step C above (1 g) in dioxane (5 mL), was added 4 N HCl-dioxane solution (50 mL). The mixture was stirred vigorously for 1 hr. The mixture was evaporated under vacuum in a 25° C. water bath. The residue was triturated with Et₂O, and filtered to leave the title compound (0.76 g, 93% yield), $C_9H_{15}NO_2S_2$·HCl (269.81), mass spec. (FAB) M+1=234.0.

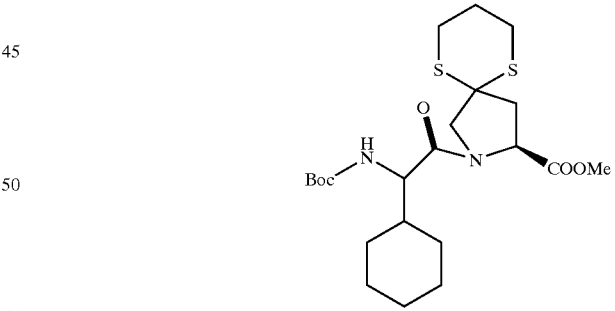

EXAMPLE 10

Step E

10E

A mixture of compound (2.6) from Step E above (1.12 g), N-Boc-cyclohexylglycine (Boc-Chg-OH, 1.0 g, from Sigma Chemicals, St. Louis, Mo.), dimethylformamide (20 mL), and PyBrOP coupling reagent (2.1 g) was cooled to 5° C. To this was added diisopropylethylamine (DIEA or DIPEA, 2.8 mL). The mixture was stirred cold for 1 min., then stirred at

EXAMPLE 10

Step F

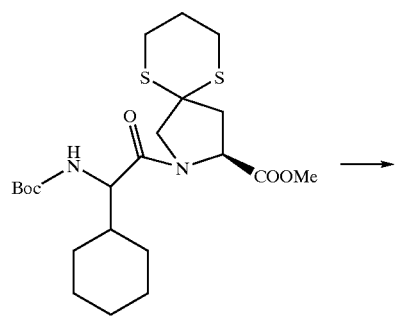

room temperature for 6 hr. The reaction mixture was poured into cold 5% aqueous $H_3PO_4$ (150 mL) and extracted with ethyl acetate (2×150 mL). The combined organic layer was washed with cold 5% aqueous $K_2CO_3$, then 5% aqueous $KH_2PO_4$, then brine. The organic solution was dried over anhydrous $MgSO_4$, filtered, and evaporated under vacuum. The residue was chromatographed on silica gel, eluting with EtOAc-$CH_2Cl_2$ to afford a white solid (0.8 g, 50% yield), $C_{22}H_{36}N_2O_5S_2$ (472.66), mass spec. (FAB) M+1=473.2.

A solution of compound (?) from Step ? above (0.8 g) in dioxane (10 mL) at 20° C. was treated with 1N aqueous LiOH (3.4 mL) and stirred for 4 h. The mixture was concentrated under vacuum in a 30° C. water bath to half volume. The remainder was diluted with water (25 mL), extracted with $Et_2O$ (2×20 mL). The aqueous layer was acidified to pH ~4 with 6 N HCl, extracted with ethyl acetate, and washed with brine. The organic solution was dried over anhydrous $MgSO_4$, filtered, and evaporated under vacuum to leave the title compound (2.8) (0.7 g), $C_{21}H_{34}N_2O_5S_2$ (458.64), mass spec. (FAB) M+1=459.2.

EXAMPLE 12

Step A

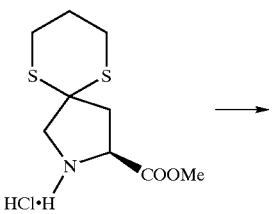

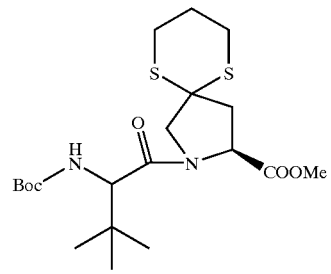

Following the procedure of Example 10 step E. above, N-Boc-Tle-OH (Bachem Biosciences, Inc.) and the product of Example 9 step D. were reacted to give the corresponding product, $C_{20}H_{34}N_2O_5S_2$ (446.63), LRMS (FAB) M+1= 447.3.

EXAMPLE 12

Step B

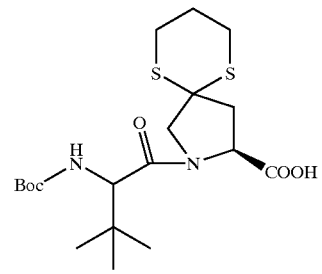

Following the procedure of Example 10 step E. above, the product of the preceding step was converted to the corresponding product, $C_{19}H_{32}N_2O_5S_2$ (432.60), LRMS (FAB) M+1=433.3.

EXAMPLE 12

Step A

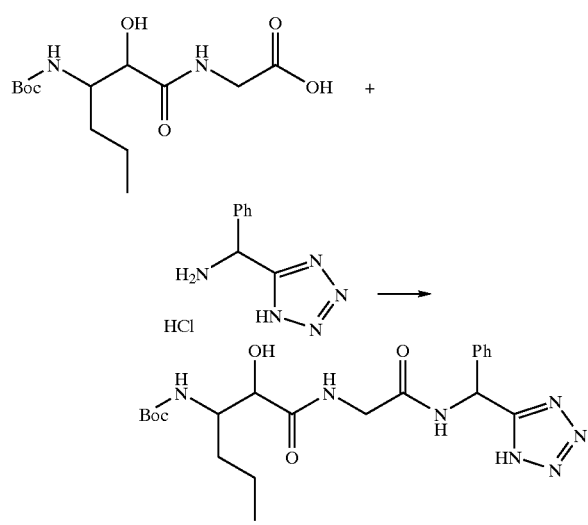

Cool a stirred mixture of the product of the previous step (0.11 g), the product of Example-1 Step E. above [Boc-Nva(OH)-Gly-OH] (0.205 g), dimethylformamide (7 mL), and PyBrOP coupling reagent (0.385 g) to 5° C., then add diisopropylethylamine (DIPEA, 0.252 mL). Stir the mixture cold for 1 min., then stir at room temperature for 6 hr. Pour the reaction mixture into cold 1% aqueous $H_3PO_4$ (150 mL) and extract with ethyl acetate. Wash the combined organics with cold 5% aqueous $K_2CO_3$, then 5% aqueous $KH_2PO_4$, then brine. Dry the organic solution over anhydrous $MgSO_4$, filter, and evaporate the filtrate in vacuo to leave the crude title compound (0.15 g), which was used in the next step without further purification.

EXAMPLE 12

Step B

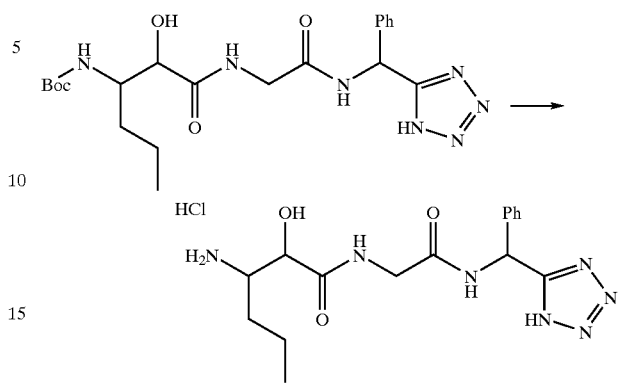

Treat the product of the previous step with a 4N solution of HCl in dioxane for 0.5 hr. concentrate the filtrate in vacuo in a 30° C. water bath, and tritrate the residue with $Et_2O$. Filter the mixture to leave the title compound as a white powder 90.13 g0, which was used in the next step without further purification; $C_{16}H_{23}N_7O_3$ (361.40), LRMS (FAB) M+1=362.4.

EXAMPLE 12

Step C

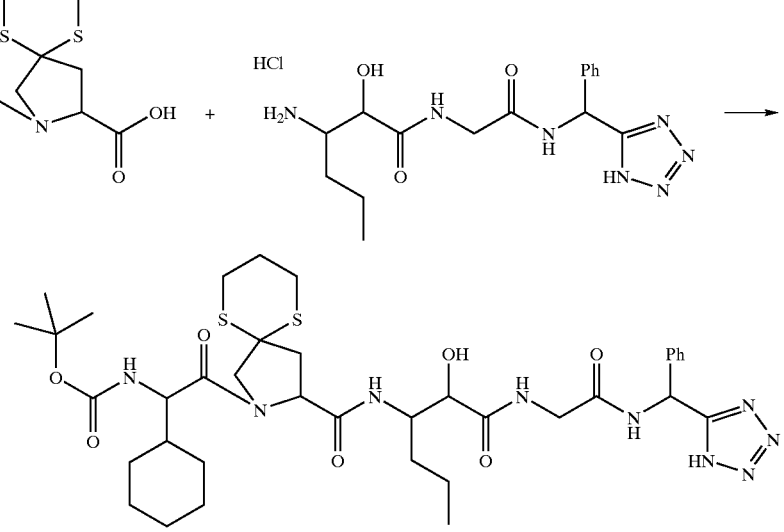

Cool a stirred mixture of the product of Example 5 step B. (0.06 g), the product of Example-8 Step G. (0.85 g), dimethylformamide (8 mL), and PyBrOP coupling reagent (0.088 g) to 5° C., then add diisopropylethylamine (DIPEA, 0.89 mL). Stir the mixture cold for 1 min., then stir at room temperature for 48 hr. Pour the reaction mixture into cold 1% aqueous $H_3PO_4$ and extract with ethyl acetate. Wash the combined organics with 5% aqueous $KH_2PO_4$, then brine. Dry the organic solution over anhydrous $MgSO_4$, filter, and evaporate the filtrate in vacuo to leave the crude title compound (0.13 g). Chromatograph the residue on silica gel with $MeOH—CH_2Cl_2$ (1:99 to 10:90 gradient) to obtain the title compound (0.092 g); $C_{37}H_{55}N_9O_7S_2$ (802.02), LRMS (FAB) M+1=802.6.

EXAMPLE 12

Step D

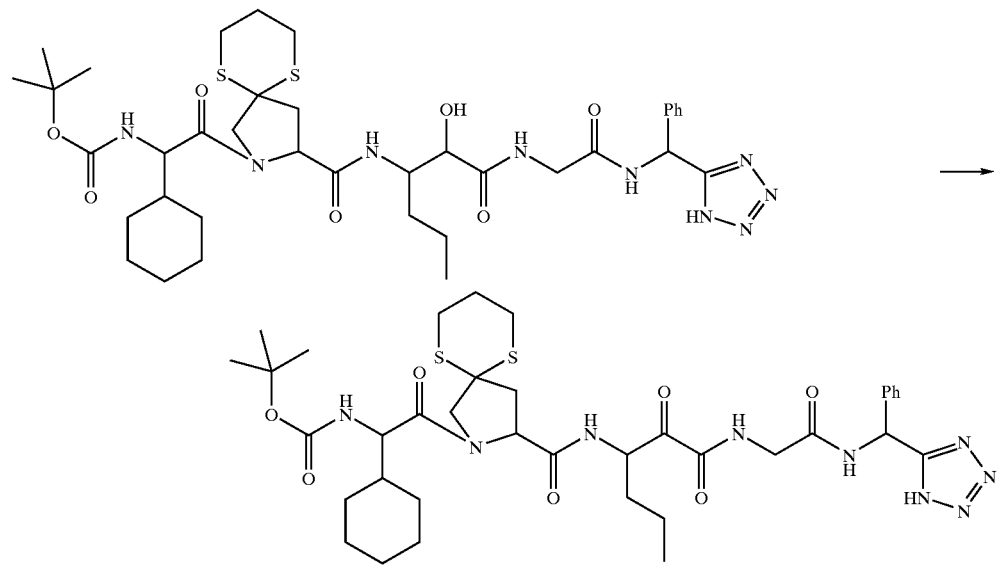

Cool a solution of oxalyl chloride (25 μL) and $CH_2Cl_2$ to −70° C. Add slowly a solution of methyl sulfoxide (DMSO, 50 μL) and $CH_2Cl_2$ (1 mL) below −60° C. Cool to −70° C., and add dropwise a solution of the product of the previous step (0.0.09 g) and $CH_2Cl_2$ (1 mL) below −60° C. Stir an additional 0.5 hr., add slowly triethylamine ($Et_3N$, 0.13 mL) below −50° C., then warm to 10° C. Dilute the reaction with excess ethyl acetate, and wash the solution with cold 0.1 N HCl, then brine. Dry the organic solution aver anhydrous $MgSO_4$, filter, and evaporate the filtrate under vacuum. Chromatograph the residue on silica gel, eluting with MeOH—$CH_2Cl_2$ (1:99 to 25:75 gradient) to obtain the title compound (0.011 g, 12% yield), $C_{37}H_{53}N_9O_7S_2$ (800.01), LRMS (FAB) M+1=800.3.

EXAMPLE 13

Step A

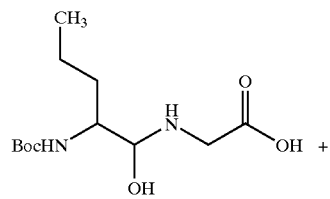

-continued

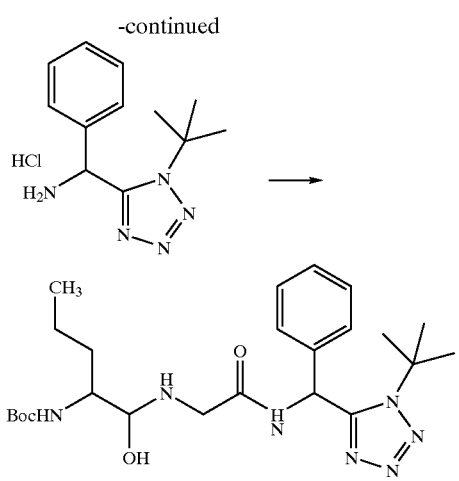

A solution of the product of example 1 step E. (100 mg, 0.22 mmols) in dry DMF (2.5 mL) was treated with HOOBt (45 mg, 0.33 mmols) and Hünigs base (141 mg, 1.1 mmols, 5.0 equiv.). The reaction mixture was cooled to −20° C. and treated with EDCl (63 mg, 0.33 mmols, 1.5 equiv) and stirred for 20 min. The reaction mixture was treated with amine hydrochloride (118 mg, 0.27 mmols, 1.22 equiv.) and stirred at rt for 12 h. The reaction mixture was concentrated in vacuo and diluted with $H_2O$ (30 mL). The aqueous layer was extracted with $CH_2Cl_2$ (3×50 mL) and EtOAc (3×50 mL). The combined organic layers were extracted with aq. HCl (2M), aq. $NaHCO_3$ (satd), dried ($MgSO_4$) filtered concentrated in vacuo to obtain a colorless solid 1k (79 mg) which was used for oxidation; LRMS [electron spray, m/z (rel int)]: M+1=826 (100).

EXAMPLE 13

Step B

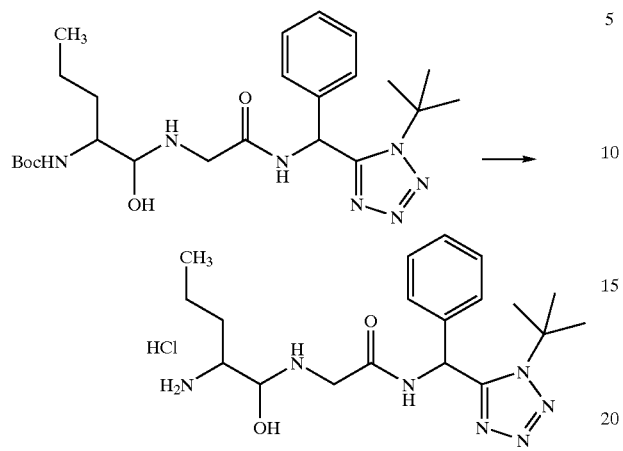

Following the procedure of Example 12 Step B., the product of the preceding Step was converted to the corresponding product, which was used as it was for subsequent reactions. MS (Electron spray): [835 (2M+1)$^+$, 40], 418 [M+1]$^+$, 100)].

EXAMPLE 14

Step A

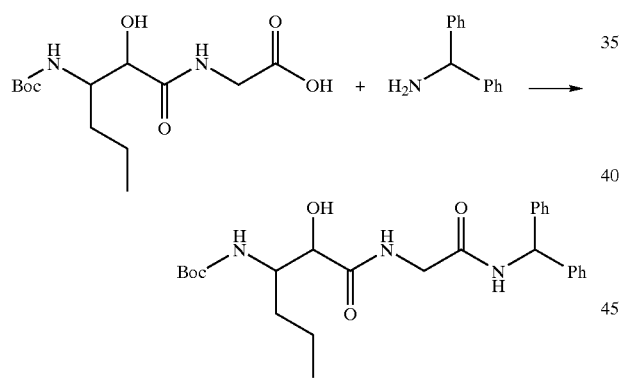

Following the procedure of Example 12 Step A. above, the product of Example 1 step E. is reacted with benzhydrylamine to give the corresponding product, $C_{26}H_{35}N_3O_5$ (469.57), LRMS (FAB) M+1=470.4.

EXAMPLE 14

Step B

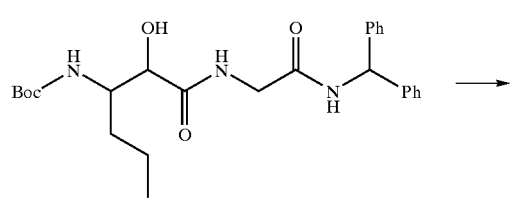

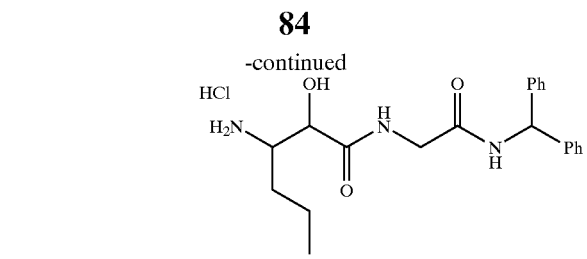

Following the procedure of Example 12 step B., the product of the preceding step was converted to the corresponding product, $C_{21}H_{27}N_3O_3$·HCl (405.92), LRMS (FAB) M+1=370.4.

EXAMPLE 14

Step C

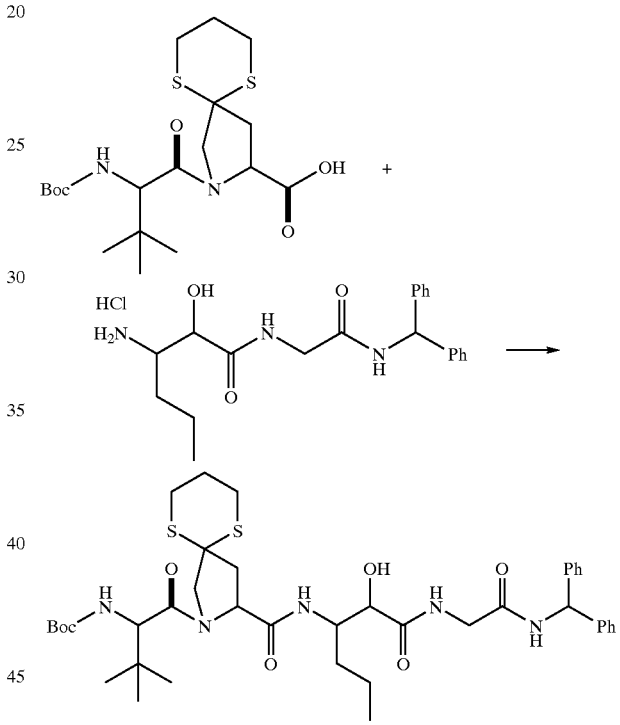

Following the procedure of Example 12 step C., the product of the preceding step was reacted with the product of Example 10 step B. to give the corresponding product, $C_{40}H_{57}N_5O_7S_2$ (784.04), LRMS (FAB) M+1=784.5.

EXAMPLE 14

Step D

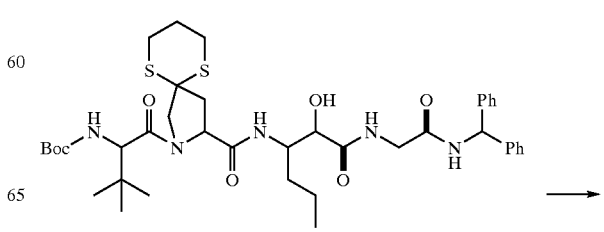

-continued

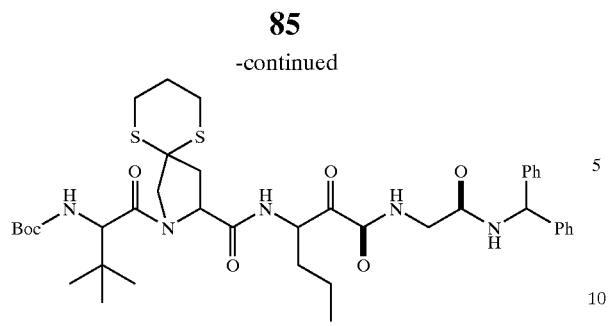

Following the procedure of Example 12 step D., the product of the preceding step was converted to the corresponding product, $C_{40}H_{55}N_5O_7S_2$ (782.03), LRMS (FAB) M+1=782.4.

EXAMPLE 15

Step A

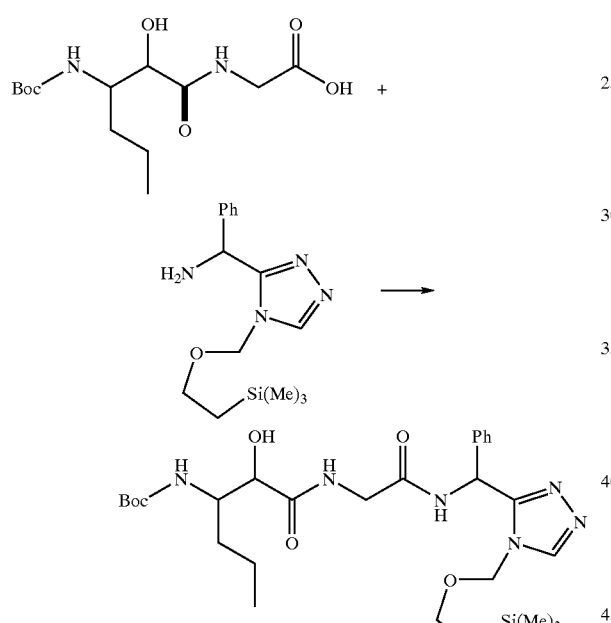

Following the procedure of Example 12 Step A. above, the product of Example 1 step E. is reacted with the product of Example 5 step C. to give the corresponding product, $C_{28}H_{46}N_6O_6Si$ (590.79), LRMS (FAB) M+1=591.4.

EXAMPLE 15

Step B

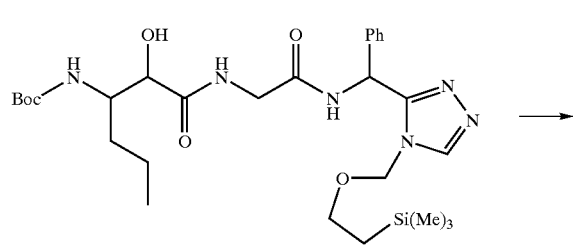

-continued

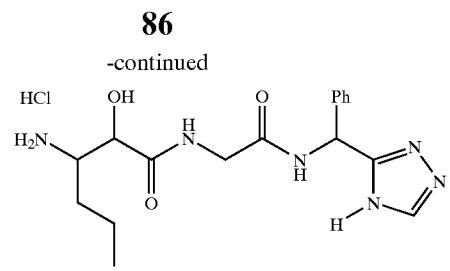

Following the procedure of Example 12 Step B., the product of the preceding step was converted to the corresponding product, $C_{17}H_{24}N_6O_3 \cdot HCl$ (396.87), LRMS (FAB) M+1=361.3.

EXAMPLE 15

Step C

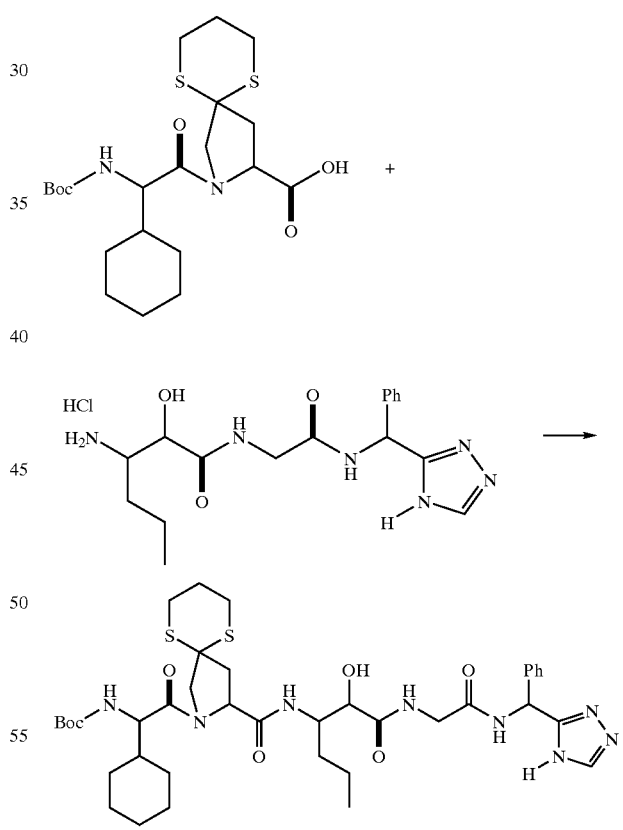

Following the procedure of Example 12 Step C., the product of the preceding step was converted to the corresponding product, $C_{38}H_{56}N_8O_7S_2$ (801.03), LRMS (FAB) M+1=801.5.

EXAMPLE 15

Step D

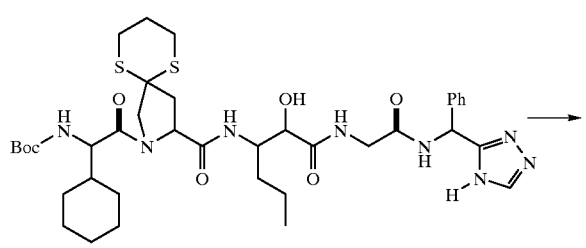

Following the procedure of Example 12 Step D., the product of the preceding step was converted to the corresponding product, $C_{38}H_{54}N_8O_7S_2$ (809.02), LRMS (FAB) M+1=799.4.

EXAMPLE 16

Step A

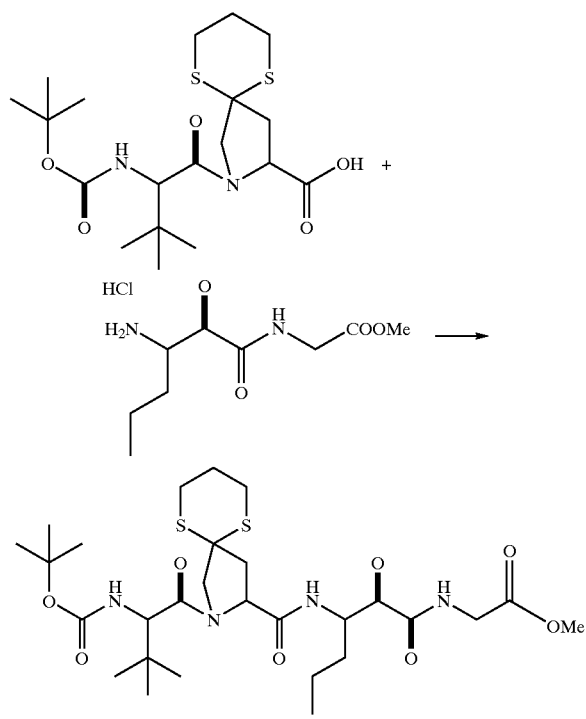

Follow the procedure of Example 1A but use the acid of Example Step 10B above and the amine of Example Step 1C to obtain the compound, $C_{28}H_{46}N_4O_8S_2$ (630.82) LRMS (FAB) M+H=631.4.

EXAMPLE 16

Step B

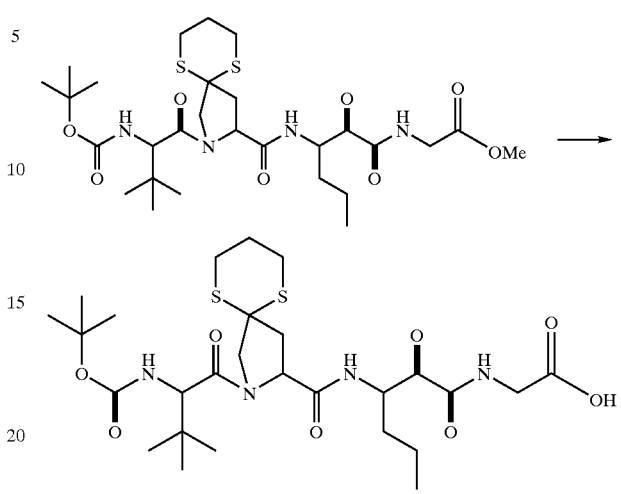

Follow the procedure of Example 1 Step E but use the ester of the preceding Step to obtain the compound, $C_{27}H_{44}N_4O_8S_2$ (616.79) LRMS (FAB) M+H=617.4.

EXAMPLE 16

Step C

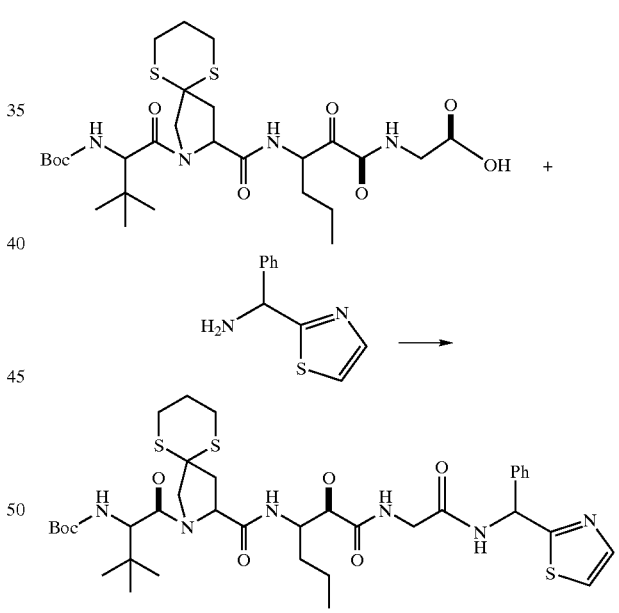

A stirred mixture of the product of the preceding Step (62 mg), the product of Example 7 Step D. (29 mg), HATU (57 mg, O-(7-azabenzotriazol-1-yl)-N,N,N',N'-tetramethyluronium hexafluorophosphate, Aldrich Chemical Co.) and $CH_2Cl_2$ (5 mL) at 0° C. was treated with diisopropylethylamine (0.023 mL), and the mixture was stirred an additional 3 hr. at room temperature. The mixture was poured into ice-cold EtOAc (50 mL) and washed successively with cold 5% aqueous $K_2CO_3$, cold 0.1 N HCl, and brine. The extract was dried over anhydrous $MgSO_4$, the mixture was filtered, the filtrate was evaporated in vacuo, and the residue was chromatographed (silica gel, 1:1 EtOAc:CH₂Cl₂). The crude product was triturated under (i-Pr)2O and filtered to leave the product as a white powder (81 mg), $C_{37}H_{52}N_6O_7S_3$ (789.04), LRMS (FAB) M+1= 789.4.

EXAMPLE 17

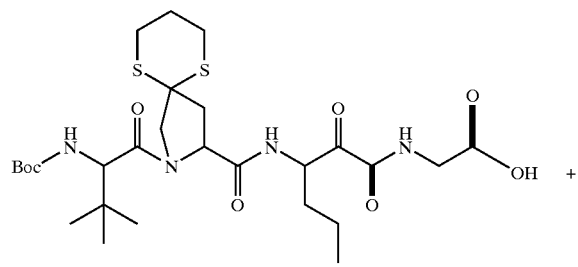

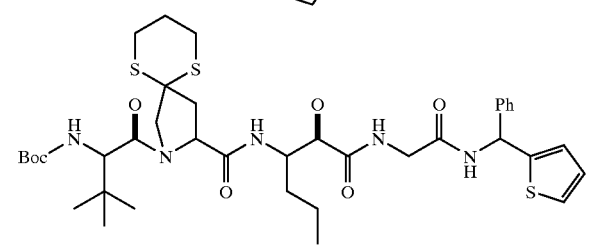

Following the procedure of Example of Example 16 Step C., the product of Example 16 Step B. was reacted with the product of Example 9 Step B. to obtain the corresponding product, $C_{38}H_{53}N_5O_7S_3$ (788.05), LRMS (FAB) M+1= 788.4.

EXAMPLE 18

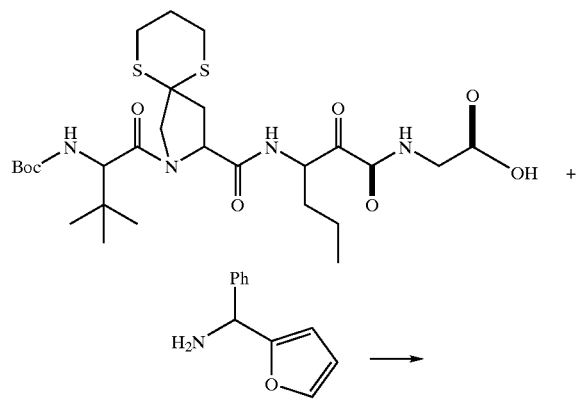

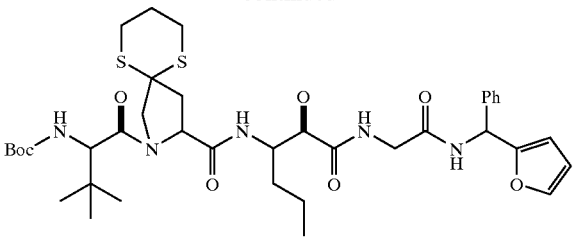

Following the procedure of Example of Example 16 Step C., the product of Example 16 Step B was reacted with the product of Example 9 Step B to obtain the corresponding product, $C_{38}H_{53}N_5O_7S_2$ (771.99), LRMS (FAB) M+1= 772.4.

EXAMPLE 19

Step A

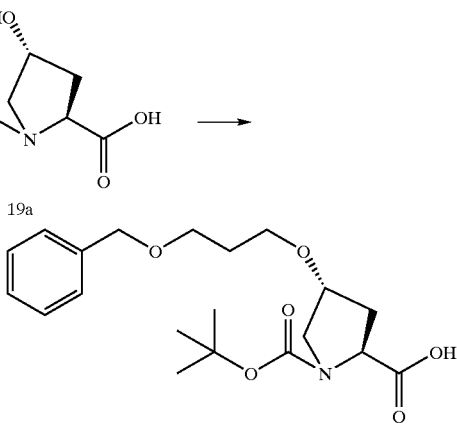

To a solution of Boc-Hyp-OH (7.0 g, 30.3 mmol) and benzyl 3-bromopropyl ether (7.8 g, 34.0 mmol) in anhydrous DMF (400 mL) at room temperature was added sodium hydride (3.5 g, 60% dispersion in mineral oil, 87.5 mmol) and sodium iodide (0.5 g, 3.33 mmols) with stirring. The resulting suspension was vigorously stirred at room temperature overnight (18 h). The reaction was quenched carefully with a slow addition of water (50 mL) and acidified with 6 N HCl solution (20 mL). After addition of ethyl acetate (800 mL), brine (150 mL) and more water (150 mL), the formed two layers were separated and the organic layer was washed with 5% $H_3PO_4$ (3×200 mL). It was then dried with MgSO₄, filtered and concentrated in vacuo to afford 19b as an oil which was used in Step B without further purification.

Step B

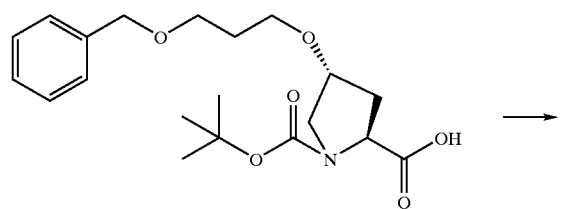

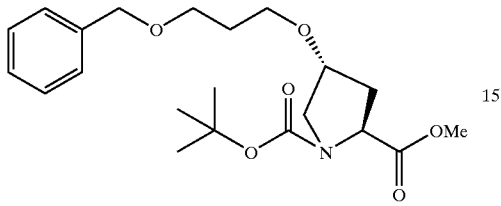

The acid 19b from Step A was dissolved in benzene (25 mL) and methanol (28 mL). To this solution at room temperature was added a solution of trimethylsilyl diazomethane (27 mL, 2.0 M in cyclohexane) with caution. After being stirred at room temperature for 1 h, it was concentrated in vacuo to yield the methyl ester. Flash chromatography (8 to 20% EtOAc-CH$_2$Cl$_2$) afforded 1c (5.15 g; 13.1 mmol, 43%, 2 steps) as an oil.

Step C

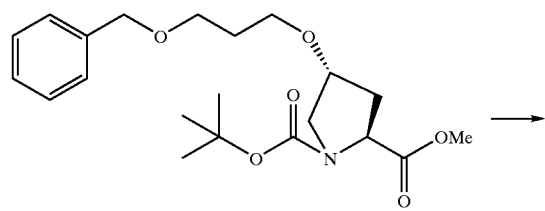

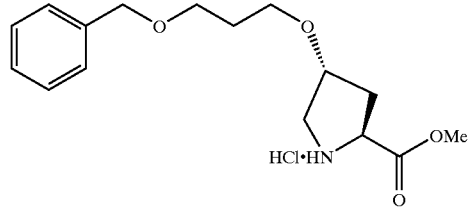

The Boc-amino methyl ester 19c (5.83 g, 14.8 mmol) was dissolved in 4 N HCl in dioxane (80 mL, 320 mmol) and the resulting solution was stirred at room temperature. The progress of the reaction was monitored by TLC. After 5 h, the solution was concentrated in vacuo and the residue was kept under vacuum overnight to yield a white solid which was used in the next coupling reaction without further purification.

Step D

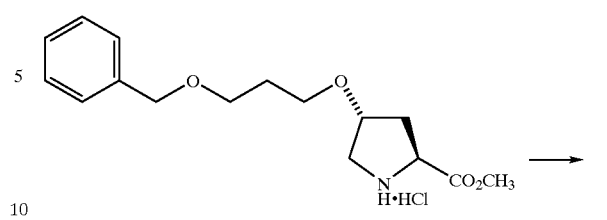

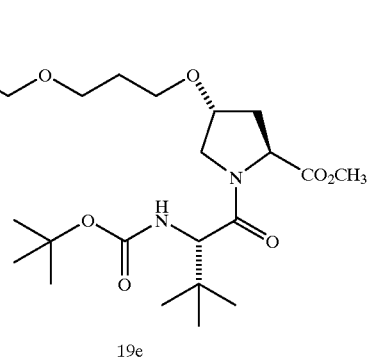

To a solution of the amine ester 19d (from Step 19B), N-Boc-tertbutylglycines as coupling partners 14.9 mmol), HOOBt (2.60 g, 15.9 mmol) and EDCl (3.41 g, 17.8 mmol) in anhydrous DMF (150 mL) and CH$_2$Cl$_2$ at −20° C., was added NMM (6.50 mL, 59.1 mmol). After being stirred at this temperature for 30 min, the reaction mixture was kept in a freezer overnight (18 h). It was then stirred in air and allowed to warm to room temperature in 1 h. EtOAc (450 mL), brine (100 mL) and 5% H$_3$PO$_4$ (100 mL) were added. The separated organic solution was washed with 5% H$_3$PO$_4$ (100 mL), saturated aqueous sodium bicarbonate solution (2×150 mL), water (150 mL), and brine (150 mL), dried with magnesium sulfate, filtered and concentrated in vacuo.

The material of 19e was purified by flash column chromatography using 90/10 dichloromethane/ethyl acetate to provide 12a in 73% yield. $^{13}$C NMR (mixture of rotamers, CDCl$_3$) 26.20, 28.31, 29.07, 30.06, 34.94, 35.86, 37.06, 51.21, 52.16, 52.84, 57.78, 58.33, 65.95, 66.92, 72.97, 75.48, 79.45, 127.55, 127.66, 128.35, 138.45, 155.62, 165.06, 171.13,172.54; HRMS (FAB) Calcd for C$_{27}$H$_{43}$N$_2$O$_7$: 507.3070 (M+H)$^+$. Found: 507.3077.

Step E

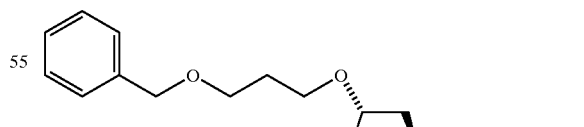

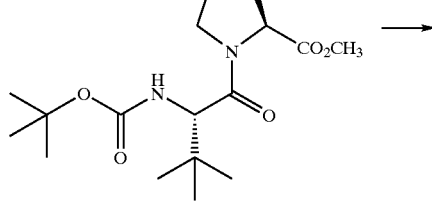

-continued

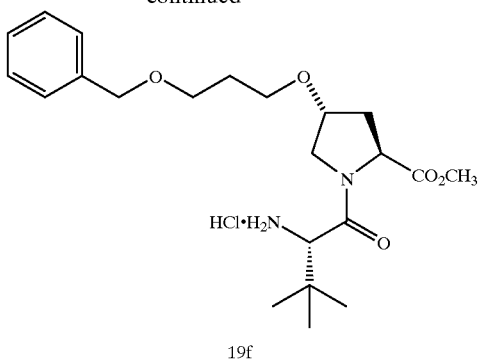

19f

The desired compound 19f was prepared as follows

The Boc-amino methyl ester 19e (6.53 g, 12.3 mmol) was dissolved in 4 N HCl (60 mL, 240 mmol) and the resulting solution was stirred at room temperature. The progress of the reaction was monitored by TLC. After 4 h, the solution was concentrated in vacuo and the residue was kept under vacuum overnight to give a white solid which was used in the next coupling reaction without further purification. The material was carried forward to the next step.

Step F

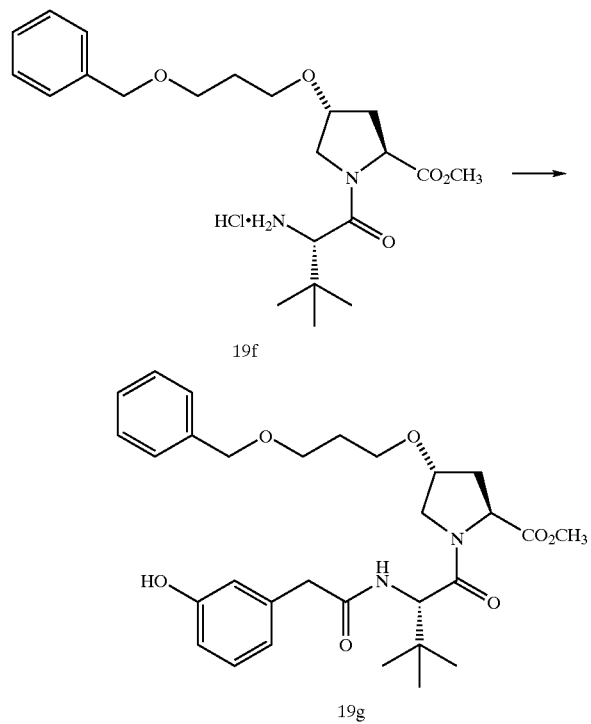

The desired product 19g was prepared as follows:

To a solution of the amine 19f (from Step 1D), 3-hydroxy phenylacetic acid (1.90 g, 12.5 mmol), HOOBt (2.10 g, 12.9 mmol) and EDCl (2.85 g, 14.9 mmol) in anhydrous DMF (250 mL) and CH$_2$Cl$_2$ (100 mL) at −20° C., was added NMM (4.20 mL, 38.2 mmol). After being stirred at this temperature for 30 min, the reaction mixture was kept in a freezer overnight (18 h). It was then stirred in air and allowed to warm to room temperature in 1 h. EtOAc (500 mL), brine (100 mL) and 5% H$_3$PO$_4$ (100 mL) were added.

The separated organic solution was washed with 5% H$_3$PO$_4$ (100 mL), saturated aqueous sodium bicarbonate solution (2×150 mL), water (150 mL), and brine (150 mL), dried with magnesium sulfate, filtered and concentrated in vacuo.

The material was purified by flash column chromatography using 99/1 dichloromethane/methanol to yield 19 g in 91%. $^{13}$C NMR (CDCl$_3$) δ 26.24, 29.93, 34.95, 35.96, 43.48, 52.18, 53.09, 57.06, 58.06, 66.10, 66.92, 72.93, 77.43, 114.59, 116.14, 120.87, 127.58, 127.64, 127.74, 128.37, 130.02, 135.95, 138.39, 156.90, 170.65, 171.06, 172.38; HRMS (FAB) Calcd for C$_{30}$H$_{41}$N$_2$O$_7$: 541.2914 (M+H)$^+$. Found: 541.2921.

Step G

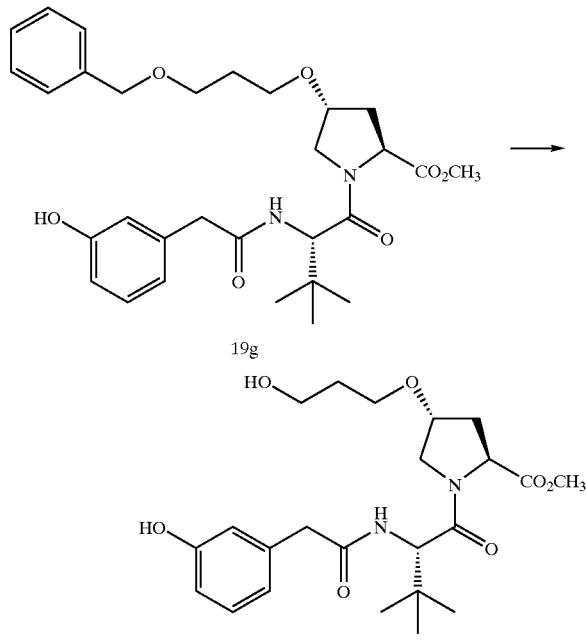

The desired product 19h was prepared as follows:

To a solution of the benzyl ether 19g (6.23 g, 11.0 mmol) in ethanol (200 mL) under nitrogen at room temperature was added 10% Pd—C (1.5 g) cautiously. The resulting suspension was vigorously stirred at room temperature under hydrogen for 23 h.

The product 19h obtained after filtering off the catalyst was pure enough for subsequent manipulations. $^{13}$C NMR (CDCl$_3$) δ 26.27, 32.09, 35.44, 35.67, 43.19, 52.21, 52.74, 57.60, 58.21, 58.75, 65.78, 77.74, 114.74, 116.02, 120.68, 130.07, 135.66, 157.11, 170.59, 172.05, 172.51; HRMS (FAB) Calcd for C$_{23}$H$_{35}$N$_2$O$_7$: 451.2444 (M+H)$^+$. Found: 451.2436.

Step H

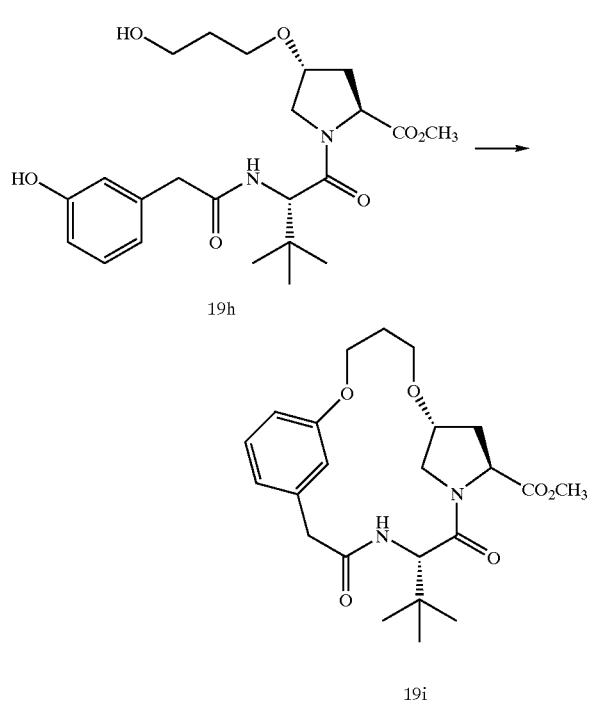

The desired product 19i was prepared as follows:

A solution of the phenol alcohol (9.43 mmol) and ADDP (6.60 g, 26.2 mmol) in anhydrous $CH_2Cl_2$ was bubbled with argon through a frit glass bubbler for 20 min. To this solution at 0° C. was added triphenylphosphine (4.10 g, 16.3 mmol). After stirring at 0° C. for 20 min, a second portion of triphenylphosphine (3.40 g, 13.5 mmol) was added. The solution was then warmed to room temperature and stirred overnight (24 h) under nitrogen until TLC indicated the complete consumption of the starting material.

The crude material was suspended in ethyl acetate/hexane (approx. 1/1) and the undissolved solid material was filtered off. Repeated this process once again, the filtrate was concentrated and applied on the column as a dichloromethane solution. The column was eluted with 75/25 hexane/acetone to yield 29% of 19i. HRMS (FAB) Calcd for $C_{23}H_{33}N_2O_6$: 433.2339 (M+H)$^+$. Found: 433.2339.

Step I

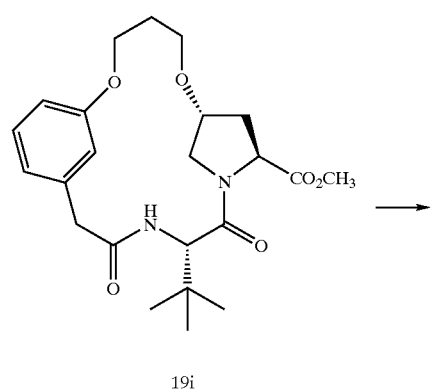

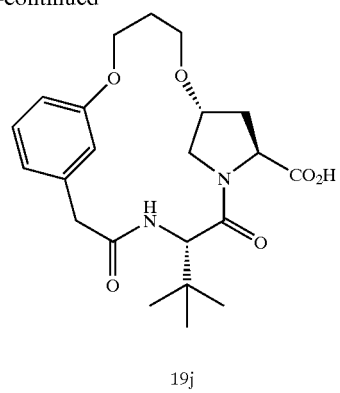

The desired compound 19j was prepared as follows in quantitative yields:

An aqueous lithium hydroxide solution (0.45 g in 30 mL $H_2O$) was added to a 0° C. solution of the methyl ester 19j in THF (30 mL) and methanol (30 mL). The mixture was stirred in an ice bath and warmed to room temperature along with it in 4 h. The progress of the reaction was monitored by TLC. After the volatiles were removed in vacuo, EtOAc (150 mL) and water (30 mL) were added and the two layers separated. The aqueous solution was extracted again with $CH_2Cl_2$ (150 mL), after which it was acidified to pH=1. EtOAc (200 mL) was then added and the aqueous solution was saturated with solid sodium chloride. After separation of the layers, the aqueous layer was extracted with EtOAc (2×150 mL). Organic solutions were combined, dried with magnesium sulfate, filtered and concentrated in vacuo to afford compound 19j.

$^1$H NMR (DMSO-d$_6$) δ 0.96 (s, 9H), 1.66–1.70 (m, 1 H), 1.75–1.82 (m, 2H), 2.43 (dd, 1H), 3.32–3.36 (m, 2H), 3.48–3.52 (m, 1H), 3.55 (dd, 1H), 3.84 (app. d, 1H), 3.99 (app. d, 1H), 4.06–4.10 (m, 3H), 4.16 (dd, 1H), 4.69 (d, 1H), 6.70–6.72 (m, 3H), 7.15 (app. t, 1H), 8.42 (d, 1H), 12.43 (br. s, 1 H); $^{13}$C NMR (DMSO-d$_6$) δ 26.25, 28.54, 33.31, 34.97, 41.22, 53.96, 56.11, 56.97, 63.36, 64.96, 76.84, 111.94, 115.25, 121.73, 129.13, 138.36, 158.27, 169.85, 170.15, 173.04; HRMS (FAB) Calcd for $C_{22}H_{31}N_2O_6$: 419.2182 (M+H)$^+$. Found: 419.2180.

EXAMPLE 20

Step A

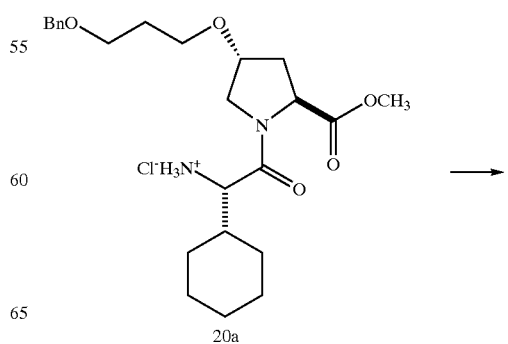

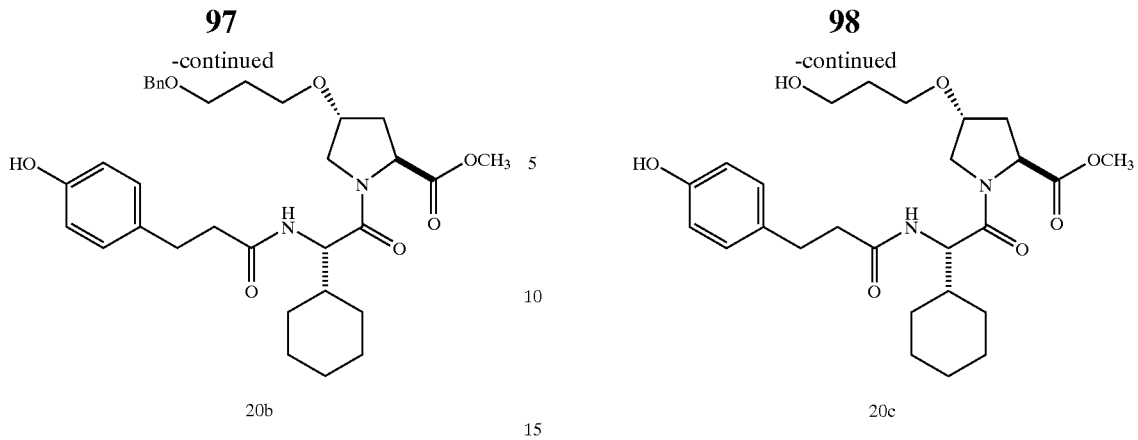

20b

The compound 20a was prepared as set forth in Scheme 9 referencing to Scheme 8.

The desired product 20b was prepared as follows:

To a solution of the amine 20a, 3-hydroxy phenylacetic acid (1.90 g, 12.5 mmol), HOOBt (2.10 g, 12.9 mmol) and EDCl (2.85 g, 14.9 mmol) in anhydrous DMF (250 mL) and CH$_2$Cl$_2$ (100 mL) at −20° C., was added NMM (4.20 mL, 38.2 mmol). After being stirred at this temperature for 30 min, the reaction mixture was kept in a freezer overnight (18 h). It was then stirred in air and allowed to warm to room temperature in 1 h. EtOAc (500 mL), brine (100 mL) and 5% H$_3$PO$_4$ (100 mL) were added. The separated organic solution was washed with 5% H$_3$PO$_4$ (100 mL), saturated aqueous sodium bicarbonate solution (2×150 mL), water (150 mL), and brine (150 mL), dried with magnesium sulfate, filtered and concentrated in vacuo.

The material was purified by flash column chromatography using EtOAc/Hex (7:3) to yield 64a in 80%.; $^1$H NMR (CDCl$_3$, δ): 7.35–7.29 (m, 5 H), 7.02 (d, 2 H, J=8.4 Hz), 6.72 (d, 2 H, J=6.9Hz) 6.01 (d, 1 H), 4.60 (t, 1 H), 4.52 (s, 1 H), 3.8–3.61 (m, 2 H), 3.72 (s, 3 H), 3.54–3.51 (m, 4 H), 2.83 (t, 2 H, J=7.5 Hz), 2.39 (t, 2 H, J=8.1 Hz) 2.41–2.20 (m, 1 H), 2.05–1.83 (m, 1 H), 1.85–1.58 (m, 8 H), 1.26–1.24 (m, 5 H); $^{13}$C NMR (CDCl$_3$, δ): 172.2, 171.9, 171.0, 154.4, 138.3, 132.2, 129.4, 128.4, 127.7, 127.6, 115.4, 73.0, 66.9, 66.2, 57.9, 54.9, 52.5, 52.3, 41.0, 38.5, 34.7, 30.8, 30.0, 29.4, 27.9, 26.1, 26.0, 25.9.

Step B

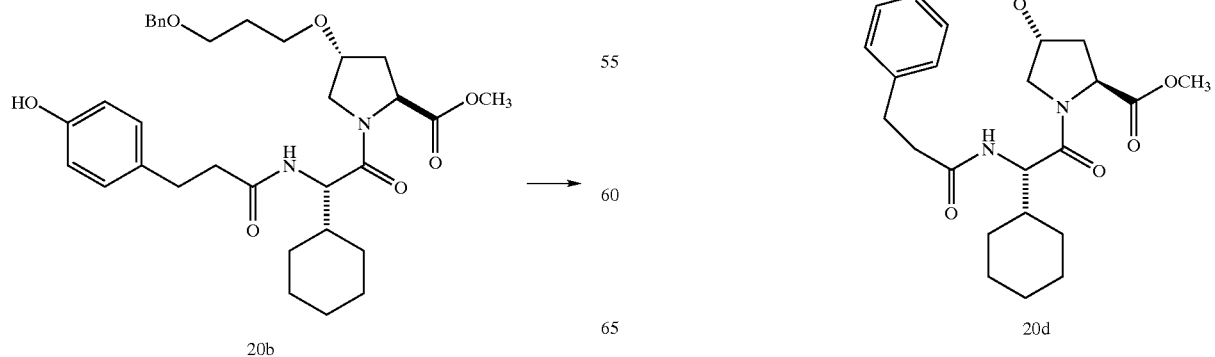

20b

The desired product 20c was obtained as follows:

To a solution of 20c (11.0 mmol) in ethanol (200-ml) under nitrogen at room temperature was added 10% Pd/C (1.5 g) cautiously. The resulting suspension was vigorously stirred at room temperature under hydrogen for 23 h.

Step C

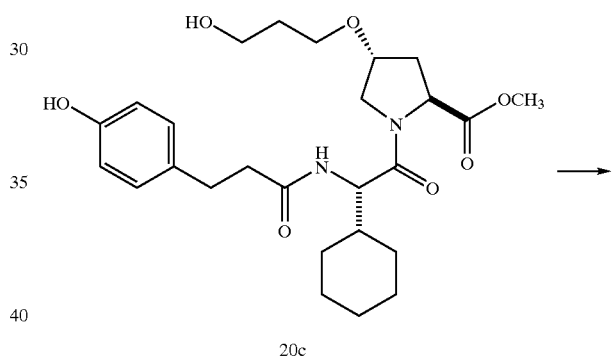

20c

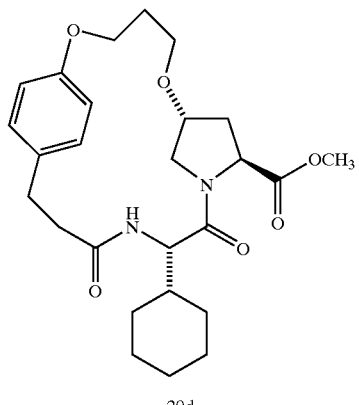

20d

The desired product 20d was obtained as follows:

A solution of 20d (9.43 mmol) and ADDP (6.60 g, 26.2 mmol) in anhydrous $CH_2Cl_2$ was bubbled with argon through a frit glass bubbler for 20 min. To this solution at 0° C. was added triphenylphosphine (4.10 g, 16.3 mmol). After stirring at 0° C. for 20 min, a second portion of triphenylphosphine (3.40 g, 13.5 mmol) was added. The solution was then warmed to room temperature and stirred overnight (24 h) under nitrogen until TLC indicated the complete consumption of the starting material.

The crude reaction mixture was purified by $SiO_2$ gel chromatography (acetone/Hexanes 3:7) to yield 64c (64 mg, 16%) as a colorless solid.; $^{13}C$ NMR (CDCl$_3$) δ 172.1, 171.1, 171.0, 157.7, 131.0 129.9, 114.3, 78.1, 64.7, 63.3, 58.7, 55.3, 52.2, 52.0, 42.1, 37.9, 36.1, 30.8, 30.7, 29.7, 28.7, 28.5, 26.2, 26.0; MS (FAB) 473 (M+1)$^+$, (100), 327 (20).

Step D

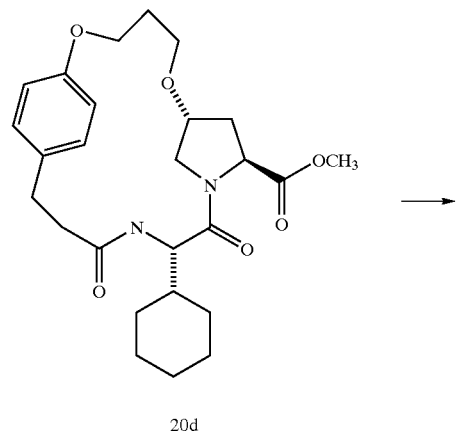

20d

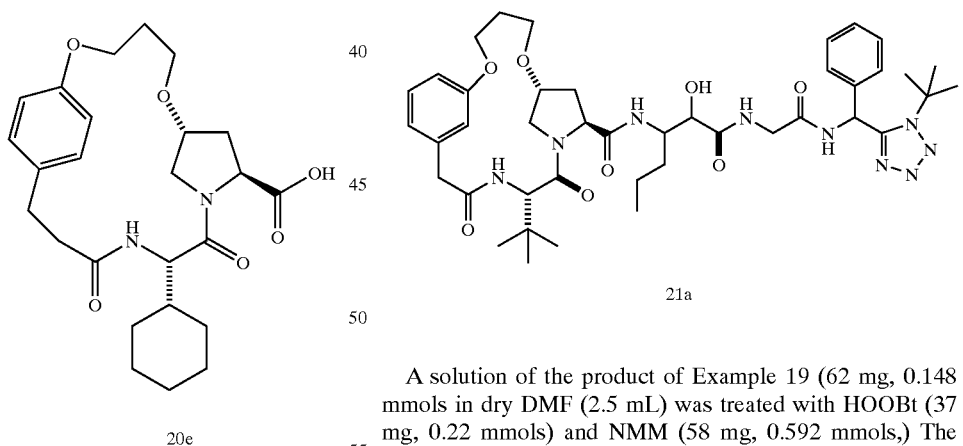

20e

The acid 20e was synthesized as follows:

An aqueous sodium hydroxide solution (0.45 g in 30 ml $H_2O$) was added to a 0° C. solution of compound 20e in THF (30 ml) and methanol (30 ml). This mixture was stirred in an ice bath and warmed to room temperature along with it in 4 h. The progress of the reaction was monitored by TLC. After the volatiles were removed in vacuo, EtOAc (150 ml) and water (30 ml) were added and the two layers separated. The aqueous solution was saturated with solid sodium chloride. After separation of the layers, the aqueous layer was extracted with EtOAc (2×150 ml). Organic solutions were combined, dried with magnesium sulfate, filtered and concentrated in vacuo to afford compound 20e.

EXAMPLE 21

Step A

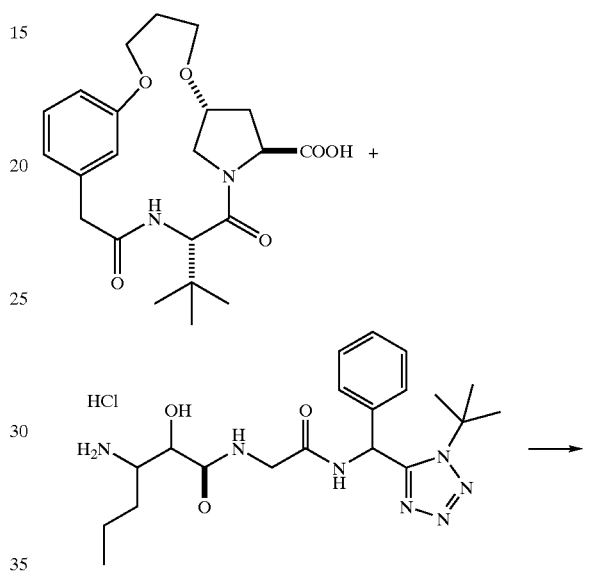

21a

A solution of the product of Example 19 (62 mg, 0.148 mmols in dry DMF (2.5 mL) was treated with HOOBt (37 mg, 0.22 mmols) and NMM (58 mg, 0.592 mmols,) The reaction mixture was cooled to 0° C. and treated with EDCl (63 mg, 0.33 mmols, 1.5 equiv) and stirred for 20 min. The reaction mixture was treated with the product of Example [11Q2] step B (74 mg, 0.0.16 mmols,) and stirred at rt for 48 h. The reaction mixture was concentrated in vacuo and diluted with $H_2O$ (30 mL). The aqueous layer was extracted with $CH_2Cl_2$ (3×50 mL) and EtOAc(3×50 mL). The combined organic layers were extracted with aq. HCl (2M), aq. NaOH (2M), dried ($Na_2SO_4$) filtered concentrated in vacuo to obtain a colorless solid (120 mg) which was used for oxidation. MS: (Electron spray, m/z rel int): 818 [(M+1$^+$, 100].

Step B

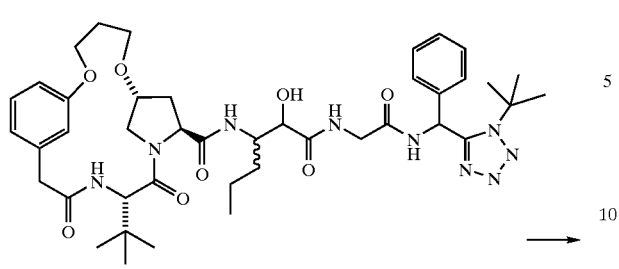

21a

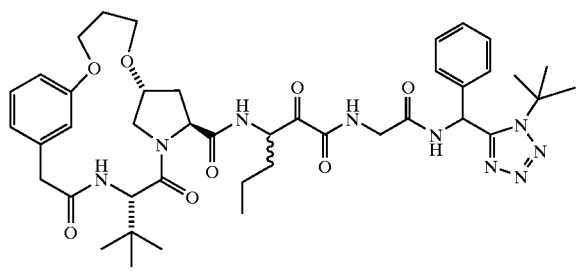

A solution of the product of the preceding step (130 mg, 0.16 mmols) in $CH_2Cl_2$ (2.0 mL) was treated with Dess-Martin reagent (mg, 0.32 mmol, 2.0 equiv.). The reaction mixture was stirred at room temperature for 2 h and the mixture was concentrated in vacuo. The residue was purified by preparative TLC ($SiO_2$, $CH_3OH/CH_2Cl_2$ 1:49) to yield oxidized product (55 mg, 42%) as a colorless solid. MS: (Electron spray, m/z rel int): 816 [$(M+1)^+$, 100].

EXAMPLE 22

Step A

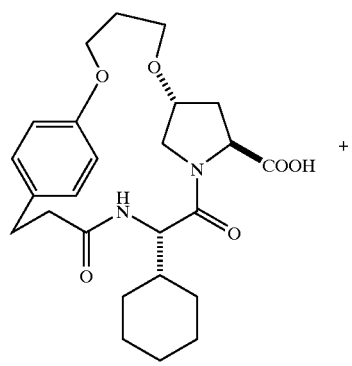 +

-continued

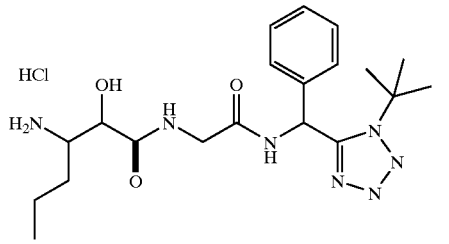

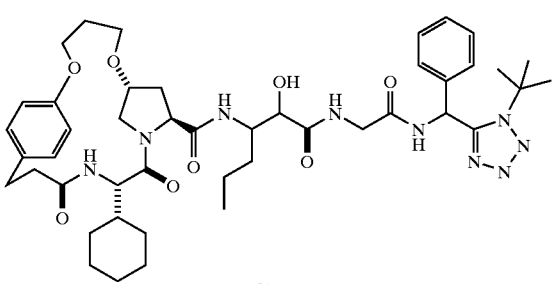

21a

Following the procedure of Example 21 Step A, the product of Example 20, labeled 20e is reacted with the product of Example 13 Step B to afford the corresponding compound as a colorless solid product which was used for oxidation; MS: [electron spray, m/z(rel int)] 858 [$(M+1)^+$, 100], 604 (10), 446 (10).

EXAMPLE 23

Step B

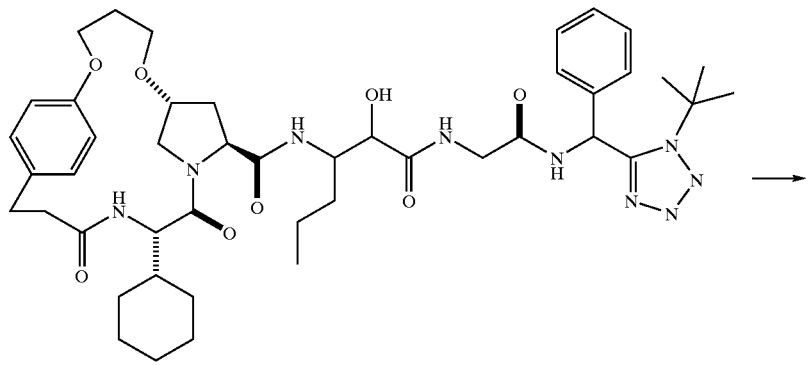

-continued

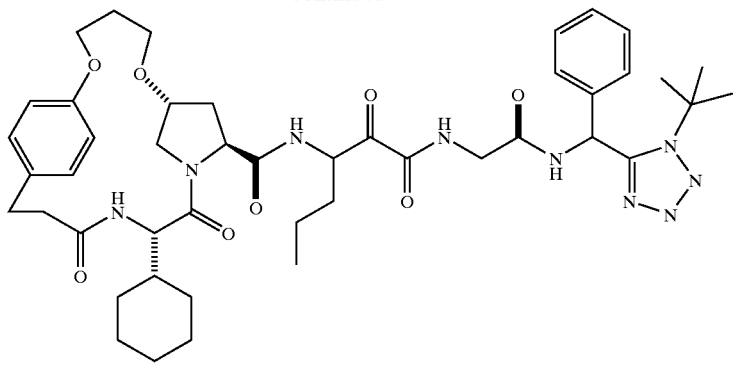

Following the procedure of Example 21 Step B., the product of the preceding Step was converted to the corresponding product as a colorless solid. MS: [electron spray, m/z(rel int)] 856 [(M+1)$^+$, 100].

Assay for HCV Protease Inhibitory Activity:
Spectrophotometric Assay:

Spectrophotometric assay for the HCV serine protease was performed on the inventive compounds by following the procedure described by R. Zhang et al, *Analytical Biochemistry*, 270 (1999) 268–275, the disclosure of which is incorporated herein by reference. The assay based on the proteolysis of chromogenic ester substrates is suitable for the continuous monitoring of HCV NS3 protease activity. The substrates were derived from the P side of the NS5A-NS5B junction sequence (Ac-DTEDWX(Nva), where X=A or P) whose C-terminal carboxyl groups were esterified with one of four different chromophoric alcohols (3- or 4-nitrophenol, 7-hydroxy-4-methyl-coumarin, or 4-phenylazophenol). Presented below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UVNIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation: Recombinant heterodimeric HCV NS3/NS4A protease (strain 1a) was prepared by using the procedures published previously (D. L. Sali et al, *Biochemistry*, 37 (1998) 3392–3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 μM EDTA and 5 μM DTT) utilizing a Biorad Bio-Spin P-6 prepacked column.

Substrate Synthesis and Purification: The synthesis of the substrates was done as reported by R. Zhang et al, (ibid.) and was initiated by anchoring Fmoc-Nva-OH to 2-chlorotrityl chloride resin using a standard protocol (K. Barlos et al, *Int. J. Pept. Protein Res.*, 37 (1991), 513–520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous Na$_2$CO$_3$ solution) to remove the acid used in cleavage. The DCM phase was dried over Na$_2$SO$_4$ and evaporated.

The ester substrates were assembled using standard acid-alcohol coupling procedures (K. Holmber et al, *Acta Chem. Scand.*, B33 (1979) 410–412). Peptide fragments were dissolved in anhydrous pyridine (30–60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) was added to initiate the coupling reactions. Product formation was monitored by HPLC and found to be complete following 12–72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20–30%. The molecular mass was confirmed by electrospray ionization mass spectroscopy. The substrates were stored in dry powder form under desiccation.

Spectra of Substrates and Products: Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD−substrate OD)/substrate OD).

Protease Assay: HCV protease assays were performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sali et al, ibid.)). Typically, 150 µl mixtures of buffer, substrate and inhibitor were placed in wells (final concentration of DMSO 4% v/v) and allowed to preincubate at 30° C. for approximately 3 minutes. Fifty µls of pre-warmed protease (12 nM, 30° C.) in assay buffer, was then used to initiate the reaction (final volume 200 µl).The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6–200 µM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators: The inhibition constants ($K_i$) for the competitive inhibitors of Table A were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i=1+[I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m)$, was used to calculate the $K_i$ value.

The obtained $K_i$ values for various compounds of the present invention are given in the afore-mentioned Table wherein the compounds have been arranged in the order of ranges of $K_i$ values. From these test results, it would be apparent to the skilled artisan that the compounds of the invention have excellent utility as NS3-serine protease inhibitors.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

TABLE A

Serine Protease Inhibitory Activity

| Ex. | structure | MolWt. | HCV Assay Range Ki* (nM) |
|---|---|---|---|
| I | 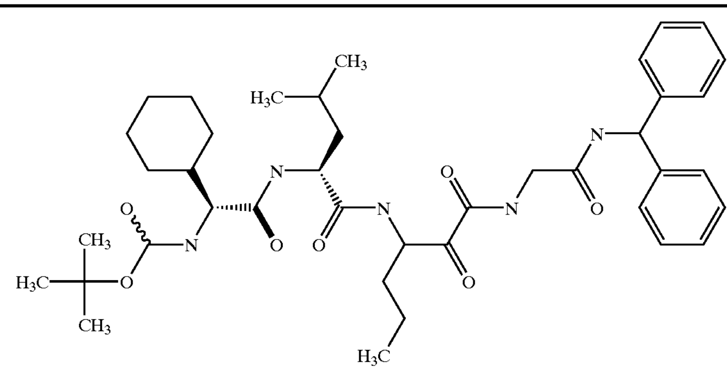 | 719.93 | d |
| II | 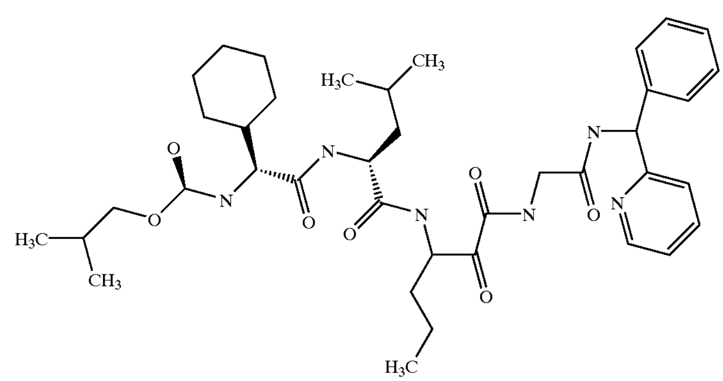 | 720.92 | c |

TABLE A-continued
Serine Protease Inhibitory Activity
| Ex. | structure | MolWt. | HCV Assay Range Ki* (nM) |
|---|---|---|---|
| III | 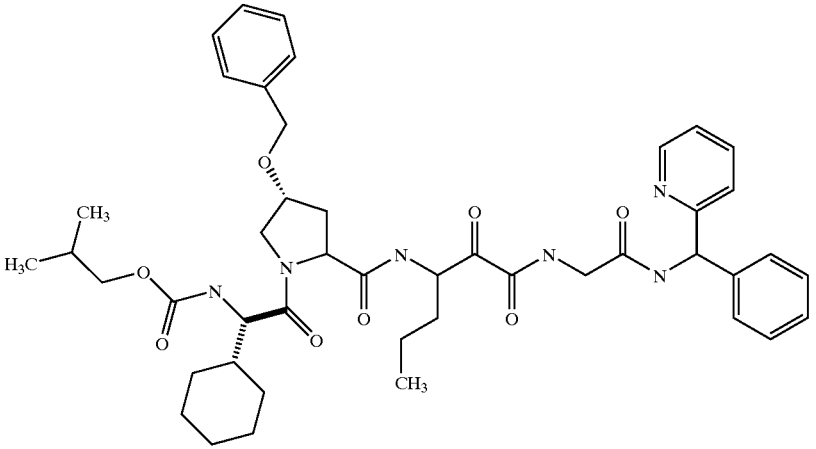 | 811.00 | b |
| IV | 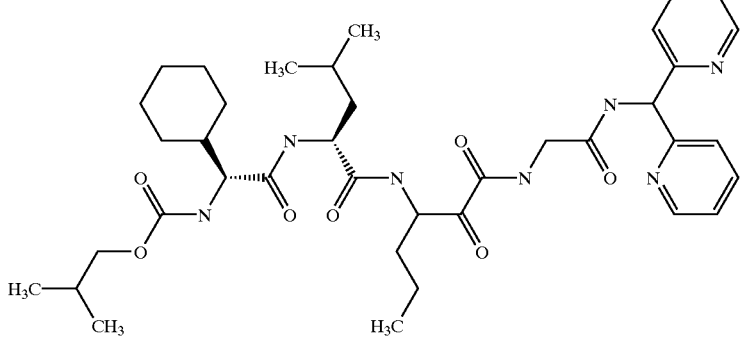 | 721.90 | c |
| V | 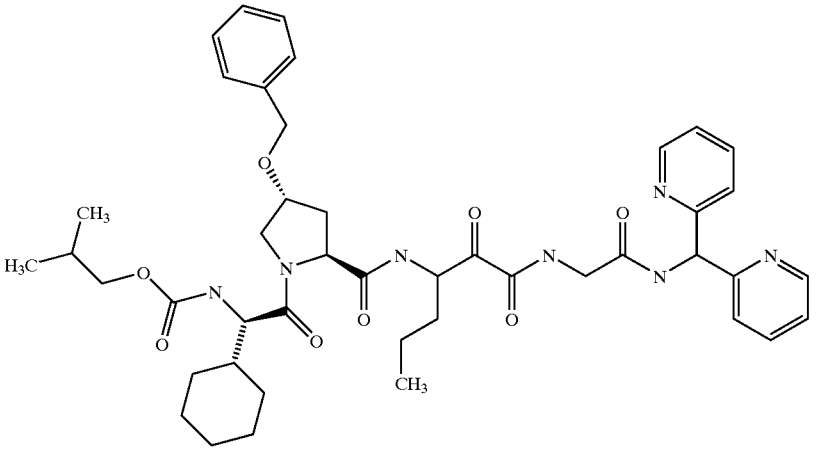 | 811.99 | b |

TABLE A-continued

Serine Protease Inhibitory Activity

| Ex. | structure | MolWt. | HCV Assay Range Ki* (nM) |
|---|---|---|---|
| VI | 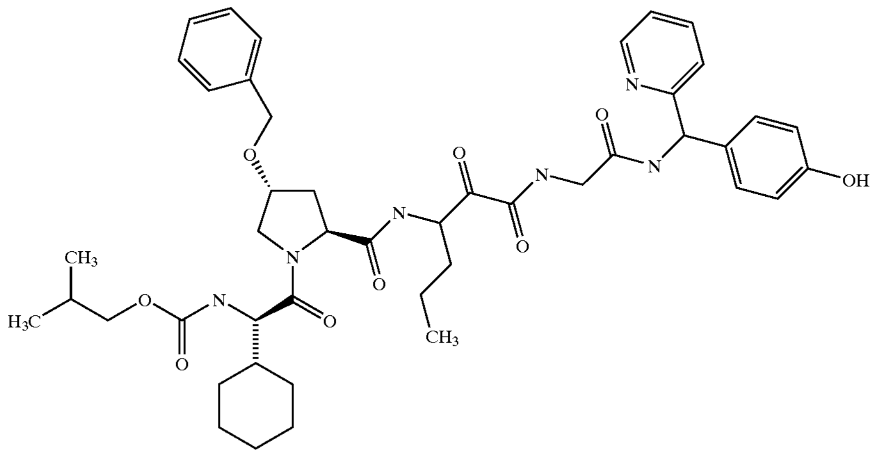 | 827.00 | c |
| VII | 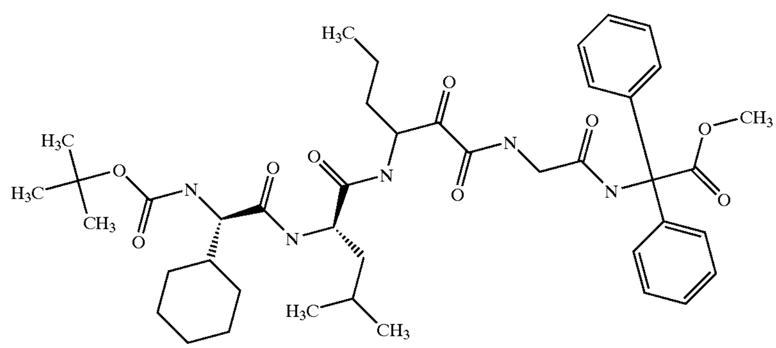 | 777.97 | c |
| VIII | 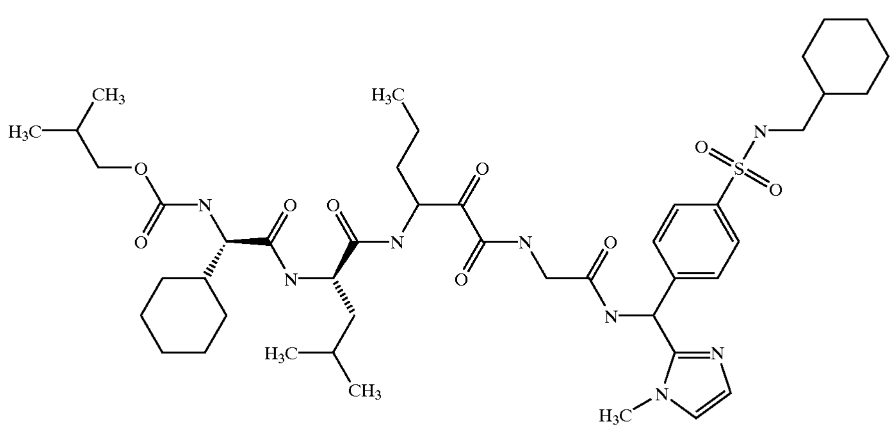 | 899.17 | d |

TABLE A-continued

Serine Protease Inhibitory Activity

| Ex. | structure | MolWt. | HCV Assay Range Ki* (nM) |
|---|---|---|---|
| IX | 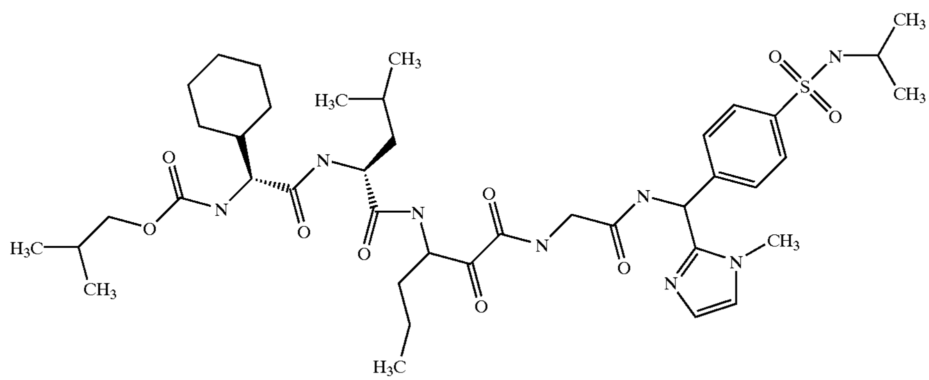 | 845.08 | c |
| X | 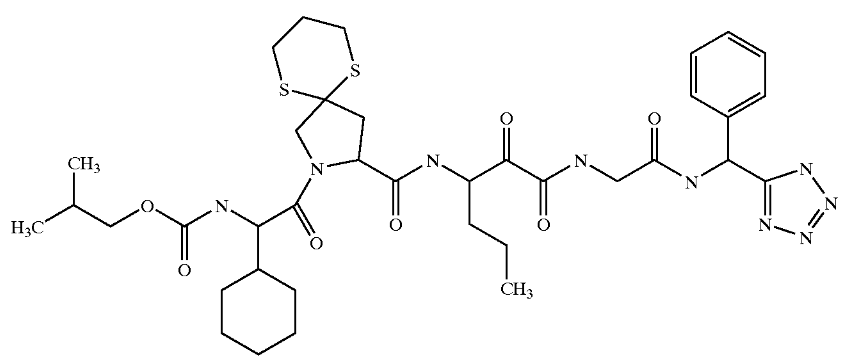 | 800.02 | a |
| XI | 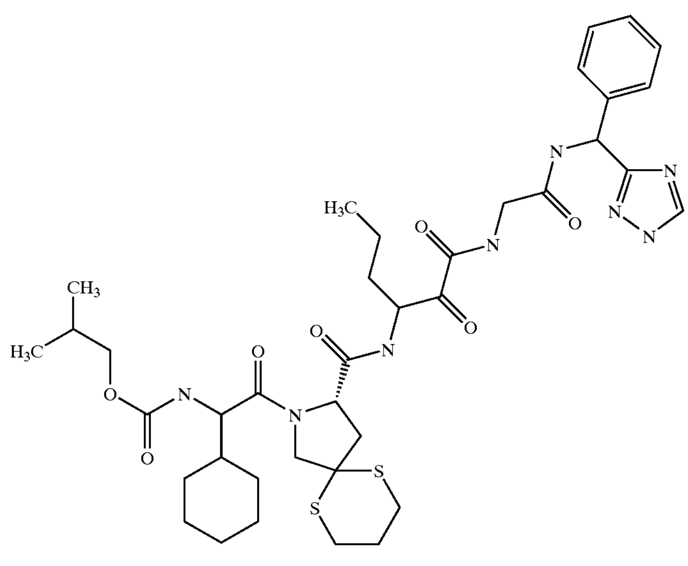 | 799.03 | b |

TABLE A-continued

Serine Protease Inhibitory Activity

| Ex. | structure | MolWt. | HCV Assay Range Ki* (nM) |
|---|---|---|---|
| XII | | 772.99 | a |
| XIII | | 772.99 | b |

TABLE A-continued
Serine Protease Inhibitory Activity
| Ex. | structure | MolWt. | HCV Assay Range Ki* (nM) |
|---|---|---|---|
| XIV | 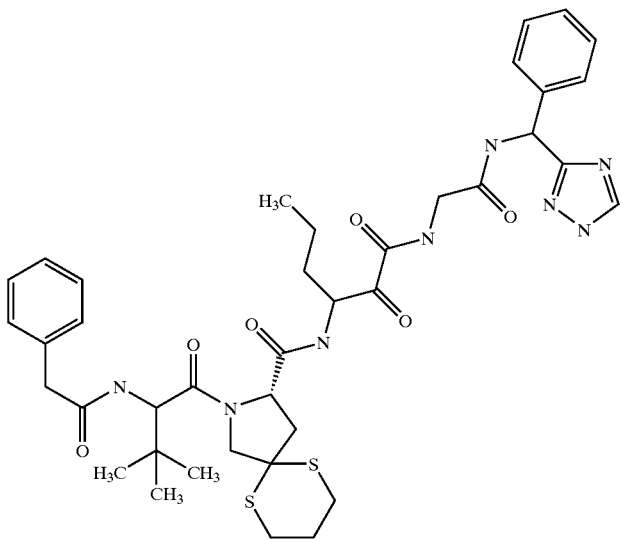 | 791.01 | b |
| XV | 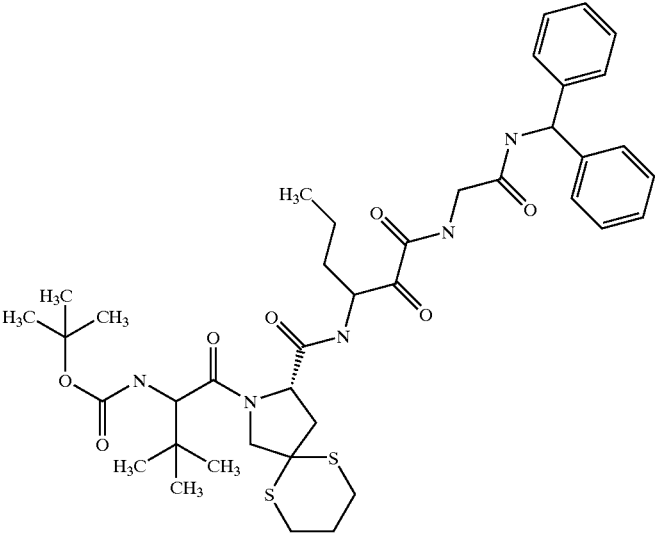 | 782.04 | b |

TABLE A-continued

Serine Protease Inhibitory Activity

| Ex. | structure | MolWt. | HCV Assay Range Ki* (nM) |
|---|---|---|---|
| XVI | 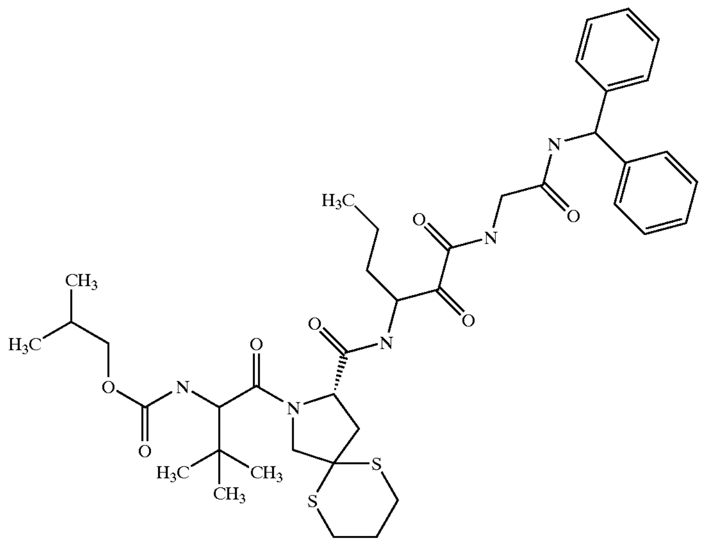 | 782.04 | b |
| XVII | 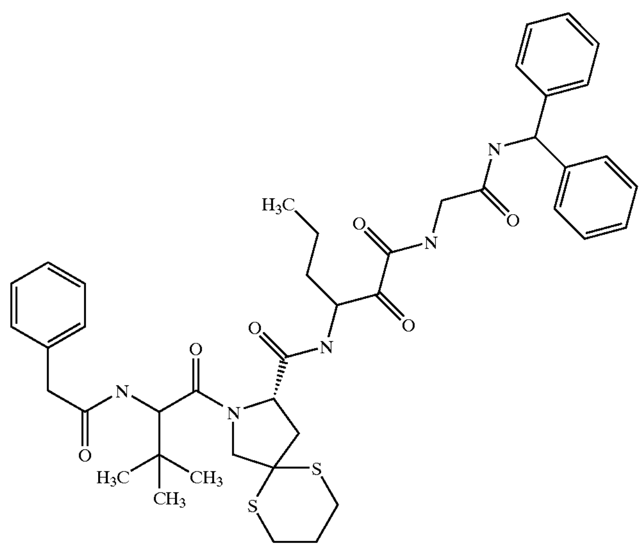 | 800.06 | b |
| XVIII | 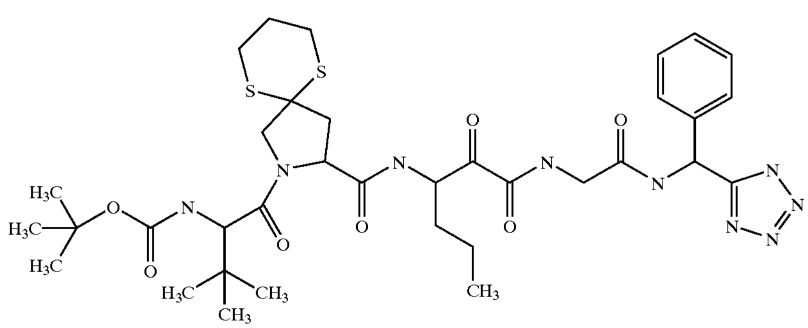 | 773.98 | b |

TABLE A-continued
Serine Protease Inhibitory Activity
| Ex. | structure | MolWt. | HCV Assay Range Ki* (nM) |
|---|---|---|---|
| XIX | 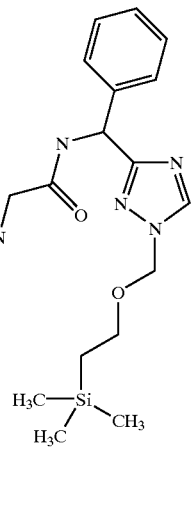 | 903.26 | c |
| XX | 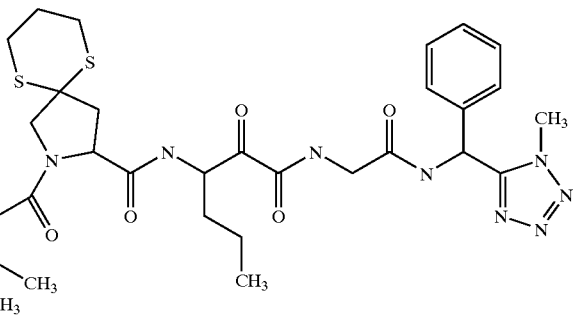 | 788.01 | b |
| XXI | 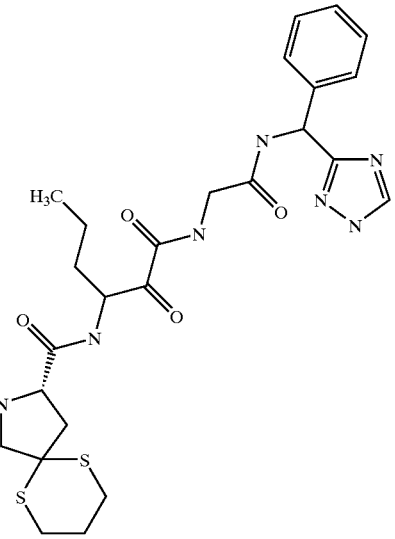 | 772.99 | a |

TABLE A-continued
Serine Protease Inhibitory Activity
| Ex. | structure | MolWt. | HCV Assay Range Ki* (nM) |
|---|---|---|---|
| XXII | 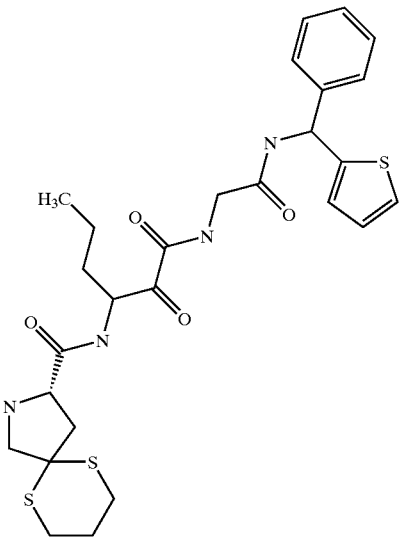 | 788.07 | b |
| XXIII | 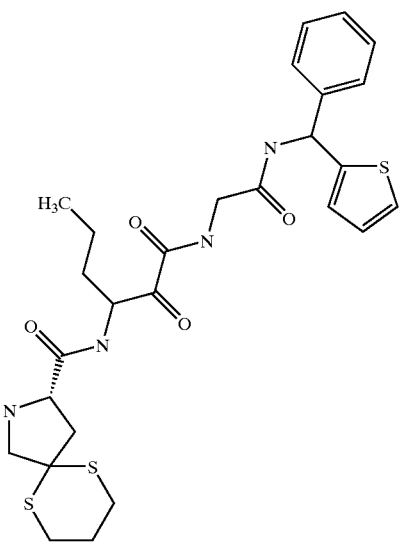 | 788.07 | c |

TABLE A-continued
Serine Protease Inhibitory Activity
| Ex. | structure | MolWt. | HCV Assay Range Ki* (nM) |
|---|---|---|---|
| XXIV | 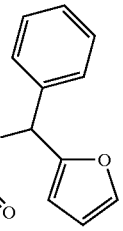 | 772.00 | b |
| XXV | 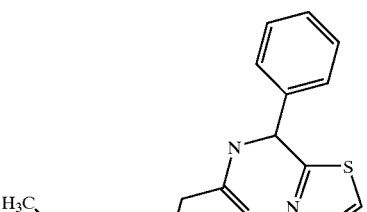 | 789.05 | b |
| XXVI | 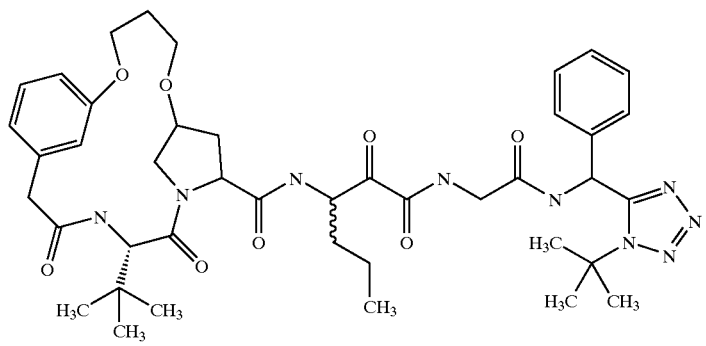 | 815.98 | b |

TABLE A-continued

Serine Protease Inhibitory Activity

| Ex. | structure | MolWt. | HCV Assay Range Ki* (nM) |
|---|---|---|---|
| XXVII | 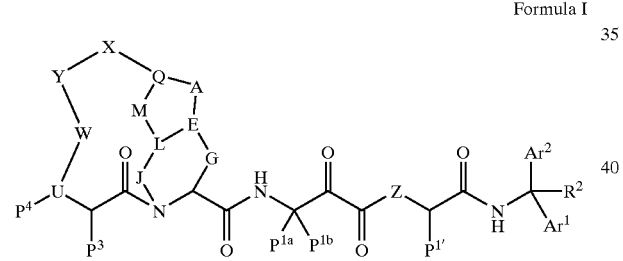 | 830.01 | c |

HCV Assay Ki* range: Category a = 10–99 nM; b = 100–999 nM; c = 1000–9999 nM; d = 10,000–50,000 nM

What is claimed is:

1. A compound, including enantiomers, stereoisomers, rotomers and tautomers of said compound, and pharmaceutically acceptable salts, solvates or derivatives thereof, with said compound having the general structure shown in Formula I:

Formula I wherein:

X and Y are independently selected from the moieties: alkyl, alkyl-aryl alkyl ether, alkyl-aryl ether, or aryl ether, with the proviso that X and Y may optionally be additionally substituted with $X^{11}$ or $X^{12}$;

$X^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

W may be present or absent, and if W is present, W is C=O;

Q may be present or absent, and when Q is present, Q is CH, N, P, $(CH_2)_p$, $(CHR)_p$, $(CRR')_p$, O, RNR, S, or $SO_2$; and when Q is absent, M is also absent, A is directly linked to X;

A is O, $CH_2$, $(CHR)_p$, $(CHR-CHR')_p$, $(CRR')_p$, NR, S, $SO_2$ or a bond;

U is N

E is CH, N or CR, or a double bond towards A, L or G;

G may be present or absent, and when G is present, G is $(CH_2)_p$, $(CHR)_p$, or $(CRR')_p$; and when G is absent, J is present and E is directly connected to the carbon atom where G was connected to;

J may be absent or present, and when J is present, J is $(CH_2)_p$, $(CHR)_p$, or $(CRR')_p$, $SO_2$, NH, NR or O; and when J is absent, G is present and L is directly linked to nitrogen;

L may be present or absent, and when L is present, L is CH, CR, O, S or NR; and when L is absent, then M may be absent or present, and if M is present with L being absent, then M is directly and independently linked to E, and J is directly and independently linked to E;

M may be present or absent, and when M is present, M is O, NR, S, $SO_2$, $(CH_2)_p$, $(CHR)_p$, $(CHR-CHR')_p$, or $(CRR')_p$;

p is a number from 0 to 6;

R and R' are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, cyano, nitro; (cycloalkyl)-alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkylheteroaryl; with said alkyl, heteroalkyl, alkenyl, heteroalkenyl, aryl, heteroaryl, cycloalkyl and heterocycloalkyl moieties may be optionally substituted, with said term "substituted" referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, cyano, nitro, sulfonamido; and $P^{1a}$, $P^{1b}$, $P^{1'}$ and $P^3$ are independently selected from:
H; C1–C10 straight or branched chain alkyl; or C3–C8 cycloalkyl,
wherein said alkyl, alkenyl, cycloalkyl, heterocyclyl; (cycloalkyl)alkyl and (heterocyclyl)alkyl moieties may be optionally substituted with R",
R" is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from R''';
Z is NH;
$Ar^1$ and $Ar^2$ are independently selected from phenyl; 2-pyridyl, 3-pyridyl, 4-pyridyl or their corresponding N-oxides; 2-thiophenyl; 3-thiophenyl; 2-furanyl; 3-furanyl; 2-pyrrolyl; 3-pyrrolyl; 2-imidazolyl; 3(4)-imidazolyl; 3-(1,2,4-triazolyl); 5-tetrazolyl; 2-thiazolyl; 4-thiazolyl; 2-oxazolyl; or 4-oxazolyl; either or both of which may be optionally substituted with $R^1$;
$R^1$ is H, halogen, cyano, nitro, $CF_3$, $Si(alkyl)_3$, straight-chain or branched lower alkyl, alkenyl, alkynyl, cycloalkyl, cycloalkyl-alkyl, aryl, alkylaryl, arylalkyl, heteroaryl, hydroxy, alkoxy, aryloxy, alkoxycarbonyloxy, (alkylamino)carbonyloxy, mercapto, alkylthio, arylthio, alkylsulfinyl, heterocyclylsulfinyl, arylsulfinyl, heteroarylsulfinyl, alkylsulfonyl, heterocyclylsulfonyl, arylsulfonyl, heteroarylsulfonyl, alkylcarbonyl arylcarbonyl, carboxy, alkoxycarbonyl, aryloxycarbonyl, heteroaryloxycarbonyl, alkyaminocarbonyl, arylaminocarbonyl, amino, alkylamino, arylamino, alkylsulfonamide, arylsulfonamide, alkoxycarbonylamino, alkylureido, or arylureido;
$P^4$ is H; and
$R^2$ is H, or alkoxycarbonyl.

2. The compound according to claim 1, wherein $R^2$ is H, U is N and $P^4$ is H.

3. The compound according to claim 1, wherein $A^1$ and $Ar^2$ are independently selected from the group consisting of phenyl, 2-thiophenyl, 2-furanyl, 3-furanyl, 3(4)-imidazolyl, 3-(1,2,4-triazolyl), 5-tetrazolyl, or 2-thiazolyl.

4. The compound according to claim 3, wherein $Ar^2$ is phenyl and $Ar^1$ is selected from the group consisting of 3-(1,2,4-triazolyl),5-tetrazolyl, or 2-thiazolyl and U is N and $P^4$ is H.

5. The compound according to claim 1 or claim 3, wherein $R^1$ is H, $CF_3$, $CH_3$, alkyl or alkenyl.

6. The compound according to claim 3, wherein $R^1$ is H, $CF_3$, $CH_3$, alkyl or alkenyl.

7. The compound according to claim 1, wherein $P^{1'}$ is H or $CH_3$.

8. The compound according to claim 1, wherein $P^{1'}$ is H such that $P^{1'}$ the adjacent nitrogen and carbonyl moieties correspond to the residuum of a glycine unit.

9. The compound of claim 3, wherein $P^{1a}$ end $P^{1b}$ are independently selected from the group consisting of the following moieties:

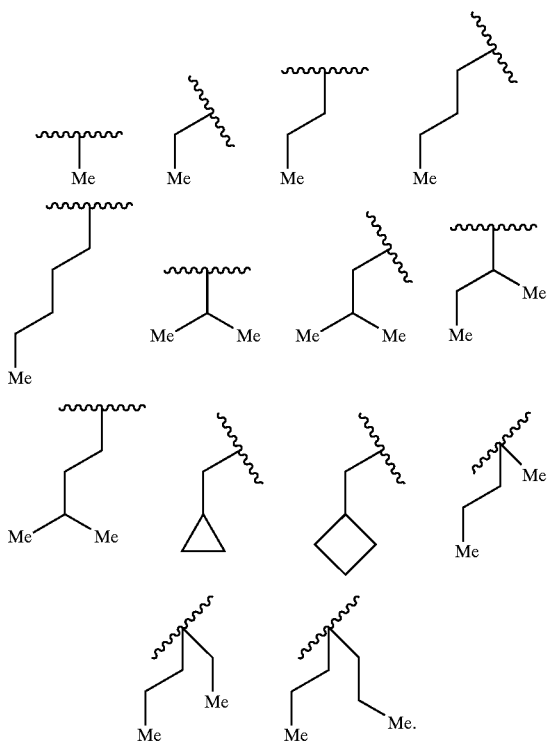

10. The compound according to claim 3, wherein $P^3$ is selected from the group consisting of:

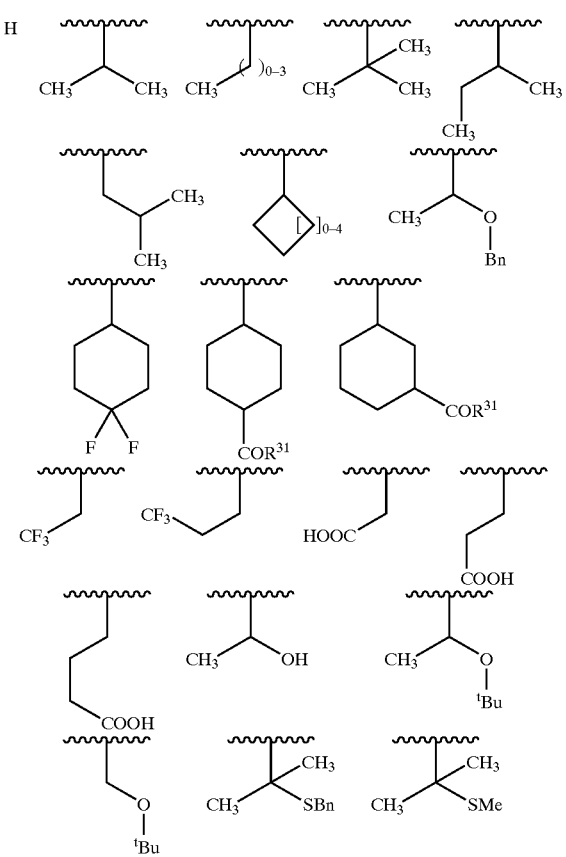

-continued

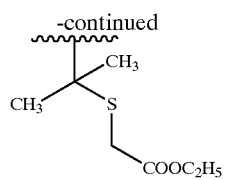

wherein $R^{31}$=OH or O-alkyl.

11. The compound of claim 3, wherein $P^3$ is selected from the group consisting of the following moieties:

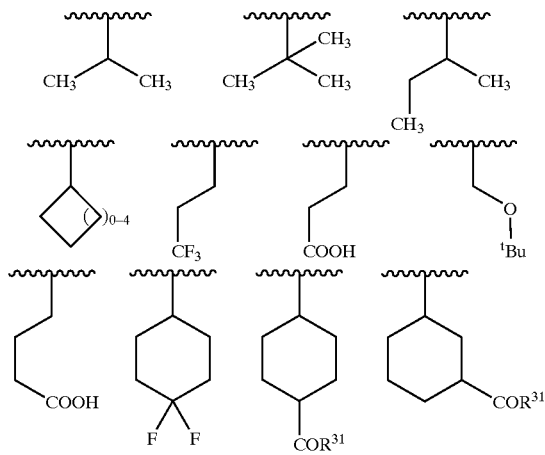

wherein $R^{31}$ =OH or O-alkyl.

12. The compound of claim 1, wherein the moiety:

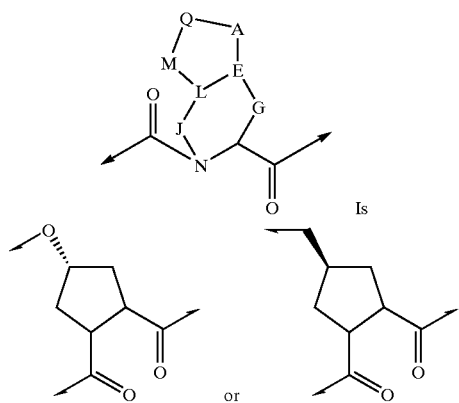

13. The compound according to claim 1, wherein said compound is selected from the group consisting of compounds having the structural formulae:

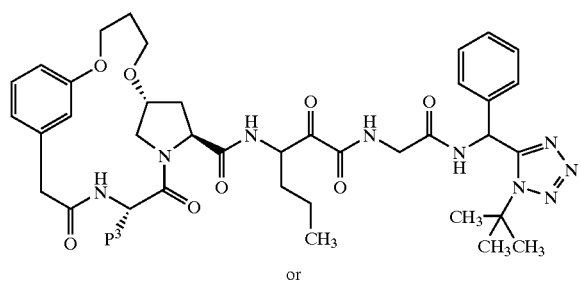

or

-continued

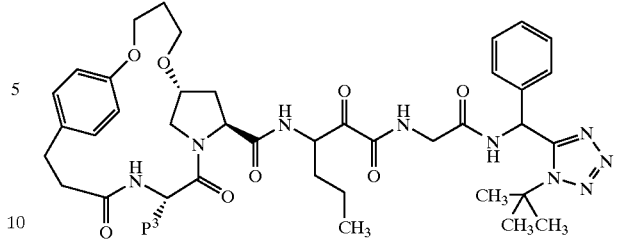

wherein $P^3$ is an isopropyl, tertiary butyl, cyclopentyl, or cyclohexyl moiety.

14. A pharmaceutical composition comprising as an active ingredient a compound of claim 1 and a pharmaceutically acceptable carrier.

15. The pharmaceutical composition of claim 14, additionally containing an antiviral agent.

16. The pharmaceutical composition claim 15, additionally containing an interferon.

17. The pharmaceutical composition of claim 16, wherein said antiviral agent is ribavirin and said interferon is α-interferon.

18. A compound selected from:

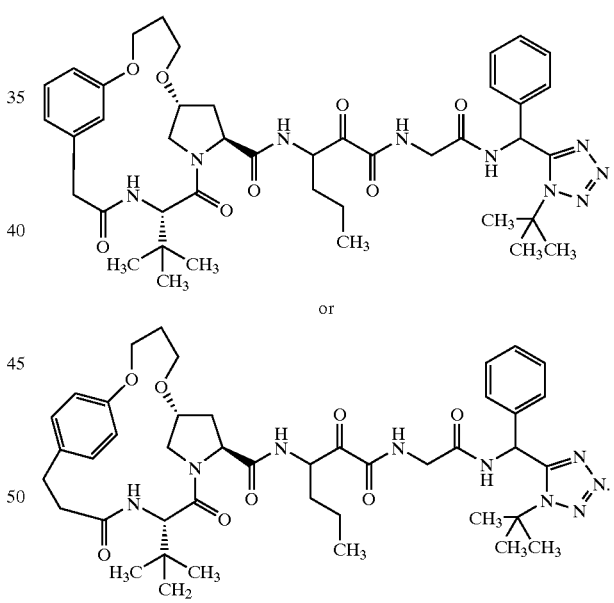

19. A method of treating disorders associated with the "Hepatitis C Virus" HCV, said method comprising administering to a patient in need of such treatment a pharmaceutical composition which comprises therapeutically effective amounts of a compound of claim 1.

20. The method of claim 19, wherein said administration is subcutaneous.

* * * * *

UNITED STATES PATENT AND TRADEMARK OFFICE
CERTIFICATE OF CORRECTION

PATENT NO.     : 6,911,428 B2
DATED          : June 28, 2005
INVENTOR(S)    : Zhu, Zhaoning It is certified that error appears in the above-identified patent and that said Letters Patent is hereby corrected as shown below:

Column 125,
Line 47, please insert a missing comma between "alkyl-aryl" and "alkyl ether".

Column 126,
Line 31, please insert a missing semicolon -- ; -- after "U is N".

Column 127,
Line 35, please insert a missing comma between "alkylcarbonyl" and "arylcarbonyl".
Line 46, please correct "$A^1$" to -- $Ar^1$ --.

Column 129,
Lines 41-50, please correct the two structures with the missing nitrogen atoms to:

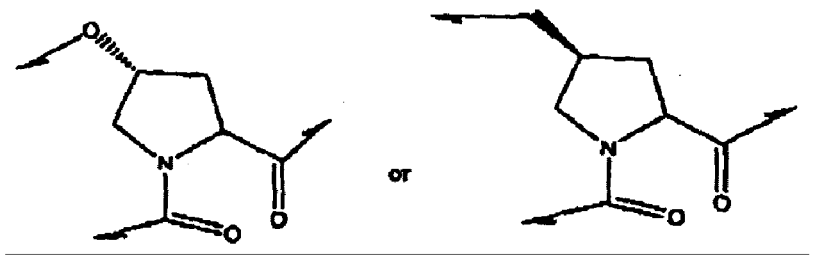

UNITED STATES PATENT AND TRADEMARK OFFICE
CERTIFICATE OF CORRECTION

PATENT NO. : 6,911,428 B2
DATED : June 28, 2005
INVENTOR(S) : Zhu, Zhaoning

It is certified that error appears in the above-identified patent and that said Letters Patent is hereby corrected as shown below:

Column 130,
Lines 44-56, please correct the structures as follows:

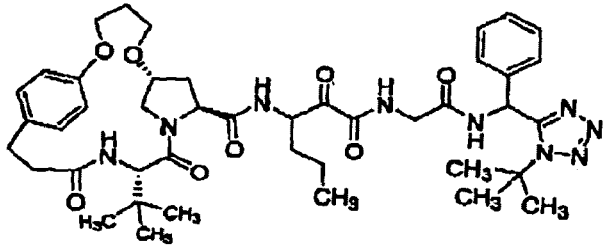

Signed and Sealed this

Fourth Day of October, 2005

JON W. DUDAS
*Director of the United States Patent and Trademark Office*